(12) United States Patent
Jackson et al.

(10) Patent No.: US 7,534,445 B2
(45) Date of Patent: *May 19, 2009

(54) CHLAMYDIA PROTEIN, SEQUENCE AND USES THEREOF

(75) Inventors: W. James Jackson, Marriottsville, MD (US); John L. Pace, Blue Bell, PA (US)

(73) Assignee: Emergent Product Development Gaithersburg Inc., Gaithersburg, MD (US)

( * ) Notice: Subject to any disclaimer, the term of this patent is extended or adjusted under 35 U.S.C. 154(b) by 647 days.

This patent is subject to a terminal disclaimer.

(21) Appl. No.: 10/766,711

(22) Filed: Jan. 27, 2004

(65) Prior Publication Data

US 2004/0137005 A1 Jul. 15, 2004

Related U.S. Application Data

(63) Continuation of application No. 08/942,596, filed on Oct. 2, 1997, now Pat. No. 7,459,524.

(51) Int. Cl.
*A61K 39/118* (2006.01)
*C07K 14/295* (2006.01)
*C12P 21/04* (2006.01)
*C07H 21/04* (2006.01)

(52) U.S. Cl. .............. 424/263.1; 424/190.1; 530/350; 536/23.1; 536/23.7; 435/69.1; 435/69.7

(58) Field of Classification Search .............. 530/300, 530/350; 536/23.7; 435/69.7; 424/190.1, 424/192.1, 234.1, 263.1
See application file for complete search history.

(56) References Cited

U.S. PATENT DOCUMENTS

| | | | |
|---|---|---|---|
| 4,427,782 A | 1/1984 | Caldwell et al. |
| 4,855,283 A | 8/1989 | Lockhoff et al. |
| 4,935,352 A | 6/1990 | Igarashi et al. |
| 5,071,962 A | 12/1991 | Morrison et al. |
| 5,516,638 A | 5/1996 | Urnovitz et al. |
| 5,565,352 A | 10/1996 | Hochstrasser et al. |
| 5,629,167 A | 5/1997 | Ratti |
| 5,725,863 A | 3/1998 | Daniels et al. |
| 5,750,110 A | 5/1998 | Prieels et al. |
| 5,849,306 A | 12/1998 | Sim et al. |
| 5,871,977 A | 2/1999 | Kubota et al. |
| 5,965,141 A | 10/1999 | Briles et al. |
| 5,976,544 A | 11/1999 | Charles et al. |
| 6,019,982 A | 2/2000 | Clements et al. |
| 6,077,693 A | 6/2000 | Tang et al. |
| 6,565,856 B1 | 5/2003 | Skeiky et al. |
| 6,642,023 B1 | 11/2003 | Jackson et al. |
| 7,419,807 B2 | 4/2004 | Jackson et al. |
| 6,887,843 B1 | 5/2005 | Jackson et al. |
| 2004/0037846 A1 | 2/2004 | Jackson |
| 2004/0067524 A1 | 4/2004 | Jackson et al. |
| 2005/0048557 A1 | 3/2005 | Jackson et al. |
| 2005/0281847 A1 | 12/2005 | Berthet et al. |

FOREIGN PATENT DOCUMENTS

| | | |
|---|---|---|
| EP | 0 818 681 A1 | 1/1998 |
| WO | WO 94/01548 | 1/1994 |
| WO | WO 95/12411 | 5/1995 |
| WO | WO 96/31236 | 10/1996 |
| WO | WO 98/10789 | 3/1998 |
| WO | WO 99/17741 A1 | 4/1999 |
| WO | WO 99/28475 A2 | 6/1999 |
| WO | WO 99/31236 A2 | 6/1999 |
| WO | WO 00/34483 A2 | 6/2000 |
| WO | WO 01/40474 A2 | 6/2001 |
| WO | WO 02/08267 A2 | 1/2002 |

OTHER PUBLICATIONS

Bowie et al (Science, 1990, 257:1306-1310).*
Coleman et al. (Research in Immunology, 1994; 145(1): 33-36).*
Abaza et al. (Journal of Protein Chemistry, vol. 11, No. 5, 1992, pp. 433-444.*
accession No. H81722 ; accession No. G71460.*
Brunham et al 2005, Nature Reviews, vol. 5, pp. 149-161.*
Birkelund et al. Infect Immun. 56(3): 654-9 (1988).
Buendia et al. FEMS Microbiol Lett. 150(1): 113-9 (1997).
Caldwell et al., 1981, Infect. and Immun. 31:1161-1176.
Caldwell, et al., Infec. Immun., 31(3):1161-1176 (1981).
Carlson et al., Infect Immun. vol. 65: No. 6; p. 2080-2087 (1997).
Cerrone et al., Infec. Immun., 59(1):79-90 (1991).
Chen et al., Molecular Microbiology 11(3):501-507 (1994).
Christiansen et al., Scand J Infect Dis Suppl, 104:5-10 (1997).
DeSa et al. Infect Immun. 63(12): 4912-6 (1995).
Deslauriers et al., Infect Immun. vol. 64: No. 2; p. 434-440 (1996).
Herring et al., FEMS Microbiol Letts. 65:153-158 (1989).
Li et al. PNAS 77(6): 3211-14 (1980).
Murdin et al., Infec. Immun., 61(10):4406-4414 (1993).
Murdin et al., Infec. Immun., 63(3):1116-1121 (1995).

(Continued)

*Primary Examiner*—Robert B Mondesi
*Assistant Examiner*—Padma V Baskar
(74) *Attorney, Agent, or Firm*—Sterne, Kessler, Goldstein & Fox P.L.L.C.

(57) ABSTRACT

A high molecular weight ("HMW") protein of *chlamydia*, the amino acid sequence thereof, and antibodies that specifically bind the HMW protein are disclosed as well as the nucleic acid sequence encoding the same. Also disclosed are prophylactic and therapeutic compositions, comprising the HMW protein, a fragment thereof, or an antibody that specifically binds the HMW protein or a portion thereof, or the nucleotide sequence encoding the HMW protein or a fragment thereof, including vaccines.

34 Claims, 11 Drawing Sheets

OTHER PUBLICATIONS

Pal et al., Infection & Immunity, 65:3361-3369, Aug. (1997).
Sandbulte et al., Veterinary Microbiology, 48:269-282 (1996).
Sexton et al. J. Immunol., 152(4):1861-72 (1994).
Stephens et al., J. Bacteriol 168:1277-82 (1986).
Su et al. PNAS 93: 11134-48 (1996).
Swanson et al., Infec. Immun., 38(2):502-507 (1990).
Tan et al., Infect Immun. 58(9) 3101-3108 (1990).
Wagar et al., Infect. Immun., 56(7):1678-1684 (1988).
Zhang et al., Cell, 69:861-869 (1992).
Zhang et al., Nucleic Acids Res. 18(4):1061 (1990).
Amersdorfer, P., et al., "Molecular Characterization of Murine Humoral Immune Response to Botulinum Neurotoxin Type A Binding Domain as Assessed by Using Phage Antibody Libraries," *Infect. Immun.* 65:3743-3752, American Society For Microbiology (Sep. 1997).
Barenkamp, S.J., and St. Geme III, J.W., "Identification of Surface-Exposed B-Cell Epitopes on High-Molecular-Weight Adhesion Proteins of Nontypeable *Haemophilus influenzae*," *Infect. Immun.* 64:3032-3037, American Society For Microbiology (Aug. 1996).
Batteiger, B.E., et al., "Species—, Serogroup—, and Serovar-Specific Epitopes Are Juxtaposed in Variable Sequence Region 4 of the Major Outer Membrane Proteins of Some *Chlamydia trachomatis* Serovars," *Infect. Immun.* 64:2839-2841, American Society For Microbiology (Jul. 1996).
Baughn, R.E. et al., "Epitome Mapping of B-Cell Determinants on the 15-Kilodalton Lipoprotein of *Treponema pallidum* (Tpp15) with Synthetic Peptides," *Infect. Immun.* 64:2457-2466, American Society For Microbilgy (Jul. 1996).
Brown, D.R., et al., "Identification and Characterization of a Neutralizing Monoclonal Antibody Against Botulinum Neurotoxin, Serotype F, Following Vaccination With Active Toxin," *Hybridoma* 16:447-456, Mary Ann Leibert, Inc. (Oct. 1997).
Burnie, J.P., et al., "Defining Antibody Targets in *Streptococcus oralis* Infection," *Infect. Immun.* 64:1600-1608, American Society For Microbiology (May 1996).
Choh, H.L., et al., "β-Endorphin omission analogs: dissociation of immunoreactivity from other biological activities," *Proc. Natl. Acad. Sci. USA* 77:3211-3214, National Academy of Sciences (1980).
Cunningham, M.W., et al., "Molecular Analysis of Human Cardiac Myosin-Cross-Reactive B- and T-Cell Epitopes of the Group A Streptococcal M5 Protein," *Infect. Immun.* 65:3913-3923, American Society For Microbiology (Sep. 1997).
Davies, D.R., and Cohen, G.H., "Interactions of protein antigens with antibodies," *Proc. Natl. Acad. Sci. USA* 93:7-12, National Academy of Sciences (Jan. 1996).
De Sa, C., "La protéine majeure de la membrane externe de *Chlamydia*: structure et fonctions," *Vet. Res.* 27:317-331, ZDP Sciences (Feb. 1996).
Delvig, A.A., et al., "Immune responses to linear epitopes on the PorB protein of *Neisseria meningitidis* in patients with systemic meningococcal disease," *Microbiology* 142:2491-2498, Society for General Microbiology (Sep. 1996).
Dium, B., et al., "Fine Mapping of Outer Membrane Protein P2 Antigenic Sites Which Vary During Persistent Infection by *Haemophilus influenzae*," *Infect. Immun.* 64:4673-4679, American Society For Microbiology (Nov. 1996).
Fan, J., and Stephens, R.S., "Antigen Conformation Dependence of *Chlamydia trachomatis* Infectivity Neutralization," *J. Infect. Dis.* 176:713-721, University of Chicago Press (Sep. 1997).
Ghadjari, A., et al., "Epitome mapping *Candida albicans* proteinase (SAP 2)," *FEMS Immunol. Med. Microbiol.* 19:115-123, Elsevier Science (Oct. 1997).
Goodman, J.W., "Immunogenicity & Antigenicity," in *Basic and Clinical Immunol.*, Stites, D.P., et al., eds., Appleton & Lange, Norwalk, CT, pp. 102-108 (1991).
Janeway, C., et al., *Immunogenicity,.*, John Wiley & Sons, Inc., New York, NY, pp. 65-71 (1989).
Lainson, F.A., et al., " Characterization of epitopes involved in the neutralization of *Pasteurella haemolytica* serotype A1 leukotoxin," *Microbiology* 142:2499-2507, Society for General Microbiology (Sep. 1996).

Méchin. M., et al., "Identification of Surface-Exposed Linear B-Cell Epitopes of the Nonfimbrial Adhesin CS31A of *Escherichia coli* by Using Overlapping Peptides and Antipeptide Antibodies," *Infect. Immun.* 64:3555-3564, American Society for Microbiology (Sep. 1996).
Morris, G.E., *Epitope Mapping Protocols*, Morris, G.E., ed., Humana Press, Inc., Totowa, NJ, 5 pages (1996).
Oettinger, T., et al., "Characterization of the Delayed Type Hypersensitivity-Inducing Epitope of MPT64 from *Mycobacterium tuberculosis*," *Scand. J. Immunol.* 45:499-503, Blackwell Science, Ltd. (May 1997).
Pal, S., et al., "Monoclonal immunoglobulin A antibody to the major outer membrane protein of *Chlamydia trachomatis* mouse pneumonitis biovar protects mice against a genital chlamydial challenge," *Vaccine* 15:575-582, Elsevier Science (Apr. 1997).
Read, T.D., et al., "Genome sequence of *Chlamydophila caviae* (*Chlamydia psittaci* GPCI): examining the role of niche-specific genes in the evolution of the Chlamydiaceae," *Nucleic Acids Res.* 31:2134-2147, Oxford University Press (Apr. 2003).
Roitte, I., et al., *Immunology*, Roitt, I., et al., eds., St. Louis, MO, CV. Mosby, pp. 7.1-7.10 (1989).
Saint-Remy, J.R., "Epitope mapping: a new method for biological evaluation and immunotoxicology," *Toxicology* 119:77-81, Elsevier Science (Apr. 1997).
Takahashi, I., et al., "Epitome Maps of the *Escherichia coli* Heat-Labile Toxin B Subunit for Development of a Synthetic Oral Vaccine," *Infect. Immun.* 64:1290-1298, American Society for Microbiology (Apr. 1996).
Wood, A.C., et al., "Identification of antigenic sites on staphylococcal enterotoxin B and toxoid," *FEMS Immunol. Med. Microbiol.* 17:1-10, Elsevier Science (Jan. 1997).
Yanagisawa, S., et al., "Mapping of $V_\beta 11^+$ helper T cell epitopes on mycobacterial antigen in mouse primed with *Myobacterium tuberculosis*," *Int. Immunol.* 9:227-237, Oxford University Press (Feb. 1997).
Zhao, Q., et al., "Recall of Original Serologic Response after Challenge with Homologous and Heterologous *Chlamydia trachomatis* Serovars," *J. Infect. Dis.* 173:609-618, The University of Chicago Press (Mar. 1996).
Zhong, G., et al., "Antibody Recognition of a Neutralization Epitope on the Major Outer Membrane Protein of *Chlamydia trachomatis*," *Infect. Immun.* 62:1576-1583, American Society for Microbiology (May 1994).
Zhu, Y., et al., "Identification of a *Coccidioides immitis* Antigen 2 Domain That Expresses B-Cell-Reactive Epitopes," *Infect. Immun.* 65:3376-3380, American Society for Microbiology (Aug. 1997).
Co-pending U.S. Appl. No. 08/942,596, inventors Jackson, W.J., et al., filed Oct. 2, 1997 (Not Published).
NCBI Entrez, GenBank Report, Accession No. R91549, Hillier, L., et al. (1995).
International Search Report for International Appl. No. PCT/US98/20737, mailed on Mar. 24, 1999, ISA/US, Washington, D.C., USA.
Lederman, S., et al., "A Single Amino Acid Substitution in a Common African Allele of the CD4 Molecule Ablates Binding of the Monoclonal Antibody, OKT4." *Molecular Immunology*, 28(11): 1171-1181 *Pregamon Press plc* (Nov. 1991).
Li, C., et al., "β-Endorphin omission analogs: Dissociation of immunoreactivity from other biological activities." *Proceedings of National Academy of Science U.S.A.* 77(6): 3211-3214 *National Academy of Sciences* (Jun. 1980).
Unanue, Emile R. "Rous-Whipple Award Lecture: Chemical Features of Peptide Selection by Class II Histocompatibility Molecules." *American Journal of Pathology*, 154(3): 651-664 *American Society for Investigative Pathology* (Mar. 1999).
Batteiger, B.E., et al., "Partial protection against genital reinfection by immunization of guinea-pigs with isolated outer-membrane proteins of the chlamydial agent of guinea-pig inclusion conjunctivitis," *J. Gen. Microbiol.* 139:2965-2972, SGM (1993).
Bork, P., "Powers and pitfalls in sequence analysis: the 70% hurdle," *Genome Res.* 10:398-400, Cold Spring Harbor Laboratory Press (Apr. 2000).

Bork, P., and Bairoch, A., "Go hunting in sequence databases but watch out for the traps," *Trends Genet.* 12:425-427, Elsevier Trends Journals (Oct. 1996).

Brenner, S.E., "Errors in genome annotation," *Trends Genet.* 15:132-133, Elsevier Trends Journals (Apr. 1999).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biol.* 111:2129-2138, The Rockefeller University Press (1990).

Bush, R.M., and Everett, K.D.E., "Molecular evolution of the *Chlamydiaceae,*" *Int. J. System. Evol. Microbiol.* 51:203-220, IUMS (Jan. 2001).

Clyne, J.M., et al., "A rapid chemiluminescent DNA hybridization assay for the detection of *Chlamydia trachomatis,*" *J. Biolumin. Chemilumin.* 4:357-366, Wiley & Sons (1989).

Denamur, E., et al., "Restriction pattern of the major outer-membrane protein gene provides evidence for a homogeneous invasive group among ruminant isolates of *Chlamydia psittaci,*" *J. Gen. Microbiol.* 137:2525-2530, SGM (1991).

Doerks, T., et al., "Protein annotation: detective work for function prediction," *Trends Genet.* 14:248-250, Elsevier Trends Journals (Jun. 1998).

Griffiths, P.C., et al., "Epizootic bovine abortion in a dairy herd: characterization of a *Chlamydia psittaci* isolate and antibody response," *Br. Vet. J.* 151:683-693, Bailliere Tindall (1995).

Herbert, *The Dictionary of Immunol., 3rd Ed.*, Academic Press, London, pp. 58-59 (1985).

Hutchinson, C.A., et al., "Mutagenesis at a Specific Position in a DNA Sequence," *J. Biol. Chem.* 253-6551-6560, The American Society of Biological Chemists, Inc. (1978).

Jenkins, F.J., "Basic Methods for the Detection of PCR Products," *PCR Methods and Apps. Manual Supplement*, pp. S77-S82, Cold Spring Harbor Laboratory (1994).

Ji, Y., et al., "Intranasal Immunization with C5a Peptidase Prevents Nasopharyngeal Colonization of Mice by the Group A *Streptococcus,*" *Infect. Immun.* 65:2080-2087, American Society for Microbiology (1997).

Jobling, M.G., and Holmes, R.K., "Analysis of structure and function of the B subunit of cholera toxin by the use of site-directed mutagenesis," *Mol. Microbiol.* 5:1755-1767, Blackwell Scientific Publicationso (1991).

Kalman, S., et al., "Comparative genomes of *Chlamydia pneumoniae* and *C. trachomatis,*" *Nat. Genet.* 21:385-389 (Apr. 1999).

Krieg, A.M., "Therapeutic potential of Toll-like receptor 9 activation," *Nat. Rev. Drug Discov.* 5:471-484, Nature Publishing Group (Jun. 2006).

Lazar, E., et al., "Transforming Growth Factor α: Mutation of Aspartic Acid 47 and Leucine 48 Results in Different Biological Activities," *Mol. Cell. Biol.* 8:1247-1252, American Society for Microbiology (1988).

Mygind, P.H., et al., "Membrane proteins PmpG and PmpH are major constituents of *Chlamydia trachomatis* L2 outer membrane complex," *FEMS Microbiol. Lett.* 186:163-169, Blackwell Publisher (May 2000).

Ngo, J.T., et al., in *The Protein Folding Problem and Tertiary Structure Prediction*, Merz, et al., eds., Birkhauser, Boston, MA, pp. 492-495 (1994).

Peipert, J.F., "Genital Chlamydial Infections," *N. Engl. J. Med.* 349:2424-2430, Massachusetts Medical Society (Dec. 2003).

Rank, R.G., "Animal Models for Urogenital Infections," in *Methods in Enzymology* vol. 235, *Bacterial Pathogenesis Part A—Identification and Regulation of Virulence Factors*, Clark, V.L., and Bavoil, P.M., eds., Academic Press, New York, NY, pp. 83-93 (1994).

Rudinger, J., "Characteristics of the amino acids as components of a peptide hormone sequence," in *Peptide Hormones*, Parsons, J.A., ed., University Park Press, Baltimore, MD, pp. 1-6 (1976).

Scopes, R.K., "Overview of Protein Purification and Characterization," in *Current Protocols in Protein Science*, Taylor, G., ed., John Wiley & Sons, Inc., pp. 1.1.1-1.1.6 (1995).

Shaw, A.C., et al., "Comparative proteome analysis of *Chlamydia trachomatis* serovar A, D and L2," *Proteomics* 2:164-186, Wiley-VCH Verlag GmbH (Feb. 2002).

Skolnick, J., and Fetrow, J.S., "From genes to protein structure and function: novel applications of computational approaches in the genomic era," *Trends Biotechnol.* 18:34-39, Elsevier Science Publishers (Jan. 2000).

Smith, "Anal of Pro," in *Short Protocols in Mol. Biol.*, Ausubel, F.M., ed., John Wiley & Sons, Inc., pp. 10-1 to 10-4 (1997).

Smith, T.X., and Zhang, X., "The challenges of genome sequence annotation or the devil is in the details," *Nature Biotechnol.* 15:1222-1223, Nature America Publishing (Nov. 1997).

Stephens, R.S., et al., "Genome Sequence of an Obligate Intracellular Pathogen of Humans: *Chlamydia trachomatis*" *Science* 282:754-759, American Association for the Advancement of Science (1998).

Su, H., et al., "Protective efficacy of a parenterally administered MOMP-derived synthetic oligopeptide vaccine in a murine model of *Chlamydia trachomatis* genital tract infection: serum neutralizing IgG antibodies do not protect against chlamydial genital tract infection," *Vaccine* 13:1023-1032, Elsevier Science Ltd. (1995).

Tanzer, R.J., and Hatch, T.P., "Characterization of Outer Membrane Proteins in *Chlamydia trachomatis* LGV Serovare L2," *J. Bacteriol.* 183:2686-2690, American Society for Microbiology (Apr. 2001).

Tuffrey, M., et al., "Heterotypic protection of mice against *Chlamydial salpingitis* and colonization of the lower genital tract with a human serovar F isolate of *Chlamydia trachomatis* by prior immunization with recombinant serovar L1 major outer-membrane protein," *J. Gen. Microbiol.* 138:1707-1715, Society For General Microbiology (1992).

Webster's New World, Third, pp. 675 and 1472 (1988).

Wells, J.A., "Additivity of mutational effects in proteins," *Biochemistry* 29:8509-8517, American Chemical Society (1990).

ATCC Accession No. VR-902B, "*Chlamydia trachomatis* (Busacca) Rake, Lymphogranuloma enereum (LGV II) strain 434".

NCBI Entrez, GenBank Report, Accession No. ABB22785, Halse, T.A., et al. (first entered Oct. 2005, last revised Aug. 2006).
NCBI Entrez, GenBank Report, Accession No. AAP05029, Read, T.D. (first entered Apr. 2003, last revised Dec. 2005).
Co-pending and commonly-owned U.S. Appl. No. 09/677,752, inventor W. James Jackson, filed on Oct. 2, 2000 (Not Published).
Co-pending and commonly-owned U.S. Appl. No. 11/781,203, inventor W. James Jackson, filed on Jul. 20, 2007 (Not Published).
Co-pending and commonly-owned U.S. Appl. No. 11/781,199, inventor W. James Jackson, filed on Jul. 20, 2007 (Not Published).

* cited by examiner

```
GGGCAAAACTCTTCCCCCCGGGATTTATATGGGAAAGGGGAAACTTTGGC
CCGTATTCAAGCGCCACGGGTTTTGGGGCGGAATGAATTTTTTCGTTCCG
GAAAAAGTAATTCCCCGGGAACGTAGGGTATCGGTTTCATAGGCTCGCCA
AATGGGATATAGGTGGAAAGGTAAAAAAAACTGAGCCAAGCAAAGGATAG
AGAAGTCTTGTAATCATCGCAGGTTAAAGGGGGGATGTTATTTTAGCCTG
CAAATAGTGTAATTATTGGATCCTGTAAAGAGAAAAGGACGAATGCCCTG
AAGATAAGAACATTTATTGATATTAAATTATTAATTTTTTATGAAGCGGA
GTAATTAATTTTATCTCTCAGCTTTTGTGTGATGCAAACGTCTTTCCATA
AGTTCTTTCTTTCAATGATTCTAGCTTATTCTTGCTGCTCTTTAAATGGG
GGGGGATATGCAGCAGAAATCATGGTTCCTCAAGGAATTTACGATGGGGA
GACGTTAACTGTATCATTTCCCTATACTGTTATAGGAGATCCGAGTGGGA
CTACTGTTTTTTCTGCAGGAGAGTTAACATTAAAAAAATCTTGACAATTCT
ATTGCAGCTTTGCCTTTAAGTTGTTTTGGGAACTTATTAGGGAGTTTTAC
TGTTTTAGGGAGAGGACACTCGTTGACTTTCGAGAACATACGGACTTCTA
CAAATGGGGCAGCTCTAAGTAATAGCGCTGCTGATGGACTGTTTACTATT
GAGGGTTTTAAAGAATTATCCTTTTCCAATTGCAATTCATTACTTGCCGT
ACTGCCTGCTGCAACGACTAATAAGGGTAGCCAGACTCCGACGACAACAT
CTACACCGTCTAATGGTACTATTTATTCTAAAACAGATCTTTTGTTACTC
AATAATGAGAAGTTCTCATTCTATAGTAATTTAGTCTCTGGAGATGGGGG
AGCTATAGATGCTAAGAGCTTAACGGTTCAAGGAATTAGCAAGCTTTGTG
TCTTCCAAGAAAATACTGCTCAAGCTGATGGGGGAGCTTGTCAAGTAGTC
ACCAGTTTCTCTGCTATGGCTAACGAGGCTCCTATTGCCTTTGTAGCGAA
TGTTGCAGGAGTAAGAGGGGGAGGGATTGCTGCTGTTCAGGATGGGCAGC
AGGGAGTGTCATCATCTACTTCAACAGAAGATCCAGTAGTAAGTTTTTCC
AGAAATACTGCGGTAGAGTTTGATGGGAACGTAGCCCGAGTAGGAGGAGG
GATTTACTCCTACGGGAACGTTGCTTTCCTGAATAATGGAAAAACCTTGT
TTCTCAACAATGTTGCTTCTCCTGTTTACATTGCTGCTAAGCAACCAACA
AGTGGACAGGCTTCTAATACGAGTAATAATTACGGAGATGGAGGAGCTAT
CTTCTGTAAGAATGGTGCGCAAGCAGGATCCAATAACTCTGGATCAGTTT
CCTTTGATGGAGAGGGAGTAGTTTTCTTTAGTAGCAATGTAGCTGCTGGG
AAAGGGGGAGCTATTTATGCCAAAAAGCTCTCGGTTGCTAACTGTGGCCC
TGTACAATTTTTAAGGAATATCGCTAATGATGGTGGAGCGATTTATTTAG
GAGAATCTGGAGAGCTCAGTTTATCTGCTGATTATGGAGATATTATTTTC
```

FIG. 2A

```
GATGGGAATCTTAAAAGAACAGCCAAAGAGAATGCTGCCGATGTTAATGG
CGTAACTGTGTCCTCACAAGCCATTTCGATGGGATCGGGAGGGAAAATAA
CGACATTAAGAGCTAAAGCAGGGCATCAGATTCTCTTTAATGATCCCATC
GAGATGGCAAACGGAAATAACCAGCCAGCGCAGTCTTCCAAACTTCTAAA
AATTAACGATGGTGAAGGATACACAGGGGATATTGTTTTTGCTAATGGAA
GCAGTACTTTGTACCAAAATGTTACGATAGAGCAAGGAAGGATTGTTCTT
CGTGAAAAGGCAAAATTATCAGTGAATTCTCTAAGTCAGACAGGTGGGAG
TCTGTATATGGAAGCTGGGAGTACATGGGATTTTGTAACTCCACAACCAC
CACAACAGCCTCCTGCCGCTAATCAGTTGATCACGCTTTCCAATCTGCAT
TTGTCTCTTTCTTCTTTGTTAGCAAACAATGCAGTTACGAATCCTCCTAC
CAATCCTCCAGCGCAAGATTCTCATCCTGCAGTCATTGGTAGCACAACTG
CTGGTTCTGTTACAATTAGTGGGCCTATCTTTTTTGAGGATTTGGATGAT
ACAGCTTATGATAGGTATGATTGGCTAGGTTCTAATCAAAAAATCAATGT
CCTGAAATTACAGTTAGGGACTAAGCCCCCAGCTAATGCCCCATCAGATT
TGACTCTAGGGAATGAGATGCCTAAGTATGGCTATCAAGGAAGCTGGAAG
CTTGCGTGGGATCCTAATACAGCAAATAATGGTCCTTATACTCTGAAAGC
TACATGGACTAAAACTGGGTATAATCCTGGGCCTGAGCGAGTAGCTTCTT
TGGTTCCAAATAGTTTATGGGGATCCATTTTAGATATACGATCTGCGCAT
TCAGCAATTCAAGCAAGTGTGGATGGGCGCTCTTATTGTCGAGGATTATG
GGTTTCTGGAGTTTCGAATTTCTTCTATCATGACCGCGATGCTTTAGGTC
AGGGATATCGGTATATTAGTGGGGGTTATTCCTTAGGAGCAAACTCCTAC
TTTGGATCATCGATGTTTGGTCTAGCATTTACCGAAGTATTTGGTAGATC
TAAAGATTATGTAGTGTGTCGTTCCAATCATCATGCTTGCATAGGATCCG
TTTATCTATCTACCCAACAAGCTTTATGTGGATCCTATTTGTTCGGAGAT
GCGTTTATCCGTGCTAGCTACGGGTTTGGGAATCAGCATATGAAAACCTC
ATATACATTTGCAGAGGAGAGCGATGTTCGTTGGGATAATAACTGTCTGG
CTGGAGAGATTGGAGCGGGATTACCGATTGTGATTACTCCATCTAAGCTC
TATTTGAATGAGTTGCGTCCTTTCGTGCAAGCTGAGTTTTCTTATGCCGA
TCATGAATCTTTTACAGAGGAAGGCGATCAAGCTCGGGCATTCAAGAGCG
GACATCTCCTAAATCTATCAGTTCCTGTTGGAGTGAAGTTTGATCGATGT
TCTAGTACACATCCTAATAAATATAGCTTTATGGCGGCTTATATCTGTGA
TGCTTATCGCACCATCTCTGGTACTGAGACAACGCTCCTATCCCATCAAG
AGACATGGACAACAGATGCCTTTCATTTAGCAAGACATGGAGTTGTGGTT
AGAGGATCTATGTATGCTTCTCTAACAAGTAATATAGAAGTATATGGCCA
TGGAAGATATGAGTATCGAGATGCTTCTCGAGGCTATGGTTTGAGTGCAG
```

FIG. 2B

```
GAAGTAGAGTCCGGTTCTAAAAATATTGGTTAGATAGTTAAGTGTTAGCG
ATGCCTTTTTCTTTGAGATCTACATCATTTTGTTTTTTAGCTTGTTTGTG
TTCCTATTCGTATGGATTCGCGAGCTCTCCTCAAGTGTTAACGCCTAATG
TAACCACTCCTTTTAAGGGAGACGATGTTTACTTGAATGGAGACTGCGCT
TTTGTCAATGTCTATGCAGGAGCTGAAGAAGGTTCGATTATCTCAGCTAA
TGGCGACAATTTAACGATTACCGGACAAAACCATACATTATCATTTACAG
ATTCTCAAGGGCCAGTTCTTCAAAATTATGCCTTCATTTCAGCAGGAGAG
ACACTTACTCTGAGAGATTTTTCGAGTCTGATGTTCTCGAAAAATGTTTC
TTGCGGAGAAAAGGGAATGATCTCCGGGAAAACCGTGAGTATTTCCGGAG
CAGGCGAAGTGATTTTCTGGGATAACTCCGTGGGTATTCTCCTTTATCT
ACTGTGCCAACCTCATCATCAACTCCGCCTGCTCCAACAGTTAGTGATGC
TCGGAAAGGGTCTATTTTTTCTGTAGAGACTAGTTTGGAGATCTCAGGCG
TCAAAAAGGGGTCATGTTCGATAATAATGCCGGGAATTTCGGAACAGTT
TTTCGAGGTAAGAATAATAATAATGCTGGTGGTGGCAGGCAGTGGGTTCCG
CTACACCATCAAGTACGACTTTTACAGTTAAAAACTGTAAAGGGAAAGTT
TCTTTCACAGATAACGTAGCCTCTTGCGGAGGCGGAGTGGTTTATAAAGG
CATTGTGCTTTTCAAAGACAATGAAGGAGGCATATTCTTCCGAGGGAACA
CAGCATACGATGATTTAAGGATTCTTGCTGCTACTAATCAGGATCAGAAT
ACGGAGACAGGAGGCGGTGGAGGAGTTATTTGCTCTCCAGATGATTCTGT
AAAGTTTGAAGGCAATAAAGGTTCTATTGTTTTTGATTACAACTTTGCAA
AAGGCAGAGGCGGAAGCATCCTAACGAAAGAATTC
```

FIG. 2C

MQTSFHKFFLSMILAYSCCSLNGGGYAAEIMVPQGIYDGETLTVSFPYTV
IGDPSGTTVFSAGELTLKNLDNSIAALPLSCFGNLLGSFTVLGRGHSLTF
ENIRTSTNGAALSNSAADGLFTIEGFKELSFSNCNSLLAVLPAATTNKGS
QTPTTTSTPSNGTIYSKTDLLLLNNEKFSFYSNLVSGDGGAIDAKSLTVQ
GISKLCVFQENTAQADGGACQVVTSFSAMANEAPIAFVANVAGVRGGGIA
AVQDGQQGVSSSTSTEDPVVSFSRNTAVEFDGNVARVGGGIYSYGNVAFL
NNGKTLFLNNVASPVYIAAKQPTSGQASNTSNNYGDGGAIFCKNGAQAGS
NNSGSVSFDGEGVVFFSSNVAAGKGGAIYAKKLSVANCGPVQFLRNIAND
GGAIYLGESGELSLSADYGDIIFDGNLKRTAKENAADVNGVTVSSQAISM
GSGGKITTLRAKAGHQILFNDPIEMANGNNQPAQSSKLLKINDGEGYTGD
IVFANGSSTLYQNVTIEQGRIVLREKAKLSVNSLSQTGGSLYMEAGSTWD
FVTPQPPQQPPAANQLITLSNLHLSLSSLLANNAVTNPPTNPPAQDSHPA
VIGSTTAGSVTISGPIFFEDLDDTAYDRYDWLGSNQKINVLKLQLGTKPP
ANAPSDLTLGNEMPKYGYQGSWKLAWDPNTANNGPYTLKATWTKTGYNPG
PERVASLVPNSLWGSILDIRSAHSAIQASVDGRSYCRGLWVSGVSNFFYH
DRDALGQCYRYISGGYSLGANSYFGSSMFGLAFTEVFGRSKDYVVCRSNH
HACIGSVYLSTQQALCGSYLFGDAFIRASYGFGNQHMKTSYTFAEESDVR
WDNNCLAGEIGAGLPIVITPSKLYLNELRPFVQAEFSYADHESFTEEGDQ
ARAFKSGHLLNLSVPVGVKFDRCSSTHPNKYSFMAAYICDAYRTISGTET
TLLSHQETWTTDAFHLARHGVVVRGSMYASLTSNIEVYGHGRYEYRDASR
GYGLSAGSRVRF

FIG. 3

```
L2                                           EIMVPQGIYDGETLTVSFPYTVIGDPSGTTVF
F
B

100*
L2   SAGELTLKNLDNSIAALPLSCFGNLLGSFTVLGRGHSLTFENIRTSTNGAALSNSAADGL
F                                                          ┆ ┆┆
                                                           D NS
B                                                          ┆ ┆┆
                                                           D NS

L2   FTIEGFKELSFSNCNSLLAVLPAATTNKGSQTPTTTSTPSNGTIYSKTDLLLLNNEKFSFY
F              ┆              ┆         ┆
               P              N         S
B              ┆              ┆         ┆
               P              N         S
                     200*
L2   SNLVSGDGGAIDAKSLTVQGISKLCVFQENTAQADGGACQVVTSFSAMANEAPIAFVA
F       ┆    ┆                                              ┆
        S    T                                              I
B       ┆    ┆                                              ┆
        S    T                                              I

L2   NVAGVRGGGIAAVQDGQQGVSSSTSTFDPVVSFSRNTAVEFDGNVARVGGGIYSYGNV
F
B

*300
L2   AFLNNGKTLFLNNVASPVYIAAKQPTSGQASNTSNNYGDGGAIFCKNGAQAGSNNSGS
F                     ┆        ┆ ┆   ┆         ┆       ┆
                      E        N    D          [A]

B                     E        N    D          [A]

400*
L2   VSFDGEGVVFFSSNVAAGKGGAIYAKKLSVANCGPVQFLRNIANDGGAIYLGESGELSL
F                                        ┆ ┆
                                         L G
B                                        ┆ ┆
                                         L G

L2   SADYGDIIFDGNLKRTAKENAADVNGVTVSSQAISMGSGGKITTLRAKAGHQILFNDPIE
F          ┆
           M
B          ┆
           M
              500*                              EcoRI- I
L2   MANGNNQPAQSSKLLKINDGEGYTGDIVFANGSSTLYQNVTIEQGRIVLREKAKLSVNSL
F            ┆┆                              ┆
             EP                              N
B            ┆┆                              ┆
             EP                              N
```

FIG. 6A

```
L2   SQTGGSLYMEAGSTWDFVTPQPPQQPPAANQ ITLSNLHLSLSSLLANNAVTNPPTNP
F              V                  I              I
B              L                  S

600*
L2   PAQDSHPAVIGSTTAGSVTISGPIFFEDLDDTAYDRYDWLGSNQKINVLKLQLGTKPPA
F          P         F                      D         Q S
B                                            D         Q S

700*
L2   NAPSDLTLGNEMPKYGYQGSWKLAWDPNTANNGPYTLKATWTKTGYNPGPERVASLV
F
B

L2   PNSLWGSILDIRSAHSAIQASVDGRSYCRGLWVSGVSNFFYHDRDALGQGYRYISGGYS
F                                         S
B

800*
L2   LGANSYFGSSMFGLAFTEVFGRSKDYVVCRSNHHACIGSVYLSTQQALCGSYLFGDAFI
F                                   K              I
B                                   K              V

L2   RASYGFGNQHMKTSYTFAEESDVRWDNNCLAGEIGAGLPIVITPSKLYLNELRPFVQAEF
F                                 C   V  V     I
B                                 C   V  V     I

900*
L2   SYADHESFTEEGDQARAFKSGHLLNLSVPVGVKFDRCSSTHPNKYSFMAAYICDAYRTI
F                        R  M                              G
B                        R  M                              G

1000*
L2   SGTETTLLSHQETWTTDAFHLARHGVVVRGSMYASLTSNIEVYGHGRYEYRDASRGYGL
F       Q                  I                          T
B       Q                  I                          T

1013*
L2   SAGSRVRF
F        K
B        K
```

FIG. 6B

CHLAMYDIA PROTEIN, SEQUENCE AND USES THEREOF

This application is a continuation of 08/942,596, filed Oct. 02, 1997, U.S. Pat. No. 7,459,524.

1. FIELD OF THE INVENTION

The present invention generally relates to a high molecular weight ("HMW") protein of *Chlamydia*, the amino acid sequence thereof, and antibodies, including cytotoxic antibodies, that specifically bind the HMW protein. The invention further encompasses prophylactic and therapeutic compositions comprising the HMW protein, a fragment thereof, or an antibody that specifically binds the HMW protein or a portion thereof or the nucleotide sequence encoding the HMW protein or a fragment thereof, including vaccines. The invention additionally provides methods of preventing, treating or ameliorating disorders in mammals and birds related to *Chlamydia* infections and for inducing immune responses to *Chlamydia*. The invention further provides isolated nucleotide sequences and degenerate sequences encoding the HMW protein, vectors having said sequences, and host cells containing said vectors. Diagnostic methods and kits are also included.

2. BACKGROUND OF THE INVENTION

*Chlamydia* are prevalent human pathogens causing disorders such as sexually transmitted diseases, respiratory diseases including pneumonia, neonatal conjunctivitis, and blindness. *Chlamydia* are obligate intracellular bacteria that infect the epithelial lining of the lung, conjunctivae or genital tract. The most common species of *Chlamydia* include *Chlamydia trachomatis*, *Chlamydia psittaci*, *Chlamydia pecorum* and *Chlamydia pneumoniae*. Recently, the newly designated species of *Chlamydia*, *C. pneumoniae* (formerly *C. trachomatis* TWAR), has been implicated as a major cause of epidemic human pneumonitis and perhaps may play a role in atherosclerosis.

There are currently 18 recognized *C. trachomatis* serovars, causing trachoma and a broad spectrum of sexually transmitted diseases: with the A, B and C serovars being most frequently associated with trachoma, while the D-K serovars are the most common cause of genital infections.

*C. trachomatis* is the major cause of sexually transmitted disease in many industrialized countries, including the United States. While the exact incidence of *C. trachomatis* infection in the U.S. is not known, current epidemiological studies indicate that more than 4 million chlamydial infections occur each year, compared to an estimated 2 million gonococcal infections. While all racial, ethnic and socioeconomic groups are affected, the greatest prevalence of chlamydial infections occur among young, 12 to 20 year-old, sexually active individuals. Most genitourinary chlamydial infections are clinically asymptomatic. Prolonged carriage in both men and women is common. As many as 25% of men and 75% of women diagnosed as having chlamydial infections have no overt signs of infection. As a consequence, these asymptomatic individuals constitute a large reservoir that can sustain transmission of the agent within the community.

Far from being benign, serious disease can develop from these infections including: urethritis, lymphogranuloma venereum (LGV), cervicitis, and epididymitis in males. Ascending infections from the endocervix commonly gives rise to endometritis, pelvic inflammatory disease (PID) and salpingitis which can cause tubal occlusion and lead ultimately to infertility.

*C. trachomatis* infection of neonates results from perinatal exposure to the mother's infected cervix. Nearly 70% of neonates born vaginally to mothers with chlamydial cervicitis become infected during delivery. The mucus membranes of the eye, oropharynx, urogenital tract and rectum are the primary sites of infection. Chlamydial conjunctivitis has become the most common form of ophthalmia neonatorum. Approximately 20-30% of exposed infants develop inclusion conjunctivitis within 14 days of delivery even after receiving prophylaxis with either silver nitrate or antibiotic ointment. *C. trachomatis* is also the leading cause of infant pneumonia in the United States. Nearly 10-20% of neonates delivered through an infected cervix will develop chlamydial pneumonia and require some type of medical intervention.

In developing countries, ocular infections of *C. trachomatis* cause trachoma, a chronic follicular conjunctivitis where repeated scar formation leads to distortion of the eyelids and eventual loss of sight. Trachoma is the world's leading cause of preventable blindness. The World Health Organization estimates that over 500 million people worldwide, including about 150 million children, currently suffer from active trachoma and over 6 million people have been blinded by this disease.

In industrialized countries, the costs associated with treating chlamydial infections are enormous. In the U.S., the annual cost of treating these diseases was estimated at $2.5-3 billion in 1992 and has been projected to exceed $8 billion by the year 2000.

One potential solution to this health crisis would be an effective chlamydial vaccine. Several lines of evidence suggest that developing an effective vaccine is feasible.

Studies in both humans and primates have shown that short-term protective immunity to *C. trachomatis* can be produced by vaccinating with whole *Chlamydia*. However, protection was characterized as short lived, serovar specific, and due to mucosal antibody. Additionally, in some vaccinees disease was exacerbated when these individuals became naturally infected with a serovar different from that used for immunization. This adverse reaction was ultimately demonstrated to be due to a delayed-type hypersensitivity response. Thus, the need exists to develop a subunit-based chlamydial vaccine capable of producing an efficacious but nonsensitizing immune response. Such a subunit vaccine may need to elicit both mucosal neutralizing secretory IgA antibody and/or cellular immune response to be efficacious.

Subunit vaccine development efforts to date have focused almost exclusively on the major outer membrane protein (MOMP). MOMP is an integral membrane protein of approximately 40 kDa in size and comprises up to about 60% of the infectious elementary body (EB) membrane protein (Caldwell, H. D., J. Kromhout, and L. Schachter. 1981. *Infect. Immun.*, 31:1161-1176). MOMP imparts structural integrity to the extracellular EB and is thought to function as a porin-like molecule when the organism is growing intracellularly and is metabolically active. With the exception of four surface exposed variable domains (VDI-VDIV), MOMP is highly conserved among all 18 serovars. MOMP is highly immunogenic and can elicit a local neutralizing anti-*Chlamydia* antibody. However, problems exists with this approach.

To date, most MOMP-specific neutralizing epitopes that have been mapped are located within the VD regions and thus give rise only to serovar-specific antibody. Attempts to combine serovar-specific epitopes in various vaccine vectors (e.g. poliovirus) to generate broadly cross-reactive neutralizing antibodies have been only marginally successful (Murdin, A. D., H. Su, D. S. Manning, M. H. Klein, M. J. Parnell, and H.

D. Caldwell. 1993. *Infect. Immun.*, 61:4406-4414; Murdin, A. D., H. Su, M. H. Klein, and H. D. Caldwell. 1995. *Infect. Immun.*, 63:1116-1121).

Two other major outer membrane proteins in *C. trachomatis*, the 60 kDa and 12 kDa cysteine-rich proteins, as well as the surface-exposed lipopolysaccharide, are highly immunogenic but, unlike MOMP, have not been shown to induce a neutralizing antibody (Cerrone et al., 1991, *Infect. Immun.*, 59:79-90). Therefore, there remains a need for a novel subunit-based chlamydial vaccine.

SUMMARY OF THE INVENTION

An object of the present invention is to provide an isolated and substantially purified high molecular weight protein of a *Chlamydia* sp. ("HMW protein"), wherein the HMW protein has an apparent molecular weight of about 105-115 kDa, as determined by SDS-PAGE, or a fragment or analogue thereof. Preferably the HMW protein has substantially the amino acid sequence of any of SEQ ID Nos.: 2, 15 and 16. Preferred fragments of the HMW protein include SEQ ID Nos: 3, 17, and 25-37. As used herein, "substantially the sequence" is intended to mean that the sequence is at least 80%, more preferably at least 90% and most preferably at least 95% identical to the referenced sequence. Preferably, the HMW protein is an outer membrane protein. More preferably, the outer membrane HMW protein is surface localized. Preferably, the HMW protein has a heparin binding domain. Preferably, the HMW Protein has a porin-like domain. It is intended that all species of *Chlamydia* are included in this invention, however preferred species include *Chlamydia trachomatis, Chlamydia psittaci, Chlamydia percorum* and *Chlamydia pneumoniae*. The substantially purified HMW protein is at least 70 wt % pure, preferably at least about 90 wt % pure, and may be in the form of an aqueous solution thereof.

Also included in this invention are recombinant forms of the HMW protein, wherein in transformed *E. coli* cells, the expressed recombinant form of the HMW protein has an apparent molecular weight of about 105-115 kDa, as determined by SDS-PAGE, or a fragment or analogue thereof. The term HMW-derived polypeptide is intended to include fragments of the HMW protein; variants of wild-type HMW protein or fragment thereof, containing one or more amino acid deletions, insertions or substitutions; and chimeric proteins comprising a heterologous polypeptide fused to the C-terminal or N-terminal or internal segment of a whole or a portion of the HMW protein.

As used herein and in the claims, the term "HMW protein" refers to a native purified or recombinant purified high molecular weight protein of a species of *Chlamydia* wherein the apparent molecular weight (as determined by SDS-PAGE) is about 105-115 kDa. As used herein and in the claims, the term "rHMW protein" refers to recombinant HMW protein.

Another object of the present invention is to provide an isolated substantially pure nucleic acid molecule encoding a HMW protein or a fragment or an analogue thereof. Preferred is the nucleic acid sequence wherein the encoded HMW protein comprises the amino acid sequence of any of SEQ ID Nos.: 2, 15 and 16, or a fragment thereof, particularly SEQ ID Nos.: 3, 17, 25-37. Also included is an isolated nucleic acid molecule comprising a DNA sequence of any of SEQ ID Nos.: 1, 23-24 or a complementary sequence thereof; a fragment of the HMW DNA sequence having the nucleic acid sequence of any of SEQ ID Nos.: 4-14, 18-22 or the complimentary sequence thereto; and a nucleic acid sequence which hybridizes under stringent conditions to any one of the sequences described above. The nucleic acid that hybridizes under stringent condition preferably has a sequence identity of about 70% with any of the sequences identified above, more preferably about 90%.

The production and use of derivatives and analogues of the HMW protein are within the scope of the present invention. In a specific embodiment, the derivative or analogue is functionally active, i.e., capable of exhibiting one or more functional activities associated with a full-length, wild-type HMW protein. As one example, such derivatives or analogues which have the desired immunogenicity or antigenicity can be used, for example, in immunoassays, for immunization, etc. A specific embodiment relates to a HMW fragment that can be bound by an anti-HMW antibody. Derivatives or analogues of HMW can be tested for the desired activity by procedures known in the art.

In particular, HMW derivatives can be made by altering HMW sequences by substitutions, additions or deletions that provide for functionally equivalent molecules. Due to the degeneracy of nucleotide coding sequences, other DNA sequences which encode substantially the same amino acid sequence as a HMW gene may be used in the practice of the present invention. These include but are not limited to nucleotide sequences comprising all or portions of genes which are altered by the substitution of different codons that encode a functionally equivalent amino acid residue within the sequence, thus producing a silent change. Likewise, the HMW derivatives of the invention include, but are not limited to, those containing, as a primary amino acid sequence, all or part of the amino acid sequence of a HMW protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In, a specific embodiment of the invention, proteins consisting of or comprising a fragment of a HMW protein consisting of at least 6 (continuous) amino acids of the HMW protein is provided. In other embodiments, the fragment consists of at least 7 to 50 amino acids of the HMW protein. In specific embodiments, such fragments are not larger than 35, 100 or 200 amino acids. Derivatives or analogues of HMW include but are not limited to those molecules comprising regions that are substantially homologous to HMW or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding HMW sequence, under stringent, moderately stringent, or nonstringent conditions.

The HMW derivatives and analogues of the invention can be produced by various methods known in the art. The manipulations which result in their production can occur at the gene or protein level. For example, the cloned HMW gene sequence can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analogue of HMW, care should be taken to ensure that the modified gene remains within the same translational reading frame as HMW, uninterrupted by translational stop signals, in the gene region where the desired HMW activity is encoded.

Additionally, the HMW-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the HMW sequence may also be made at the protein level. Included within the scope of the invention are HMW protein fragments or other derivatives or analogues which are differentially modified during or after translation, e.g., by glycosylation, lipidation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogues and derivatives of HMW can be chemically synthesized. For example, a peptide corresponding to a portion of a HMW protein which comprises the desired domain, or which mediates the desired activity in vitro, can be synthesized by use of a peptide synthesizer. Furthermore, if desired, nonclassical amino acids or chemical amino acid analogues can be introduced as a substitution or addition into the HMW sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

Another object of the invention is to provide a recombinant expression vector adapted for transformation of a host or for delivery of a HMW protein to a host comprising the nucleic acid molecule of SEQ ID No.: 1, 23 or 24 or any fragment thereof. Preferably, the recombinant expression vector is adapted for transformation of a host and comprises an expression means operatively coupled to the nucleic acid molecule for expression by the host of said HMW protein or the fragment or analogue thereof. More preferred is the expression vector wherein the expression means includes a nucleic acid portion encoding a leader sequence for secretion from the host or an affinity domain coupled to either the N-or C-terminus of the protein or the fragment or analogue thereof.

A further aspect of the invention includes a transformed host cell containing an expression vector described above and the recombinant HMW protein or fragment or analogue thereof producible by the transformed host cell.

Still a further aspect of the invention is directed to a HMW protein recognizable by an antibody preparation that specifically binds to a peptide having the amino acid sequence of SEQ ID No. 2, 15-16 or a fragment or conservatively substituted analogue thereof.

Antigenic and/or immunogenic compositions are another aspect of the invention wherein the compositions comprise at least one component selected from the following group:
  a) a HMW protein, wherein the molecular weight is about 105-115 kDa, as determined by SDS-PAGE, or a fragment or analogue thereof;
  b) an isolated nucleic acid molecule encoding a HMW protein, or a fragment or analogue thereof;
  c) an isolated nucleic acid molecule having the sequence of SEQ ID Nos. 1, 22, 23 or 24, the complimentary sequence thereto or a nucleic acid sequence which hybridizes under stringent conditions thereto or fragment thereof;
  d) an isolated recombinant HMW protein, or fragment or analogue thereof, producible in a transformed host comprising an expression vector comprising a nucleic acid molecule as defined in b) or c) and expression means operatively coupled to the nucleic acid molecule for expression by the host of said HMW protein or the fragment or analogue thereof;
  e) a recombinant vector comprising a nucleic acid encoding a HMW protein or fragment or analogue thereof;
  f) a transformed cell comprising the vector of e) and optionally an adjuvant, and a pharmaceutically acceptable carrier or diluent therefor, said composition producing an immune response when administered to a host.

Preferred adjuvants include cholera holotoxin or subunits, E. coli heat labile holotoxin, subunits and mutant forms thereof, alum, QS21, and MPL. Particularly, preferred are alum, LTR192G, mLT and QS21.

Also included are methods for producing an immune response in a mammal or a bird comprising administering to said mammal, an effective amount of the antigenic or the immunogenic composition described above.

Another aspect of the invention is directed to antisera raised against the antigenic or immunogenic composition of the invention, and antibodies present in the antisera that specifically bind a HMW protein or a fragment or analogue thereof. Preferably the antibodies bind a HMW protein having the amino acid sequence of SEQ ID Nos.: 2, 15-16 or fragment or a conservatively substituted analogue thereof. Also included are monoclonal antibodies that specifically bind a HMW protein or a fragment or analogue thereof.

A further aspect of the invention includes pharmaceutical and vaccine compositions comprising an effective amount of at least one component selected from the following group:
  a) a HMW protein, wherein the isolated protein molecular weight is about 105-115 kDa, as determined by SDS-PAGE, or a fragment or analogue thereof;
  b) an isolated nucleic acid molecule encoding a HMW protein, or a fragment or analogue thereof;
  c) an isolated nucleic acid molecule having the sequence of SEQ ID Nos.: 1, 22, 23 or 24 the complimentary sequence thereto or a nucleic acid sequence which hybridizes under stringent conditions thereto or a fragment thereof;

d) an isolated recombinant HMW protein, or fragment or analogue thereof producible in a transformed host comprising an expression vector comprising a nucleic acid molecule as defined in b) or c) and expression means operatively coupled to the nucleic acid molecule for expression by the host of said HMW protein of a *Chlamydia* species or the fragment or analogue thereof;

e) a recombinant vector, comprising a nucleic acid encoding a HMW protein or fragment or analogue thereof;

f) a transformed cell comprising the vector of e), g) antibodies that specifically bind the component of a), b), c), d) or e), and a pharmaceutically acceptable carrier or diluent therefor referred are vaccine compositions which are effective at the mucosal level.

The invention also includes a diagnostic reagent which may include any one or more of the above mentioned aspects, such as the native HMW protein, the recombinant HMW protein, the nucleic acid molecule, the immunogenic composition, the antigenic composition, the antisera, the antibodies, the vector comprising the nucleic acid, and the transformed cell comprising the vector.

Methods and diagnostic kits for detecting *Chlamydia* or anti-*Chlamydia* antibodies in a test sample are also included, wherein the methods comprise the steps of:

a) contacting said sample with an antigenic composition comprising *Chlamydia* HMW protein or a fragment or analogue thereof or immunogenic composition or antibodies thereto to form *Chlamydia* antigen: anti-*Chlamydia* antibody immunocomplexes, and further, b) detecting the presence of or measuring the amount of said immunocomplexes formed during step a) as an indication of the presence of said *Chlamydia* or anti-*Chlamydia* antibodies in the test sample.

The diagnostic kits for detecting *Chlamydia* or antibodies thereto comprise antibodies, or an antigenic or immunogenic composition comprising *Chlamydia* HMW protein or a fragment or analogue thereof, a container means for contacting said antibodies or composition with a test sample suspected of having anti-*Chlamydia* antibodies or *Chlamydia* and reagent means for detecting or measuring *Chlamydia* antigen: anti-*Chlamydia* antibody immunocomplexes formed between said antigenic or immunogenic composition or said antibodies and said test sample.

A further aspect of the present invention provides methods for determining the presence of nucleic acids encoding a HMW protein or a fragment or analogue thereof in a test sample, comprising the steps of:

a) contacting the test sample with the nucleic acid molecule provided herein to produce duplexes comprising the nucleic acid molecule and any said nucleic acid molecule encoding the HMW protein in the test sample and specifically hybridizable therewith; and b) determining the production of duplexes.

The present invention also provides a diagnostic kit and reagents therefor, for determining the presence of nucleic acid encoding a HMW protein or fragment or analogue thereof in a sample, comprising:

a) the nucleic acid molecule as provided herein;

b) means for contacting the nucleic acid with the test sample to produce duplexes comprising the nucleic acid molecule and any said nucleic acid molecule encoding the HMW protein in the test sample and specifically hybridizable therewith; and c) means for determining the production of duplexes.

Also included in this invention are methods of preventing, treating or ameliorating disorders related to *Chlamydia* in an animal including mammals and birds in need of such treatment comprising administering an effective amount of the pharmaceutical or vaccine composition of the invention. Preferred disorders include a *Chlamydia* bacterial infection, trachoma, conjunctivitis, urethritis, lymphogranuloma venereum (LGV), cervicitis, epididymitis, or endometritis, pelvic inflammatory disease (PID), salpingitis, tubal occlusion, infertility, cervical cancer, and artherosolerosis. Preferred vaccine or pharmaceutical compositions include those formulated for in vivo administration to a host to confer protection against disease or treatment therefor caused by a species of *Chlamydia*. Also preferred are compositions formulated as a microparticle, capsule, liposome preparation or emulsion.

ABBREVIATIONS anti-HMW=HMW polypeptide antibody or antiserum
ATCC=American Type Culture Collection
immuno-reactive=capable of provoking a cellular or humoral immune response
kDa=kilodaltons
OG=n-octyl β-D-glucopyranoside or octyl glucoside
OMP=outer membrane protein
OMPs=outer membrane proteins
PBS=phosphate buffered saline
PAGE=polyacrylamide gel electrophoresis
polypeptide=a peptide of any length, preferably one having ten or more amino acid residues
SDS=sodium dodecylsulfate
SDS-PAGE=sodium dodecylsulfate polyacrylamide gel electrophoresis Nucleotide or nucleic acid sequences defined herein are represented by one-letter symbols for the bases as follows:
A (adenine)
C (cytosine)
G (guanine)
T (thymine)
U (uracil)
M (A or C)
R (A or G)
W (A or T/U)
S (C or G)
Y (C or T/U)
K (G or T/U)
V (A or C or G; not T/U)
H (A or C or T/U; not G)
D (A or G or T/U; not C)
B (C or G or T/U; not A)
N (A or C or G or T/U) or (unknown)

Peptide and polypeptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)

H (histidine)
I (isoleucine)
L (leucine)
K (lysine)
M (methionine)
F (phenylalanine)
P (proline)
S (serine)
T (threonine)
W (tryptophan).
Y (tyrosine.)
V (valine)
X (unknown)

The present invention may be more fully understood by reference to the following detailed description of the invention, non-limiting examples of specific embodiments of the invention and the appended figures.

BRIEF DESCRIPTION OF THE FIGURES

FIG. 2A-C. Consensus Nucleic Acid Sequence encoding the open reading frame of the HMW protein from C. trachoamtis LGV $L_2$ (SEQ ID NO.: 1).

FIG. 3. Deduced Amino Acid Sequence of the HMW protein from the PCR open reading frame from C. trachomatis LGV $L_2$ (SEQ ID NO.: 2).

FIG. 6A-B. Predicted amino acid sequences of HMW Protein for C. trachomatis $L_2$, B, and F. The C. trachomatis $L_2$ sequence (SEQ ID NO: 43) is given in the top line and begins with the first residue of the mature protein, E (see amino acid residues 29-1012 of SEQ ID NO: 2). Potential eucaryotic N-glycosylation sequences are underlined. A hydrophobic helical region flanked by proline rich segments and of suitable length to span the lipid bilayer is underlined and enclosed in brackets. Amino acid differences identified in the B (see amino acid residues 29-1013 of SEQ ID NO: 15) and F (see amino acid residues 29-1013 of SEQ ID NO: 16) serovars are designated below the $L_2$ HMWP protein sequence.

DETAILED DESCRIPTION OF THE INVENTION

Figure 1:
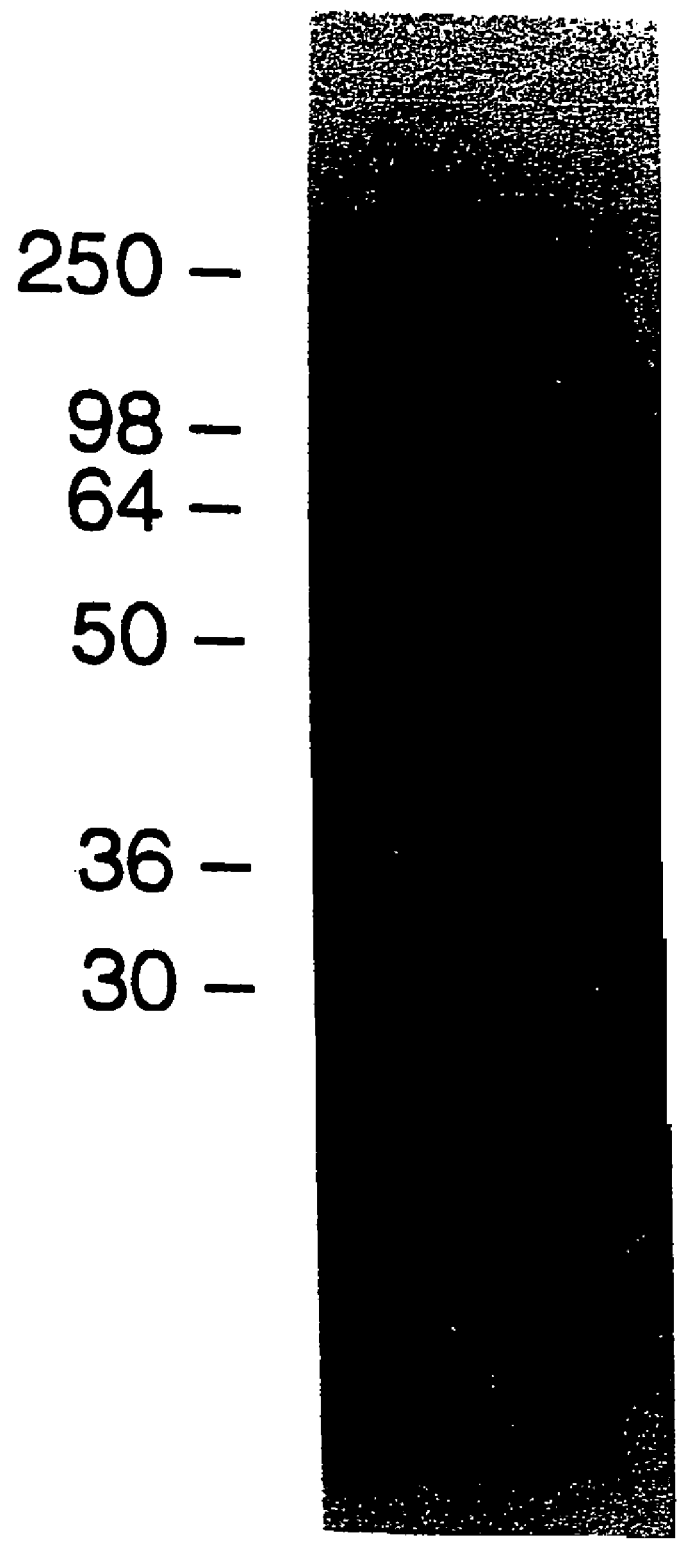
FIG. 1: Western blot analysis of C. trachomatis $L_2$ elementary bodies (EBs).
  Gradient purified EBs were solubilized in standard Laemmli SDS-PAGE sample buffer containing 2-mercaptoethanol, boiled for ⁻3 minutes and loaded onto a 4-12% Tris-glycine gradient gel containing SDS and electrophoresed at 100V. Immediately following electrophoresis, proteins were electroblotted onto PVDF membranes at 4° C. for ⁻2.5 hours at ⁻50V. The blocked membrane was probed using a 1/5,000 dilution of anti-rHMWP' antibody (K196) for 1.5 hours at room temperature. Following washing, the membrane was treated with a 1/5,000 dilution of a goat anti-rabbit IgG antibody conjugated to HRP for 1 hour at room temperature. The blot was developed using a standard TMB substrate system.
  Three immunoreactive bands detected in EBs and RBs.
  Dot indicates HMW Protein of about 105-115 kDa.

The term "antigens" and its related term "antigenic" as used herein and in the claims refers to a substance that binds specifically to an antibody or T-cell receptor. Preferably said antigens are immunogenic.

The term "immunogenic" as used herein and in the claims refers to the ability to induce an immune response, e.g., an antibody and/or a cellular immune response in a an animal, preferably a mammal or a bird.

The term "host" as used herein and in the claims refers to either in vivo in an animal or in vitro in mammalian cell cultures.

An effective amount of the antigenic, immunogenic, pharmaceutical, including, but not limited to vaccine, composition of the invention should be administered, in which "effective amount" is defined as an amount that is sufficient to produce a desired prophylactic, therapeutic or ameliorative response in a subject, including but not limited to an immune response. The amount needed will vary depending upon the immunogenicity of the HMW protein, fragment, nucleic acid or derivative used, and the species and weight of the subject to be administered, but may be ascertained using standard techniques. The composition elicits an immune response in a subject which produces antibodies, including anti-HMW protein antibodies and antibodies that are opsonizing or bactericidal. In preferred, non-limiting, embodiments of the invention, an effective amount of a composition of the invention produces an elevation of antibody titer to at least three times the antibody titer prior to administration. In a preferred, specific, non-limiting embodiment of the invention, approximately 0.01 to 2000 μg and preferably 0.1 to 500 μg are administered to a host. Preferred are compositions additionally comprising an adjuvant.

Immunogenic, antigenic, pharmaceutical and vaccine compositions may be prepared as injectables, as liquid solutions or emulsions. The HMW protein may be mixed with one or more pharmaceutically acceptable excipient which is compatible with the HMW protein. Such excipients may include, water, saline, dextrose, glycerol, ethanol, and combinations thereof.

Immunogenic, antigenic, pharmaceutical and vaccine compositions may further contain one or more auxiliary substance, such as wetting or emulsifying agents, pH buffering agents, or adjuvants to enhance the effectiveness thereof. Immunogenic, antigenic, pharmaceutical and vaccine compositions may be administered parenterally, by injection, subcutaneously or intramuscularly.

Alternatively, the immunogenic, antigenic, pharmaceutical and vaccine compositions formed according to the present invention, may be formulated and delivered in a manner to evoke an immune response at mucosal surfaces. Thus, the immunogenic, antigenic, pharmaceutical and vaccine compositions may be administered to mucosal surfaces by, for example, the nasal, oral (intragastric), ocular, branchiolar, intravaginal or intrarectal routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 0.001 to 95% of the HMW protein. The immunogenic, antigenic, pharmaceutical and vaccine compositions are-administered in a manner compatible with the dosage formulation, and in such amount as will be therapeutically effective, protective or immunogenic.

Further, the immunogenic, antigenic, pharmaceutical and vaccine compositions may be used in combination with or conjugated to one or more targeting molecules for delivery to specific cells of the immune system, such as the mucosal surface. Some examples include but are not limited to vitamin B12, bacterial toxins or fragments thereof, monoclonal antibodies and other specific targeting lipids, proteins, nucleic acids or carbohydrates.

The quantity to be administered depends on the subject to be treated, including, for example, the capacity of the individual's immune system to synthesize antibodies, and if needed, to produce a cell-mediated-immune response. Precise amounts of active ingredient required to be administered depend on the judgment of the practitioner. However, suitable dosage ranges are readily determinable by one skilled in the art and may be of the order of 0.1 to 1000 micrograms of the HMW protein, fragment or analogue thereof. Suitable regimes for initial administration and booster doses are also variable, but may include an initial administration followed by subsequent administrations. The dose may also depend on the route(s) of administration and will vary according to the size of the host.

The concentration of the HMW protein in an antigenic, immunogenic or pharmaceutical composition according to the invention is in general about 0.001 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The antigenic, immunogenic or pharmaceutical preparations, including vaccines, may comprise as the immunostimulating material a nucleotide vector comprising at least a portion of the gene encoding the HMW protein, or the at least a portion of the gene may be used directly for immunization.

To efficiently induce humoral immune responses (HIR) and cell-mediated immunity (CMI), immunogens are typically emulsified in adjuvants. Immunogenicity can be significantly improved if the immunogen is co-administered with an adjuvant. Adjuvants may act by retaining the immunogen locally near the site of administration to produce a depot effect facilitating a slow, sustained release of antigen to cells of the immune system. Adjuvants can also attract cells of the immune system to an immunogen depot and stimulate such cells to elicit immune responses.

Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP), Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit either CMI or HIR or both to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum.

Other extrinsic adjuvants may include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

International Patent Application, PCT/US95/09005 incorporated herein by reference describes mutated forms of heat labile toxin of enterotoxigenic E. coli ("mLT"). U.S. Pat. No. 5,057,540, incorporated herein by reference, describes the adjuvant, Qs21, an HPLC purified non-toxic fraction of a saponin from the bark of the South American tree *Quiliaja saponaria* molina 3D-MPL is described in great Britain Patent 2,220,211, and is incorporated herein by reference.

U.S. Pat. No. 4,855,283 granted to Lockhoff et al on Aug. 8, 1989 which is incorporated herein by reference, teaches glycolipid analogues including N-glycosylamides, N-glycosylureas and N-glycosylcarbamates, each of which is substituted in the sugar residue by an amino acid, as immunomodulators or adjuvants. Lockhoff reported that N-glycosphospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Lipidation of synthetic peptides has also been used to increase their immunogenicity.

Therefore, according to the invention, the immunogenic, antigenic, pharmaceutical, including vaccine, compositions comprising a HMW protein, or a fragment or derivative thereof or a HMW encoding nucleic acid or fragment thereof or vector expressing the same, may further comprise an adjuvant, such as, but not limited to alum, mLT, QS21 and all those listed above. Preferably, the adjuvant is selected from alum, LT, 3D-mPL, or Bacille Calmette-Guerine (BCG) and mutated or modified forms of the above, particularly mLT and LTR192G. The compositions of the present invention may also further comprise a suitable pharmaceutical carrier, including but not limited to saline, bicarbonate, dextrose or other aqueous solution. Other suitable pharmaceutical carriers are described in *Remington's Pharmaceutical Sciences*, Mack Publishing Company, a standard reference text in this field, which is incorporated herein by reference in its entirety.

Immunogenic, antigenic and pharmaceutical, including vaccine, compositions may be administered in a suitable, nontoxic pharmaceutical carrier, may be comprised in microcapsules, and/or may be comprised in a sustained release implant.

Immunogenic, antigenic and pharmaceutical, including vaccine, compositions may desirably be administered at several intervals in order to sustain antibody levels, and/or may be used in conjunction with other bacteriocidal or bacteriostatic methods.

As used herein and in the claims, "antibodies" of the invention may be obtained by any conventional methods known to those skilled in the art, such as but not limited to the methods described in *Antibodies A Laboratory Manual* (E. Harlow, D. Lane, Cold Spring Harbor Laboratory Press, 1989) which is incorporated herein by reference in its entirety. The term "antibodies" is intended to include all forms, such as but not limited to polyclonal, monoclonal, purified IgG, IgM, IgA and fragments thereof, including but not limited to fragments such as Fv, single chain Fv (scFv), F(ab')$_2$'. Fab fragments (Harlow and Leon, 1988, Antibody, Cold Spring Harbor); single chain antibodies (U.S. Pat. No. 4,946,773) 0.25 chimeric or humanized antibodies (Morrison et al., 1984, Proc. Nat'l Acad. Sci. USA 81:6851); Neuberger et al., 1981, Nature 81:6851) and complementary determining regions (CDR), (see Verhoeyen and Windust, in Molecular Immunology 2ed., by B. D. Hames and D. M. Glover, IRL Press, Oxoford University Press, 1996, at pp. 283-325), etc.

In general, an animal (a wide range of vertebrate species can be used, the most common being mice, rats, guinea pig, bovine, pig, hamsters, sheep, birds and rabbits) is immunized with the HMW protein or nucleic acid sequence or immunogenic fragment or derivative thereof of the present invention in the absence or presence of an adjuvant or any agent that enhances the immunogen's effectiveness and boosted at regular intervals. The animal serum is assayed for the presence of desired antibody by any convenient method. The serum or blood of said animal can be used as the source of polyclonal antibodies.

For monoclonal antibodies, animals are treated as described above. When an acceptable antibody titre is detected, the animal is euthanized and the spleen is aseptically removed for fusion. The spleen cells are mixed with a specifically selected immortal myeloma cell line, and the mixture is then exposed to an agent, typically polyethylene glycol or the like, which promotes the fusion of cells. Under these circumstances fusion takes place in a random selection and a fused cell mixture together with unfused cells of each type is the resulting product. The myeloma cell lines that are used for fusion are specifically chosen such that, by the use of selection media, such as HAT: hypoxanthine, aminopterin, and thymidine, the only cells to persist in culture from the fusion mixture are those that are hybrids between cells derived from the immunized donor and the myeloma cells. After fusion, the cells are diluted and cultured in the selective media. The culture media is screened for the presence of antibody having desired specificity towards the chosen antigen. Those cultures containing the antibody of choice are cloned by limiting dilution until it can be adduced that the cell culture is single cell in origin.

Antigens, Immunogens and Immunoassays

The HMW protein or nucleic acid encoding same, and fragments thereof are useful as an antigen or immunogen for the generation of anti-HMW protein antibodies or as an antigen in immunoassays including enzyme-linked immunosorbent assays (ELISA), radioimmmunoassays (RIA) and other non-enzyme linked antibody binding assays or procedures known in the art for the detection of anti-bacterial, anti-*Chlamydia*, and anti-HMW protein antibodies. In ELISA assays, the HMW protein is immobilized onto a selected surface, for example, a surface capable of binding proteins such as the wells of a polystyrene microtiter plate. After washing to remove incompletely absorbed HMW protein, a nonspecific protein solution that is known to be antigenically neutral with regard to the test sample may be bound to the selected surface. This allows for blocking of nonspecific absorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of bovine gamma globulin (BGG) and/or phosphate buffered saline (PBS)/Tween. The sample is then allowed to incubate for from 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound HMW protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG.

To provide detecting means, the second antibody may have an associated activity such as an enzymatic activity that will generate, for example, a color development upon incubating with an appropriate chromogenic substrate. Detection may then be achieved by detecting color generation. Quantification may then be achieved by measuring the degree of color generation using, for example, a visible spectrophotometer and comparing to an appropriate standard. Any other detecting means known to those skilled in the art are included.

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit may comprise HMW protein or nucleic acid encoding same or fragment thereof, a monoclonal or polyclonal antibody of the present invention in combination with several conventional kit components. Conventional kit components will be readily apparent to those skilled in the art and are disclosed in numerous publications, including *Antibodies A Laboratory Manual* (E. Harlow, D.

Lane, Cold Spring Harbor Laboratory Press, 1989) which is incorporated herein by reference in its entirety. Conventional kit components may include such items as, for example, microtitre plates, buffers to maintain the pH of the assay mixture (such as, but not limited to Tris, HEPES, etc.), conjugated second antibodies, such as peroxidase conjugated anti-mouse IgG (or any anti-IgG to the animal from which the first antibody was derived) and the like, and other standard reagents.

Nucleic Acids and Uses Thereof

The nucleotide sequences of the present invention, including DNA and RNA and comprising a sequence encoding the HMW protein or a fragment or analogue thereof, may be synthesized using methods known in the art, such as using conventional chemical approaches or polymerase chain reaction (PCR) amplification using convenient pairs of oligonucleotide primers and ligase chain reaction using a battery of contiguous oligonucleotides. The sequences also allow for the identification and cloning of the HMW protein gene from any species of *Chlamydia*, for instance for screening chlamydial genomic libraries or expression libraries.

The nucleotide sequences encoding the HMW protein of the present invention are useful for their ability to selectively form duplex molecules with complementary stretches of other protein genes. Depending on the application, a variety of hybridization conditions may be employed to achieve varying sequence identities. In specific aspects, nucleic acids are provided which comprise a sequence complementary to at least 10, 15, 25, 50, 100, 200 or 250 nucleotides of the HMW protein gene (FIG. 2A-C). In specific embodiments, nucleic acids which hybridize to an HMW protein nucleic acid (e.g. having sequence SEQ ID NO: 1, 23 or 24) under annealing conditions of low, moderate or high stringency conditions.

For a high degree of selectivity, relatively stringent conditions are used to form the duplexes, such as, by way of example and not limitation, low salt and/or high temperature conditions, such as provided by 0.02 M to 0.15 M NaCl at temperatures of between about 50° C. to 70° C. For some applications, less stringent hybridization conditions are required, by way of example and not limitation such a 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. By way of example and not limitation, in general, convenient hybridization temperatures in the presence of 50% formamide are: 42° C. for a probe which is 95 to 100% homologous to the target fragment, 37° C. for 90 to 95% homology and 32° C. for 70 to 90% homology.

Low, moderate and high stringency conditions are well known to those of skill in the art, and will vary predictably depending on the base composition and length of the particular nucleic acid sequence and on the specific organism from which the nucleic acid sequence is derived. For guidance regarding such conditions see, for example, Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. which is incorporate herein, by reference.

In the preparation of genomic libraries, DNA fragments are generated, some of which will encode parts or the whole of *Chlamydia* HMW protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, bacmids and yeast artificial chromosome (YAC). (See, for example, Sambrook et al., 1989, *Molecular Cloning*, A Laboratory Manual, 2d Ed., Cold. Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. I, II.) The genomic library may be screened by nucleic acid hybridization to labeled probe (Benton and Davis, 1977, *Science* 196: 180; Grunstein and Hogness, 1975, *Proc. Natl. Acad. Sci. U.S.A.* 72:3961).

The genomic libraries may be screened with labeled degenerate oligonucleotide probes corresponding to the amino acid sequence of any peptide of HMW protein using optimal approaches well known in the art. In particular embodiments, the screening probe is a degenerate oligonucleotide that corresponds to the sequence of SEQ ID NO: 4. In another embodiment, the screening probe may be a degenerate oligonucleotide that corresponds to the sequence of SEQ ID NO:5. In an additional embodiment, any one of the oligonucleotides of SEQ ID NOs: 6-9, 12-14 and 18-21 are used as the probe. In further embodiments, any one of the sequences of SEQ ID NOs: 1, 10-11, 22-24 or any fragments thereof, or any complement of the sequence or fragments may be used as the probe. Any probe used preferably is 15 nucleotides or longer.

Clones in libraries with insert DNA encoding the HMW protein or fragments thereof will hybridize to one or more of the degenerate oligonucleotide probes. Hybridization of such oligonucleotide probes to genomic libraries are carried out using methods known in the art. For example, hybridization with the two above-mentioned oligonucleotide probes may be carried out in 2×SSC, 1.0% SDS at 50° C. and washed using the same conditions.

In yet another aspect, clones of nucleotide sequences encoding a part or the entire HMW protein or HMW-derived polypeptides may also be obtained by screening *Chlamydia* expression libraries. For example, *Chlamydia* DNA or *Chlamydia* cDNA generated from RNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed HMW protein or HMW-derived polypeptides. In one embodiment, the various anti-HMW antibodies of the invention can be used to identify the desired clones using methods known in the art. See, for example, Harlow and Lane, 1988, *Antibodies: A Laboratory Manual*, Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes HMW protein or HMW-derived polypeptide could be detected using DYNA Beads according to Olsvick et al., 29th ICAAC, Houston, Tex. 1989, incorporated herein by reference. Anti-HMW antibodies are crosslinked to tosylated DYNA Beads M280, and these antibody-containing beads would then be used to adsorb to colonies or plaques expressing HMW protein or HMW-derived polypeptide. Colonies or plaques expressing HMW protein or HMW-derived polypeptide is identified as any of those that bind the beads.

Alternatively, the anti-HMW antibodies can be nonspecifically immobilized to a suitable support, such as silica or Celite™ resin. This material would then be used to adsorb to bacterial colonies expressing HMW protein or HMW-derived polypeptide as described in the preceding paragraph.

In another aspect, PCR amplification may be used to produce substantially pure DNA encoding a part of or the whole of HMW protein from *Chlamydia* genomic DNA. Oligonucleotide primers, degenerate or otherwise, corresponding to known HMW protein sequences can be used as primers. In particular embodiments, an oligonucleotide, degenerate or otherwise, encoding the peptide having an amino acid sequence of SEQ ID NO: 2, 3 or 15-17 or any portion thereof may be used as the 5' primer. For fragment examples, a 5' primer may be made from any one of the nucleotide sequences of SEQ ID NO: 4-7, 10, 12, 22-24 or any portion thereof. Nucleotide sequences, degenerate or otherwise, that are reverse complements of SEQ ID NO: 11, 13 or 14 may be used as the 3' primer.

PCR can be carried out, e.g., by use of a Perkin-Elmer Cetus thermal cycler and Taq polymerase (Gene Amp™). One can choose to synthesize several different degenerate primers, for use in the PCR reactions. It is also possible to vary the stringency of hybridization conditions used in priming the PCR reactions, to allow for greater or lesser degrees of nucleotide sequence similarity between the degenerate primers and the corresponding sequences in *Chlamydia* DNA. After successful amplification of a segment of the sequence encoding HMW protein, that segment may be molecularly cloned and sequenced, and utilized as a probe to isolate a complete genomic clone. This, in turn, will permit the determination of the gene's complete nucleotide sequence, the analysis of its expression, and the production of its protein product for functional analysis, as described infra.

In a clinical diagnostic embodiment, the nucleic acid sequences of the HMW protein genes of the present invention may be used in combination with an appropriate indicator means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing HMW protein gene sequences.

The nucleic acid sequences of the HMW protein genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, semen, urine, tears, mucus, bronchoalveolar lavage fluid) or even tissues, is absorbed or otherwise affixed to a selected matrix or surface. The fixed, single-stranded nucleic acid is then subjected to specific hybridization with selected probes comprising the nucleic acid sequences of the HMW protein encoding genes or fragments or analogues thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of *Chlamydia*. The selected probe may be at least 15 bp and may be in the range of about 30 to 90 bp.

Expression of the HMW Protein Gene

Plasmid vectors containing replicon and control sequences which are derived from species compatible with the host cell may be used for the expression of the genes encoding the HMW protein or fragments thereof in expression systems. Expression vectors contain all the necessary elements for the transcription and translation of the inserted protein coding sequence. The vector ordinarily carries a replication site, as well as marking sequences which are capable of providing phenotype selection in transformed cells. For example, *E. coli* may be transformed using pBR322 which contains genes for ampicillin and tetracycline resistance cells. Other commercially available vectors are useful, including but not limited to pZERO, pTrc99A, pUC19, pUC18, pKK223-3, pEXI, PCAL, pET, pSPUTK, pTrxFus, pFastBac, pThioHis, pTrcHis, pTrcHis2, and pLEx. The plasmids or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be matter of choice depending upon the desired results.

In accordance with this invention, it is preferred to make the HMW protein by recombinant methods, particularly when the naturally occurring HMW protein as isolated from a culture of a species of *Chlamydia* may include trace amounts of toxic materials or other contaminants. This problem can be avoided by using recombinantly produced HMW protein in heterologous systems which can be isolated from the host in a manner to minimize contaminants in the isolated material. Particularly desirable hosts for expression in this regard include Gram positive bacteria which do not have LPS and are, therefore endotoxin free. Such hosts include species of *Bacillus* and may be particularly useful for the production of non-pyrogenic rHMW protein, fragments or analogues thereof.

A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. Hosts that are appropriate for expression of the HMW protein genes, fragments, analogues or variants thereof, may include *E. coli*, *Bacillus* species, *Haemophilus*, fungi, yeast, such as *Saccharomyces pichia*, *Bordetella*, or the baculovirus expression system may be used. Preferably, the host cell is a bacterium, and most preferably the bacterium is *E. coli, B. subtilis* or *Salmonella*.

The expression elements of vectors vary in their strengths and specificities. Depending on the host-vector system utilized, any one of a number of suitable transcription and translation elements may be used. In a preferred embodiment, a chimeric protein comprising HMW protein or HMW-derived polypeptide sequence and a pre and/or pro sequence of the host cell is expressed. In other preferred embodiments, a chimeric protein comprising HMW protein or HMW-derived polypeptide sequence fused with, for example, an affinity purification peptide, is expressed. In further preferred embodiments, a chimeric protein comprising HMW protein or HMW-derived polypeptide sequence and a useful immunogenic peptide or protein is expressed. In preferred embodiments, HMW-derived protein expressed contains a sequence forming either an outer-surface epitope or the receptor-binding domain of native HMW protein.

Any method known in the art for inserting DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding HMW protein or HMW-derived polypeptide may be regulated by a second nucleic acid sequence so that the inserted sequence is expressed in a host transformed with the recombinant DNA molecule. For example, expression of the inserted sequence may be controlled by any promoter/enhancer element known in the art. Promoters which may be used to control expression of inserted sequences include, but are not limited to the SV40 early promoter region (Bernoist and Chambon, 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42) for expression in animal cells; the promoters of β-lactamase (Villa-Kamaroff et al., 1978, *Proc. Natl. Acad. Sci. U.S.A.* 75:3727-3731), tac (DeBoer et al., 1983, *Proc. Natl. Acad. Sci. U.S.A.* 80:21-25), $P_L$, or trc for expression in bacterial cells (see also "Useful proteins from recombinant bacteria" in Scientific American, 1980, 242:74-94); the nopaline synthetase promoter region or the cauliflower mosaic virus 35S RNA promoter (Gardner et al., 1981, *Nucl. Acids Res.* 9:2871), and the promoter of the photosynthetic enzyme ribulose biphosphate carboxylase (Herrera-Estrella et al., 1984, *Nature* 310:115-120) for expression implant cells; promoter elements from yeast or other fungi such as the Gal4 promoter, the ADC (alcohol dehydrogenase) promoter, PGK (phosphoglycerol kinase) promoter, alkaline phosphatase promoter.

Expression vectors containing HMW protein or HMW-derived polypeptide coding sequences can be identified by three general approaches: (a) nucleic acid hybridization, (b) presence or absence of "marker" gene functions, and (c) expression of inserted sequences such as reactivity with anti-HMW antibody. In the first approach, the presence of a foreign gene inserted in an expression vector can be detected by nucleic acid hybridization using probes comprising sequences that are homologous to the inserted HMW protein or HMW-derived polypeptide coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the HMW protein or HMW-derived polypeptide coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of HMW protein or HMW-derived polypeptide in in-vitro assay systems, e.g., binding to an HMW ligand or receptor, or binding with anti-HMW antibodies of the invention, or the ability of the host cell to hemagglutinate or the ability of the cell extract to interfere with hemagglutination by *Chlamydia*.

Once a particular recombinant DNA molecule is identified and isolated, several methods known in the art may be used to propagate it. Once a suitable host system and growth conditions are established, recombinant expression vectors can be propagated and prepared in quantity. As explained above, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered HMW protein or HMW-derived HMW may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

The proteins, polypeptides, peptides, antibodies and nucleic acids of the invention are useful as reagents for clinical or medical diagnosis of *Chlamydia* infections and for scientific research on the properties of pathogenicity, virulence, and infectivity of *Chlamydia*, as well as host defense mechanisms. For example, DNA and RNA of the invention can be used as probes to identify the presence of *Chlamydia* in biological specimens by hybridization or PCR amplification. The DNA and RNA can also be used to identify other bacteria that might encode a polypeptide related to the *Chlamydia* HMW protein. The proteins of the invention may be used to prepare polyclonal and monoclonal antibodies that can be used to further purify compositions containing the proteins of the invention by affinity chromatography. The proteins can also be used in standard immunoassays to screen for the presence of antibodies to *Chlamydia* in a sample.

7. BIOLOGICAL DEPOSITS

Certain plasmids that contain portions of the gene having the open reading frame of the gene encoding the HMW protein of *Chiamydia* that are described and referred to herein have been deposited with the American Type Culture Collection (ATCC) located at 10801 University Boulevard, Manassas. Va. 20110-2209, U.S.A., pursuant to the Budapest Treaty and pursuant to 37 C.F.R. 1.808 and prior to the filing of this application. The identifications of the respective portions of the genes present in these plasmids are shown below.

Samples of the deposited materials will become available to the public upon grant of a patent based upon this United Stated patent application. The invention described and claimed herein is not to be limited by the scope of the plasmids deposited, since the deposited embodiment is intended only as an illustration of the invention. Any equivalent or similar plasmids that encode similar or equivalent proteins or fragments or analogues thereof as described in this application are within the scope of the invention.

| Microorganisms | ATCC Accession No. | Date Deposited |
|---|---|---|
| E. coli BL21 pAH342 | ATCC 98538 | Sep. 8, 1997 |
| E. coli TOP10 (pJJ36-J) | ATCC PTA-3719 | Sep. 20, 2001 |

EXAMPLES

The above disclosure generally describes the present invention. A more specific description is provided below in the following examples. The examples are described solely for the purpose of illustration and are not intended to limit the scope of the invention. Changes in form and substitution of equivalents are contemplated as circumstances suggest or render expedient. Although specific terms have been employed herein, such terms are intended in a descriptive sense and not for purposes of limitation.

Methods of molecular genetics, protein biochemistry and immunology used but not explicitly described in the disclosure and examples are amply reported in the scientific literature and are well within the ability of those skilled in the art.

Example 1

Isolation and Purification of Mature *Chlamydia* Protein

McCoy cells were cultured either in standard 225 cm$^2$ tissue culture flasks or in Bellco spinner flasks (Cytodex microcarrier, Pharmacia) at 37° C. in 5% $CO_2$ using DMEM media supplemented with 10% *Chlamydia*-antibody free fetal bovine serum, glucose and nonessential amino acids. *C. trachomatis* $L_2$ elementary bodies (ATCC VR-902B) were prepared from lysates of infected McCoy cells. Basically, McCoy cells infected with *C. trachomatis* $L_2$ (LGV) were sonicated and cellular debris was removed by centrifugation. The supernatant containing chlamydial elementary bodies (EBs) was then centrifuged and the pellet containing EBs was resuspended in Hanks' balanced salts solution (HBSS). RNase/DNase solution was added and incubated at 37° C. for 1 hour with occasional mixing. The EB containing solution was layered onto a discontinuous density gradient (40%, 44% and 54%) of Angiovist 370 (mixture of diatrizoate melgumine and diatrizoate sodium, Berlex Laboratories, Wayne, N.J.) and ultracentrifuged for separation of the EBs on the gradient. After centrifugation the EBs were harvested from the gradient between the interface of the 44% and 54% Angiovist 370 layers. The EBs were washed in phosphate buffered saline and resuspended in HBSS.

Purified EBs were sequentially extracted with 0.1% OGP [high ionic strength] in HBSS to remove peripheral surface proteins and held on ice. The same EB preparation was then extracted with 1.0% OGP, 10 mM DTT, 1 mM PMSF, 10 nM EDTA, in a 50 mM Tris pH 7.4 buffer. Extracts were dialyzed (3500 MWCO) to remove detergent and other reagents and concentrated by lyophilization. Protein containing extracts were diluted in HBSS and passed over commercially available heparin-sepharose columns (HiTrap Col., Pharmacia). After samples were applied to the heparin column nonadhered proteins were removed by washing with excess HBSS. Bound proteins were batch eluted with PBS containing 2M sodium chloride. Eluents were dialyzed extensively to remove salt and then lyophilized. The heparin-binding proteins were size fractionated by SDS-PAGE and visualized by silver staining or analyzed by Western blotting. Protein(s) of about 105-115 KDa present in moderate amounts were detected as shown in FIG. 1. The isoelectric point of the native HMW protein was determined to be about 5.95.

To obtain one N-terminal amino acid sequence, sufficient quantities of the HMW protein ($\geq$5 ug) were electroblotted onto a PVDF membrane (Applied Biosystems), and stained with Coomassie blue. Immobilized HMW protein was released from the membrane and treated in situ with low levels of endopeptidase Lys-C, endopeptidase Arg-C and/or endopeptidase Glu-C to fragment the native protein. The resulting peptide fragments were purified by HPLC and their N-terminal amino acid sequences determined using an ABI 430 Protein Sequenator and standard protein sequencing methodologies. The N-terminal amino acid sequence is:

E-I-M-V-P-Q-G-I-Y-D-G-E-T-L-T-V-S-F-X-Y and is denoted SEQ ID No.: 3.

When a composite PDB+SwissProt+PIR+GenPept database (>145 K unique sequences) was searched with the HMW protein N-terminal sequence (20 residues) using rigorous match parameters, no precise homologies were found. Thus the HMW protein is a novel chlamydial protein. Since this protein was isolated under conditions that should release only peripheral membrane proteins (e.g. Omp2), these data indicate that the HMW protein is a surface-associated protein.

Example 2

Preparation of Antibodies to Whole *Chlamydia* EBs

To aid in the characterization of the HMW protein, hyperimmune rabbit antisera was raised against whole EBs from *C. trachomatis* $L_2$. Each animal was given a total of three immunizations of about 250 ug of *Chlamydia* EBs per injection (beginning with complete Freund's adjuvant and followed with incomplete Freund's adjuvant) at approximately 21 day intervals. At each immunization, approximately half of the material was administered intramuscularly (i.m.) and half was injected intranodally. Fourteen days after the third vaccination a fourth booster of about 100 ug of EBs was given i.m. and the animals exsanguinated 7-10 days later. A titre of 1:100,000 was obtained as determined by ELISA.

Example 3

Determination of Post-translational modifications

Recently, several *C. trachomatis* membrane-associated proteins have been shown to be post-translationally modified. The 18 kDa and 32 kDa cysteine-rich EB proteins, which are lectin-binding proteins, have been shown to carry specific carbohydrate moieties (Swanson, A. F. and C. C. Kuo. 1990. *Infect. Immun.* 58:502-507). Incorporation of radiolabelled palmitic acid has been used to demonstrate that the about 27 kDa *C. trachomatis* Mip-like protein is lipidated (Lundemose, A. G., D. A. Rouch, C. W. Penn, and J. H. Pearce. 1993. *J. Bacteriol.* 175:3669-3671). Swanson et al. have discovered that the MOMP from the $L_2$ serovar contains N-acetylglucosamine and/or N-acetylgalactosamine and these carbohydrate moieties mediate binding of MOMP to Hela cell membranes.

To ascertain whether the HMW protein is glycosylated, EBs are grown on McCoy cells in the presence of tritiated galactose or glucosamine, subjected to heparin affinity chromatography and the heparin binding proteins analyzed by SDS-PAGE and autoradiography. Briefly, McCoy cells are grown in T225 flasks under standard conditions (DMEM+ 10% FCS, 35 ml per flask, 10% $CO_2$) to about 90% confluency and inoculated with sufficient EBs to achieve 90%-100% infectivity. Following a 3 hour infection period at 37° C. cycloheximide is added (1 ug/ml) to inhibit host cell protein synthesis and the cultures reincubated for an additional 4-6 hours. Approximately 0.5 mCi of tritiated galactose (D-[4,5-$^3$H(N)]galactose, NEN) or glucosamine (D-[1,6-$^3$H(N) glucosamine, NEN) is then be added to each flask and the cultures allowed to incubate for an additional 30-40 hours. Cells are harvested by scraping and EBs purified by gradient centrifugation. HMW protein is isolated from 1.0% OGP surface extracts by affinity chromatography, eluted with NaCl and analyzed by SDS-PAGE using $^{14}$C-labelled molecular weight markers (BRL) then subjected to autoradiography. Dried gels are exposed for 1-4 weeks to Kodak X-AR film at −70° C.

To determine post synthesis lipid modification, *C. trachomatis* serovar $L_2$ is cultivated on monolayers of McCoy cells according to standard procedures. Approximately 24 hours postinfection, conventional culture media (DMEM+ 10% FCS) is removed and replaced with a serum-free medium containing cycloheximide (1 ug/ml) and [U-$^{14}$C] palmitic acid (0.5 mCi/T225 flask, NEN) and incubated for a further 16-24 hours to allow protein lipidation to occur. Surface EB extracts are prepared, heparin-binding proteins are isolated and analyzed by autoradiography as described above.

The functionality of glycosylated or lipidated moieties is assessed by treating whole EBs or OGP surface extracts with appropriate glycosidases. Following carbohydrate removal, extracts are subjected to affinity chromatography and SDS-PAGE to determine whether the HMW protein retains the ability to bind to heparin sulfate.

Example 4

Cloning of the N-terminal Segment of the HMW Protein Gene

Degenerate oligonucleotides were designed based on the N-terminal amino acid sequence of the HMW protein and were synthesized. These oligonucleotides were then used to generate gene-specific PCR products that were employed as hybridization probes to screen a *C. trachomatis* $L_2$ λZAPII DNA library to isolate the gene for the HMW protein.

Briefly, appropriate low degeneracy peptide segments were identified from the N-terminal and internal amino acid sequence data by computer analysis (MacVector, IBI) and used to guide the design of low degeneracy sequence-specific oligonucleotide PCR primer sets.

Using the N-terminal primary sequence as a guide, four degenerate oligonucleotide probes complementary to the nucleotides encoding the first six residues of the HMW peptide E-I-M-V-P-Q (SEQ ID NO.: 42 corresponding to residues 1-6 of SEQ ID NO.: 3), and comprising all possible nucleotide combinations (total degeneracy=192 individual sequences), have been designed and employed as forward amplification primers.

```
SEQ ID No.4    5'-GAA-ATH-ATG-GTN-CCN-CAA-3'
SEQ ID No.5    5'-GAA-ATH-ATG-GTN-CCN-CAG-3'
SEQ ID No.6    5'-GAG-ATH-ATG-GTN-CCN-CAA-3'
SEQ ID No.7    5'-GAG-ATH-ATG-GTN-CCN-CAG-3'
```

Two additional oligonucleotide probes representing the reverse complement DNA sequence of the internal five residue peptide Y-D-G-E-T (residues 9-13 of SEQ ID No.: 3), and comprising all possible nucleotide combinations (total degeneracy=128 individual sequences), have been designed and employed as reverse amplification primers.

```
SEQ ID No.8    5'-NGT-YTC-NCC-RTC-ATA-3'
SEQ ID No.9    5'-NGT-YTC-NCC-RTC-GTA-3'
```

Oligonucleotides were synthesized on an ABI Model 380B DNA synthesizer using a 0.2 µmol scale column (trityl-on, auto-cleavage) and standard phosphoramidite chemistry. Crude oligonucleotides were manually purified over C-18 syringe columns (OP Columns, ABI). Purity and yield were ascertained spectrophotometrically (230/260/280 ratios).

Standard PCR amplification reactions (2 mM $Mg^{2+}$, 200 mmol dNTPs, 0.75 units AmpliTaq, 50 ul final volume) were programmed using about 0.2 ug *C. trachomatis* $L_2$ DNA (about $3 \times 10^7$ copies of the HMW protein gene if single copy) and about 100 pmol of each forward (N-terminal oligo) and reverse (internal oligo) primer. Higher than normal concentrations of primers (~20 pmol/50 ul) were used for amplification, at least initially, in order to compensate for primer degeneracy. Amplification of target sequences was achieved using a standard 30-cycle, three-step thermal profile, i.e. 95° C., 30 sec; 60° C., 45 sec, 72° C., 1 min. Amplification was carried out in sealed 50 ul glass capillary tubes using a Idaho Technologies thermal cycler. To verify that the PCR products generated during these amplification reactions were specific for the HMW protein coding sequence and were not "primer-dimer" or other DNA amplification artifacts, amplimers were purified using silica-gel spin columns (QIAGEN), cloned into the PCR cloning vector pZERO (StrataGene), and subjected to direct DNA sequence analysis.

The DNA sequence for the cloned PCR products were determined using conventional dideoxy-terminator sequencing chemistry and a modified T7 DNA polymerase (Sequenase, USB). Briefly, each double stranded plasmid template was denatured by a brief treatment with NaOH. Following neutralization, each denatured template was used to program 4 separate sequencing reactions. Each reaction contained the M13 universal forward sequencing primer (21mer) but a different ddNTP/dNTP termination mix (i.e. A, G, C, or T). Termination products were labelled by including [α-$^{35}$S] dATP in the reaction (~50 uCi/reaction, >3000 Ci/mmol, Amersham). Individual extension products were denatured (formamide, ~95° C.) and subjected to high resolution denaturing polyacrylamide gel electrophoresis (6% acrylamide, 8M urea, TAE buffer, ~500V, ~90 min). Sequencing gels were then transferred to filter paper (Whatmann 3MM), dried under vacuum, and then autoradiographed at −70° C. for 24-72 hours. Base ladders were read manually from each gel and a consensus sequence determined.

HMW protein-specific amplimers suitable for library screening and/or Southern blotting were produced by PCR and uniformly radiolabelled during the amplification process by adding [α-$^{32}$P]dNTPs (about 50 uCi each dNTP, Amersham, >5000 Ci/mmol) to the reaction mixture. Labelling reactions were performed as above except reactions were performed in 0.5 ml microcentrifuge tubes using a Bellco Thermal Cycler. Unincorporated label and amplification primers were removed from the reaction mixture using centrifugal size-exclusion chromatography columns (BioSpin 6 columns, BioRad).

A highly redundant *C. trachomatis* serovar L$_2$ DNA library (>50,000 primary clones) has been constructed by cloning size-fractionated fragments ≧10 Kbp produced from a partial EcoRI digest of genomic DNA into the lambda cloning vector λZAPII (Stratagene). Radiolabelled HMW protein-specific PCR products were used to screen this library for recombinant clones that carry all or part of the HMW protein coding sequence. Standard recombinant DNA procedures and methodologies were employed for these experiments. All phage that hybridized with these probes were purified to homogeneity by sequential rounds of plating and hybridization screening. Once reactive phage were purified, insert-containing phagmids (pBluescript SK- derivatives) were excision-rescued from the parental phage by coinfecting host cells with an appropriate helper phage, e.g. R408 or VCSM3 (Stratagene). Individual phagmids were further purified by streak-plating on LB agar containing ampicillin (100 ug/ml) and selecting for individual colonies.

To confirm purified phagemid derivatives carried the HMW protein sequences, plasmid DNA was prepared and used to program amplification reactions containing the HMW protein-specific PCR primer sets. The presence of HMW protein-specific inserts was confirmed by the production of the appropriate sized PCR product.

Plasmid pAH306 is one HMW protein-containing derivative that was isolated by these methodologies.

Physical Mapping of pAH306

The inserts from pAH306 were physically mapped and the location of HMW protein gene determined using appropriate six-base restriction endonucleases (e.g. EcoRI, HindIII, BamHI, PstI, SmaI, KpnI, etc.) and HMW protein coding sequences localized by Southern hybridization employing radiolabelled N-terminal-specific PCR products as probes. The orientation and extent of HMW protein-specific sequences were determined by PCR analysis using primer sets consisting of HMW protein-specific forward primers and reverse primers complementary to either the T3 or T7 promoter sequences located in the cloning vector.

Plasmid pAH306 was determined to contain a single ⁻6.6 Kbp EcoRI fragment of chlamydial origin. Directional PCR analysis of pAH306 demonstrated this derivative encodes roughly 1.5 Kbp of the N-terminal region of the HMW protein gene.

The DNA sequence for the HMW protein gene encoded on pAH306 was obtained for both strands via conventional "sequence-walking" coupled with asymmetric PCR cycle sequencing methodologies (ABI Prism Dye-Terminator Cycle Sequencing, Perkin-Elmer). Sequencing reactions were programmed with undigested plasmid DNA (⁻0.5 ug/rxn) as a template and appropriate HMW protein-specific sequencing primers (⁻3.5 pmol/rxn).

In addition to the template and sequencing primer, each sequencing reaction (⁻20 ul) contained the four different dNTPs (i.e. A, G, C, and T) and the four corresponding ddNTPs (i.e. ddA, ddG, ddC, and ddT) terminator nucleotides; with each terminator being conjugated to one of four different fluorescent dyes. Single strand sequencing elongation products were terminated at random positions along the template by the incorporation of the dye-labelled ddNTP terminators. Fluorescent dye-labelled termination products were purified using microcentrifuge size-exclusion chromatography columns (Princeton Genetics), dried under vacuum, suspended in a Template Resuspension Buffer (Perkin-Elmer), denatured at 95° C. for ⁻5 min, and resolved by high resolution capillary electrophoresis on an ABI 310 Automated DNA Sequenator (Perkin-Elmer).

Figure 5:
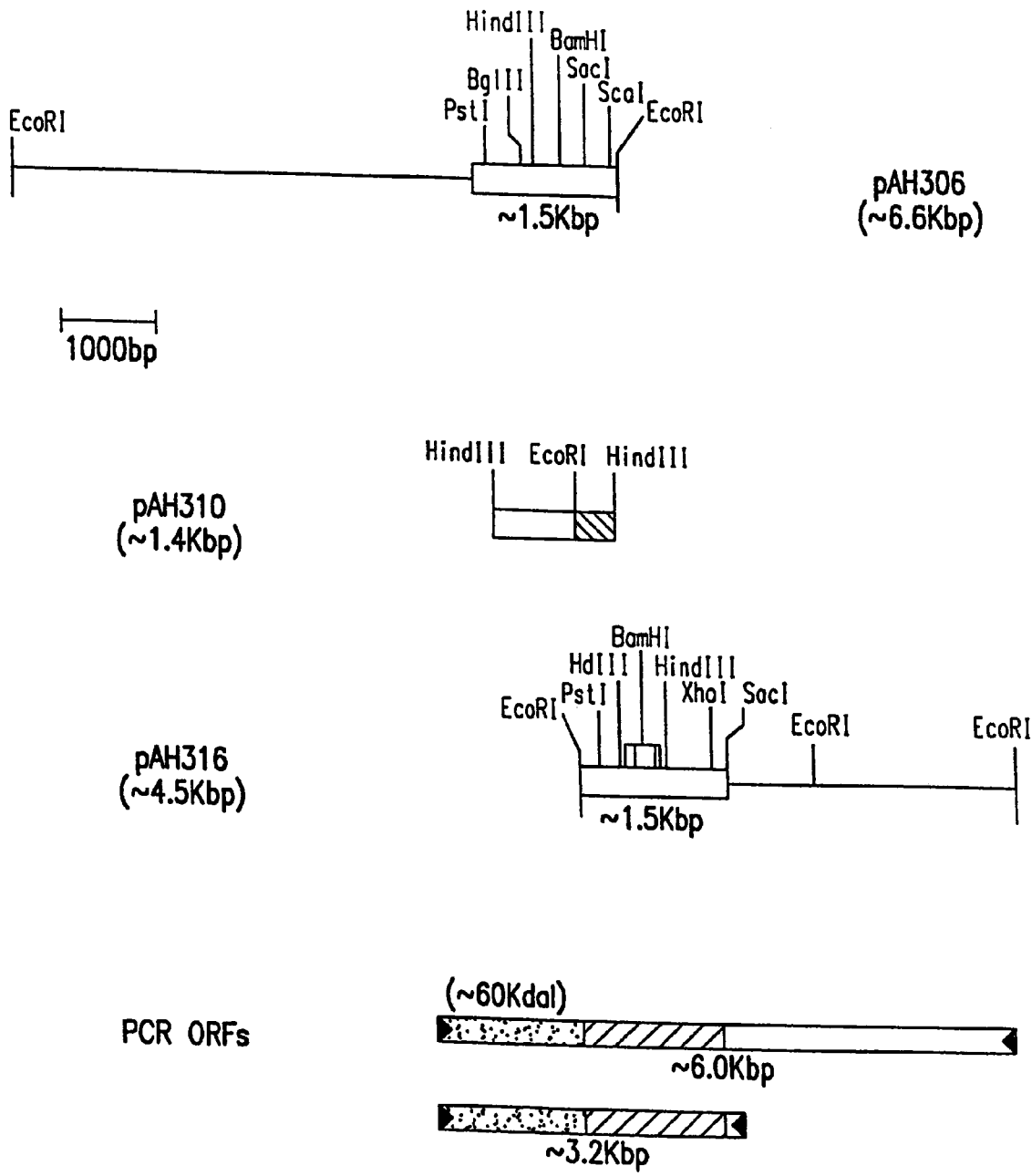
FIG. 5. Map of plasmids pAH306, pAH310, pAH312, pAH316 and the PCR open reading frame.

DNA sequence data produced from individual reactions were collected and the relative fluorescent peak intensities analyzed automatically on a PowerMAC computer using ABI Sequence Analysis Software (Perkin-Elmer). Individually autoanalyzed DNA sequences were edited manually for accuracy before being merged into a consensus sequence "string" using AutoAssembler software (Perkin-Elmer). Both strands of the HMW protein gene segment encoded by pAH306 were sequenced and these data compiled to create a composite sequence for the HMW protein gene segment. The sequence encoding the segment of HMW protein is listed as SEQ ID No.: 10 and is represented by nucleotides 466 to 1976 in FIG. 2A-C. A map of pAH306 is shown in FIG. 5.

Database analysis (e.g. primary amino acid homologies, hydropathy profiles, N-/O-glycosylation sites, functional/conformational domain analyses) of the DNA and predicted amino acid sequences for the HMW protein was performed using GeneRunner and Intelligentics software, indicating the HMW protein is novel.

Example 5

Cloning of the C-terminal Segment of the HMW Protein Gene

Chromosome walking was employed to isolate the C-terminal portion of the HMW protein gene. A ⁻0.6 Kbp BamHI-EcoRI fragment distal to the N-terminal sequence of the mature HMW protein and proximal to the T3 promoter sequence of the vector was chosen as the probe for the initial chromosome walk. Briefly, pAH306 was digested to completion with BamHI and EcoRI and the digestion products size fractionated by agarose gel electrophoresis (0.8% agarose in TAE buffer). The desired ⁻0.6 Kbp BamHI/EcoRI (B/E) band was excised from the gel and purified using commercially available silica gel microcentrifuge chromatography columns and reagents (QIAGEN).

The purified 0.6 Kbp B/E fragment was radiolabelled with [α-dATP] (>3000 Ci/mmol, Amersham) via random-priming labelling methodologies employing commercially available reagents (Boehringer Mannheim) and used to probe Southern blots of *C. trachomatis* L$_2$ genomic DNA that had been digested to completion with HindIII.

The 0.6 Kbp B/E probe from pAH306 hybridized to a ⁻1.4 Kbp HindIII genomic fragment. Based on the experimentally derived restriction map of the HMW protein gene segment encoded on pAH306, this fragment encodes ⁻0.2 Kbp of the C-terminal HMW protein sequence.

The radiolabelled 0.6 Kbp B/E fragment was used subsequently to probe a moderately redundant (⁻5,000 primary clones) *C. trachomatis* L2 library to identify clones that contain the ⁻1.4 Kbp HindIII fragment. Briefly, *C. trachomatis* L$_2$ genomic DNA was digested to completion using a ⁻10-fold excess of the restriction endonuclease HindIII (⁻10 units per lug of genomic DNA, 37° C., 18-24 hours). Digestion products were size fractionated by agarose gel electrophoresis (0.8% agarose, TAE) and DNA fragments ranging in size from ⁻1.0 Kbp to 2.0 Kbp were excised from the gel. Excised agarose strips contain the desired DNA fragment sizes were dissolved in a solubilization/binding solution (QX1, QIAGEN) and purified using commercially available silica-gel spin columns (QIAGEN). Purified 1.0-2.0 Kbp genomic HindIII fragments were then cloned into the pBlueScript SK- plasmid which had been previously digested to completion with HindIII and treated with calf intestinal phosphatase to prevent vector religation.

Vector/insert ligations were performed in a ⁻50 ul final reaction volume (50 mM Tris-HCl, pH 7.00; 10 mM NaCl; 1 mM ATP; 0.5 mM DTT) at 25° C. for ⁻16-24 hours using T4 DNA ligase (⁻10 units/reaction) and a vector:insert molar ratio of approximately 1:10. Following ligation, aliquots (⁻50 ng ligated DNA) were used to electroporate a competent E. coli host, e.g. E. coli TOP10. Electroporated cells were then plated onto LB agar containing ⁻100 ug/ml ampicillin to select for plasmid-harboring clones. Approximately 1,000 plasmid-harboring $Ap^R$ transformants were transferred directly from LB $Ap^{100}$ agar plates onto nylon membranes (HyBond N+, Amersham) by capillary action.

Following transfer, plates were re-incubated at 37° C. to regenerate viable colonies for further manipulation. Colonies transferred to membranes were lysed and DNA liberated by treating the colony blots with a denaturing SDS/NaOH solution. A Tris buffered NaCl solution was used to neutralize and stabilize lysis material. Released DNA was immobilized onto the membranes by UV irradiation. Standard recombinant DNA procedures and methodologies were employed to probe the colony blots with the radiolabelled 0.6 Kbp B/E fragment and identify recombinant derivatives which carry the desired ⁻1.4 Kbp HindIII fragment.

Plasmid pAH310 was one derivative isolated by these procedures and the coding segment of the HMW protein is represented by nucleotides 994-2401 in FIG. 2A-C.

Restriction analysis using HindIII and EcoRI, individually and in combination, together with DNA sequence analysis of purified plasmid DNA confirmed pAH310 encodes the expected ⁻1.4 Kbp HindIII fragment. These analyses also demonstrated that the ⁻1.4 Kbp insert consists of the same ⁻1.2 Kbp HindIII-EcoRI fragment that is present in pAH306 and a unique ⁻0.2 Kbp EcoRI-HindIII fragment that encodes C-terminal HMW protein-specific DNA.

The ⁻0.2 Kbp EcoRI-HindIII (E/H) fragment was chosen as the probe for the second chromosome walk. Briefly, pAH310 was digested to completion with EcoRI and HindIII and the digestion products size fractionated by agarose gel electrophoresis (0.8% agarose in TAE buffer). The desired ⁻0.2 Kbp (E/H) band was excised from the gel, purified, radiolabelled with [α-$P^{32}$]dATP, and used as a probe to identify clones in the original C. trachomatis $L_2$ λZAPII genomic library that encode the C-terminal segment of the HMW protein gene.

Plasmid pAH316 is one derivative isolated by these procedures. Restriction analysis of pAH316 demonstrated that this derivative contains a C. trachomatis $L_2$ insert of ~4.5 Kbp which consists of two EcoRI fragments of ~2.5 Kbp and ~2.0 Kbp in size. Southern hybridization analysis using the ~0.2 Kbp E/H fragment as a probe localized this sequence to the ~2.5 Kbp EcoRI fragment of pAH316. Directional PCR analyses employing purified pAH316 plasmid DNA as a template and amplification primer sets specific for ~0.2 Kbp E/H fragment and T3 and T7 vector sequences demonstrated pAH316 encodes the C-terminal segment of the HIMW protein gene. The coding segment of the HMW protein is represented by nucleotides 1977 to 3420 in FIG. 2A-C, and is listed as SEQ ID No.: 11.

Example 6

Production of Truncated HMW Recombinant Protein

The N-terminal half of the HMW protein was PCR cloned as a ⁻1.5 Kbp fragment into the commercially available E. coli expression plasmid pTrcHisB (Invitrogen). The forward primer used in these reactions was designated 140FXHO (57mer), listed as SEQ ID No. 18, and contains sequences complementary to the first 10 N-terminal residues of the mature HMW protein. In addition to the HMW proteincoding sequences, this forward primer also carries a unique XhoI restriction site located optimally located upstream of the first residue of the mature HMW protein (Glu/E) for proper fusion to the $(His)_6$ affinity purification domain encoded on the vector plasmid, and 5' terminal 6 base G/C clamp for effective amplification and a 12 base internal spacer for effective endonuclease recognition and digestion.

SEQ ID No.18  5-AAG-GGC-CCA-ATT-ACG-CAG-AGC-TCG-
              AGA-GAA-ATT-ATG-GTT-CCT-CAA-GGA-
              ATT-TAC-GAT-3'

SEQ ID No.19  5'-CGC-TCT-AGA-ACT-AGT-GGA-TC-3'

The commercially available reverse sequencing primer SK (20mer, StrataGene), SEQ ID No. 19, which is complementary to phagemid sequences downstream of the EcoRI site in pAH306, was used as the reverse amplification primer in these reactions. To obtain acceptable yields of the HMW protein ORF product (⁻1.5 Kbp), PCR amplification was performed using a mixture of thermostable DNA polymerases consisting of T. thermophilus DNA polymerase (Advantage Polymerase), as the primary amplification polymerase and a minor amount of a second high fidelity thermostable DNA polymerase to provide additional 5'-3' proofreading activity (CloneTech). An anti-Tth DNA polymerase antibody was added to the reaction mixture to provide automatic "hot-start" conditions which foster the production of large >2 Kbp amplimers. pAH306 plasmid DNA purified using a commercially available alkaline/SDS system (QIAGEN) and silica gel. spin columns (QIAGEN) was used to program these amplification reactions (⁻0.2 ng/reaction).

The ⁻1.5 Kbp amplimer was purified from unincorporated primers using silica gel spin columns and digested to completion using an excess of XhoI and EcoRI (⁻10 units per lug DNA). The purified and digested N-terminal truncated HMW protein ORF was then be cloned into the commercially available expression plasmid pTrcHisB that had been previously digested with both XhoI and EcoRI (5:1, insert:vector ratio). Aliquots from the ligation reaction were then be used to electrotransform a suitable E. coli host (e.g. TOP10).

Mini-prep DNA from ampicillin-resistant transformants picked at random were prepared, digested to completion with XhoI, EcoRI, or a combination of both and examined for the presence and orientation of the ~1.5 Kbp truncated HMW protein ORF insert by agarose gel electrophoresis. Mini-prep DNA from clones determined to carry the ~1.5 Kbp XhoI/EcoRI insert was prepared and used to program asymmetric PCR DNA sequencing reactions to confirm the fidelity of the junction formed between the HMW protein fragment and the $(His)_6$ affinity purification domain of the expression vector. Plasmid pJJ36-J was one recombinant derivative isolated by these procedures and is represented by nucleotides 446 to 1980 in FIG. 2A-C. The deduced amino acid sequence of the truncated fragment of HMW protein is represented by amino acids 29 to 533 in FIG. 3 and is listed as SEQ ID No. 17.

Example 7

Determination of Presence in Other Species

Polymerase chain reaction analyses were undertaken to establish the presence of the HMW gene in several clinically recognized *C. trachomatis* strains and as well as other chlamydial species, e.g., *C. pneumoniae*. *Chlamydia trachomatis* strains as frozen stocks from the ATCC (Rockville, Md.) were used to infect subconfluent monolayers (about 80%) of McCoy cells according to standard procedures. Infected monolayers were either centrifuged in a Sorvall RT6000B centrifuge (~1,300 rpm, 25° C., 30 min) and/or treated with dextran sulfate (~50 ug/ml) at the time of infection to enhance initial attachment of the low infectivity biovars (non-LGV) to host cells and thus increase the final EB yield. Roughly 48 hours later, infected monolayers were collected by scraping and host cells disrupted by sonication to release elementary bodies (EBs). Total DNA was extracted from purified EBs (~$10^7$-$10^8$) of each strain using the proteinase K/Nonidet P40 method described by Denamur, et al., *J. Gen. Microbiol.* 137:2525-2530 (1991), incorporated herein by reference, and further purified by phenol/chloroform extraction and salt precipitation. Purified *Chlamydia pneumoniae* (AR-139) genomic DNA was purchased from Advanced Biotechnologies Inc.

To determine the presence of the HMW protein gene in these strains, amplification reactions were programmed using total *Chlamydia* DNA as template and the HMW protein segment-specific oligonucleotide primer (21mers) sets listed below.

```
SEQ ID No.20    5'-ATG-GTT-CCT-CAA-GGA-ATT-TAC-G-3'

SEQ ID No.21    5'-GGT-CCC-CCA-TCA-GCG-GGA-G-3'
```

Briefly, standard PCR amplification reactions (2 mM $Mg^{2+}$, 100 mmol dNTPs, 0.75 units AmpliTaq polymerase, 50 ul final volume) were programmed using approximately 15 ul of the crude *C. trachomatis*-DNA extracts (~10 ul of the commercially available *C. pneumoniae* DNA) and ~20 pmol of each forward and reverse HMW protein-specific amplification primers of SEQ ID No. 20 and 21. Amplification of small target sequences (<2 Kbp) was achieved using a 32-cycle, three-step thermal profile, i.e. 95° C., 30 sec; 60° C., 30 sec, 72° C., 1 min. Amplification of longer target sequences for ORF-cloning and sequencing was carried out using the crude DNA extracts in an identical fashion except that a MAb-inactivated Tth/Vent DNA polymerase enzyme combination was employed (Advantage PCR, Clontech) and a 72° C. extension time was used that matched the size of the desired PCR product plus 2 min (i.e. desired PCR product=6 Kbp, extension time=8 min).

Both conventional and long-distance PCRs were carried out using 0.2 ml thin-walled polypropylene microcentrifuge tubes in an ABI 2400 Thermal Cycler (Perkin-Elmer). Following thermal cycling, aliquots (~20 ul) of the reactions were analyzed and PCR products identified by standard agarose gel electrophoresis (0.8% agarose in TAE buffer) and ethidium bromide staining. The results showed that the HMW protein is highly conserved in clinically relevant serovars; the HMW gene was present in all *Chlamydia* samples strains tested, including serovars B, Ba, D, E, F, G, H, I, J, K, $L_1$, $L_2$ and MoPn and in *C. pneumoniae*.

Example 8

Determination of Sequence Variation

To establish the degree of DNA and amino acid sequence variation among different *Chlamydia* strains, the gene for the HMW protein was PCR-cloned from both a *C. trachomatis* B serovar (representing the trachoma group of organisms) and from a *C. trachomatis* F serovar (representing the low infectivity STD biovars) and compared to the HMW protein consensus *C. trachomatis* $L_2$ sequence.

Briefly, LD-PCR was used to generate ~6 Kbp HMW protein-specific DNA fragments from *C. trachomatis* B and F genomic DNA that contain the complete coding sequence for the mature HMW protein. Amplification conditions for these LD-PCR exercises were as described in Example 6. The reverse amplification primer employed in these reactions (p316 Kpn-RC, 56mer), listed as SEQ ID No. 13, is complementary to a sequence located ~3 Kbp downstream of the predicted HMW protein termination codon. As an aide to cloning the desired ~6 Kbp amplimer, a single KpnI restriction endonuclease site 5' to the chlamydial sequence was engineered into the p316 Kpn-RC primer. The forward amplification primer used for these reactions (p306 Kpn-F, 56mer), listed as SEQ ID No. 12, contains the sequence complementary to the first 10 amino acid residues (30 nucleotides) specifying the mature HMW protein as well as a 5' sequence specifying a KpnI site. p306 Kpn-F was designed such that the sequence encoding the N-terminus of the mature HMW protein could be linked in-frame to a hexa-His affinity domain encoded downstream of the highly efficient trc promoter on the *E. coli* expression vector pTrcHisB (ClonTech) when the ~6 Kbp amplimer was inserted into the KpnI site of this vector.

```
SEQ ID No.12    5'-AAG-GGC-CCA-ATT-ACG-CAG-AGG-GTA-
                CCG-AAA-TTA-TGG-TTC-CTC-AAG-GAA-TTT-
                ACG-AT-3'

SEQ ID No.13    5'-AAG-GGC-CCA-ATT-ACG-CAG-AGG-GTA-
                CCC-TAA-GAA-GAA-GGC-ATG-CCG-TGC-TAG-
                CGG-AG-3'
```

The ~6 Kbp HMW protein products were purified using silica-gel spin columns (QIAGEN) and the fragments subjected to two 8-10 hour cycles of KpnI digestion using a 10-fold excess of KpnI (~10 units per 1 ug of purified fragment, 37° C.). Following the second digestion, residual restriction enzyme activity was removed using QIAGEN spin columns and the ~6 Kbp KpnI HMW protein fragments cloned into the pTrcHisB plasmid which had been previously digested to completion with KpnI and treated with calf intestinal phosphatase to prevent vector religation.

Vector/insert ligations were performed in a ~50 ul final reaction volume (50 mM Tris-HCl, pH 7.00; 10 mM NaCl; 1 mM ATP; 0.5 mM DTT) at 25° C. for ~2 hours using T4 DNA ligase (~10 units/reaction) and a vector:insert molar ratio of approximately 1:5. Following ligation, aliquots (~50 ng ligated DNA) was used to electroporate a competent *E. coli* host, e.g. *E. coli* TOP10. Plasmid-harboring transformants were selected by plating electrotransformed cells onto LB agar containing 100 ug/ml ampicillin. Ampicillin-resistant ($Ap^R$) transformants appearing after a ~18-24 hour incubation period at 37° C. were picked at random and restreaked onto the same selective media for purification.

A single, purified Ap$^R$ colony from each initial transformant was used to inoculate ~5 ml of LB broth and grown overnight at 37° C. in a incubator shaker with mild aeration (~200 rpm). Cells from broth cultures were harvested by centrifugation and used to prepare small quantities of plasmid DNA. Commercially available reagents (QIAGEN Plasmid Mini Kits) were employed for these plasmid extractions. Plasmid derivatives carrying inserts were presumptively identified by electrophoresing the non-digested plasmid DNA in agarose gels (0.8% agarose in TAE buffer) and identifying derivatives greater in size than vector plasmid. Insert-containing derivatives were confirmed and the orientation of the HMW protein inserts relative to vector sequences were determined using appropriate restriction endonucleases (KpnI, EcoRI, HindIII, BamHI, etc.), either separately or together in various combinations.

The DNA sequence of the C. trachomatis B and F HMW protein genes were obtained for both strands using "sequence walking" the asymmetric dye-terminator PCR cycle sequencing methodology (ABI Prism Dye-Terminator Cycle Sequencing, Perkin-Elmer) described in Example 4. Reactions were programmed with plasmid mini-prep DNA and individual HMW protein sequence-specific primers that were employed in the sequencing of the HMW protein gene from the L$_2$ type strain.

DNA sequence data were collected using the ABI 310 Sequenator and analyzed automatically on a PowerMAC computer and appropriate computer software as described in Example 4. Individually autoanalyzed DNA sequences were edited manually for accuracy before being merged into a consensus sequence "string" using AutoAssembler software (Perkin-Elmer). Both strands of the HMW protein gene from the C. trachomatis B and F serovars were sequences for both the C. trachomatis B and F HMW protein genes. The amino acid sequences encoded are listed as SEQ ID Nos.: 15 and 16. Sequence comparisons of the L$_2$, F and B strains are presented in FIG. 6A-B.

Example 9

Production of Recombinant Protein

To produce sufficient quantities of recombinant HMW protein for both immunogenicity and animal protection studies, the HMW gene has been PCR cloned into suitable E. coli and baculovirus expression systems. Large quantities of rHMW protein are produced in an E. coli-based system as a chimeric fusion protein containing an N-terminal (His)$_6$ affinity purification domain. The complete HMW protein open reading frame (ORF) was PCR-cloned from the C. trachomatis L$_2$ genome as a single KpnI fragment and fused in the proper orientation and in the correct reading frame to the (His)$_6$ affinity purification domain encoded on the high expression plasmid vector pTrcHisB (CloneTech) as described in Example 5.

The (His)$_6$ affinity purification domain is part of a high expression locus consisting of the highly efficient tac promoter (IPTG-inducible) and consensus Shine and Delgarno ribosome binding site (RBS) located immediately upstream of the (His)$_6$ affinity purification domain. The HMW protein genes from C. trachomatis LGV L$_2$, C. trachomatis B, and C. trachomatis F were PCR cloned as ~3.0 Kbp fragments. The forward primer (56mer) used in these reactions was designated p306 Kpn-F and contains sequences complementary to the first 10 N-terminal amino acid residues of the mature HMW protein, listed as SEQ ID No 12. In addition to the HMW protein coding sequences, this forward primer also carries a unique KpnI restriction site located optimally located upstream of the first residue of the mature HMW protein (Glu) for proper fusion to the (His)$_6$ affinity purification domain encoded on the vector plasmid, and 5' terminal 6 base G/C clamp for effective amplification and a 12 base internal spacer for effective endonuclease recognition/digestion. The reverse PCR primer, designated p316 Kpn-3RC, contains a reverse complement sequence to a C. trachomatis sequence located ~0.2 Kbp downstream of the HMW protein termination codon, listed as SEQ ID No. 14. As with p306 Kpn-F, the reverse primer also contains a KpnI restriction site 5' to the C. trachomatis sequences, a 6 base G/C clamp, and a 12 base internal spacer.

To obtain acceptable yields of the HMW protein ORF product (about 3,500 bp), PCR amplification was performed using a mixture of thermostable DNA polymerases consisting of T. thermophilus DNA polymerase as the primary amplification polymerase and a minor amount of a second high fidelity thermostable DNA polymerase to provide additional 5'-3' proofreading activity (Advantage Polymerase, CloneTech). An anti-Tth DNA polymerase antibody was added to the reaction mixture to provide automatic "hot-start" conditions which foster the production of large (>2 Kbp) amplimers.

Genomic DNA from the various C. trachomatis strains was isolated from EBs as described in the example above and used to program these reactions. Following amplification, the desired reaction products were purified from excess primers using commercially available silica-gel spin columns and reagents (QIAGEN) and digested to completion with an excess of KpnI (~10 units per lug DNA). The purified and digested KpnI HMW protein ORF was then be cloned into the KpnI predigested pTrcHisB expression plasmid (5:1, insert vector ratio). Aliquots from the ligation reaction were then used to electrotransform a suitable E. coli host (e.g. TOP10).

Mini-prep DNA from ampicillin-resistant transformants picked at random were prepared, digested to completion with KnI, HindIII, or a combination of both and examined for the presence and orientation of the ~3.2 Kbp HMW protein ORF insert by agarose gel electrophoresis and ethidium bromide staining. Mini-prep DNA was used to program asymmetric PCR DNA sequencing reactions as described in example(s) above to confirm the fidelity of the junction formed between the HMW protein fragment and the (His)$_6$ affinity purification domain of the vector. Plasmid pAH342 was one derivative isolated by these procedures, which contains the HMW protein gene ORF from C. trachomatis L$_2$ and is represented by nucleotides 466 to 3421 in FIG. 2A-C.

Recombinants were grown in 2×-YT broth containing 100 ug/ml Ap to mid-log phase (~0.5 O.D.$_{600}$) and induced with IPTG (1 mM final) for an additional 4-5 hours to activate transcription from the vectors trc promoter. Cells were harvested by centrifugation and crude cell lysates prepared by lysis using a French pressure cell.

Alternatively, expression of rHMW protein may be obtained by using a baculovirus expression system. Here, the HMW protein ORF from C. trachomatis L$_2$ and C. trachomatis F were PCR-cloned as ~3 Kbp PCR products into a baculovirus transfer vector (e.g. pFastBacHTb) that had been previously digested to completion with KpnI and treated with CIP to minimize vector religation in essentially the same manner as described for pTrcHisB. The HMW protein expression cartridge generated in this cloning exercise (i.e. the baculovirus polyhedron promoter, N-terminal (His)$_6$ affinity purification domain, HMW protein gene ORF) was then transferred to the baculovirus genome by site-specific transposition using a commercially available bacmid system (Bac-to-Bac, Gibco)

Briefly, the HMW protein baculovirus expression plasmid was used to transform competent *E. coli* DH10bac (Gibco) cells containing a bacmid (a hybrid baculovirus-plasmid replicon) to gentamicin resistance using standard transformation and selection methodologies. Transformants where the HMW protein expression cartridge had successfully transposed from the expression plasmid to the appropriate receptor site within the lacZ gene located on the bacmid replicon were identified using a standard IPTG/X-gal blue-white selection.

White, $Gm^R$ transformants were picked at random and restreaked for purification. Bacmid DNA was prepared from broth cultures by the method of Ish-Horowitz, *N. A. R.* 9:2989-2993 (1981) incorporated herein by reference, and is used to transfect *Spodoptera frugiperda* 9 cells. Following plaque purification, recombinant HMW protein baculovirus is used to infect large scale *Spodoptera* suspension cultures. A yeast expression system is used to generate a glycosylated form of HMW protein.

Example 10

Purification of Recombinant Protein

Recombinant HMW protein was purified to homogeneity using standard preparative immobilized metal affinity chromatography (IMAC) procedures. Briefly, an *E. coli* strain harboring an expression plasmid containing HMW protein gene was grown in Luria broth in a 5l fermenter (New Brunswick) at 37° C. with moderate aeration until mid-log phase (~0.5 $O.D._{600}$) and induced with IPTG (1 mM final) for 4-5 hours. Cell paste was collected, washed in PBS and stored at ~20° C. Aliquots of frozen cell paste (~9-10 g wet weight) were suspended in ~120 ml of D-PBS by mechanical agitation and lysed by passage through a French pressure cell (2×, 14,000 psi, 4° C.). Soluble protein was then removed from rHMW protein inclusion bodies by high speed centrifugation (~10,000×g, 4° C., 30 min).

The insoluble pellet containing rHMW protein was suspended in ~20 ml of ice cold D-PBS by homogenization and centrifuged as above. Washed rHMW protein inclusion bodies were then denatured by suspension in a sodium phosphate buffer (0.1M, pH7.0) containing 6M guanidine hydrochloride and loaded onto a $Ni^{2+}$-affinity column (1.5 cm×25 cm, bed volume ~15 ml) prepared from Fast-Flow Chelating Sepharose (Pharmacia) and charged with $Ni^{2+}$ or $Zn^{2+}$ ions by standard procedures. Unbound material was removed by washing the column with ~5-10 column volumes of a sodium phosphate buffer (0.1M, pH7.0) containing 8M urea.

Recombinant HMW protein bound to the affinity resin by virtue of the N-terminal $(His)_6$ affinity purification domain was eluted using a pH 4.0 sodium phosphate/8M urea buffer (~20 ml). Eluted material was neutralized by the addition of 1.0M Tris-HCl (~2.5 ml, pH 7.5) and dialyzed against TE buffer containing SDS (0.5%) to remove the urea. Dialyzed material was concentrated using a Centricon-30 centrifugal concentrator (Amicon, 30,000 MWCO) and mixed with a 1/5 volume of 5×SDS gel sample buffer containing 1 mM 2-mercaptoethanol. (Lammeli) and boiled at 100° C. for 5 min.

Figure 4:
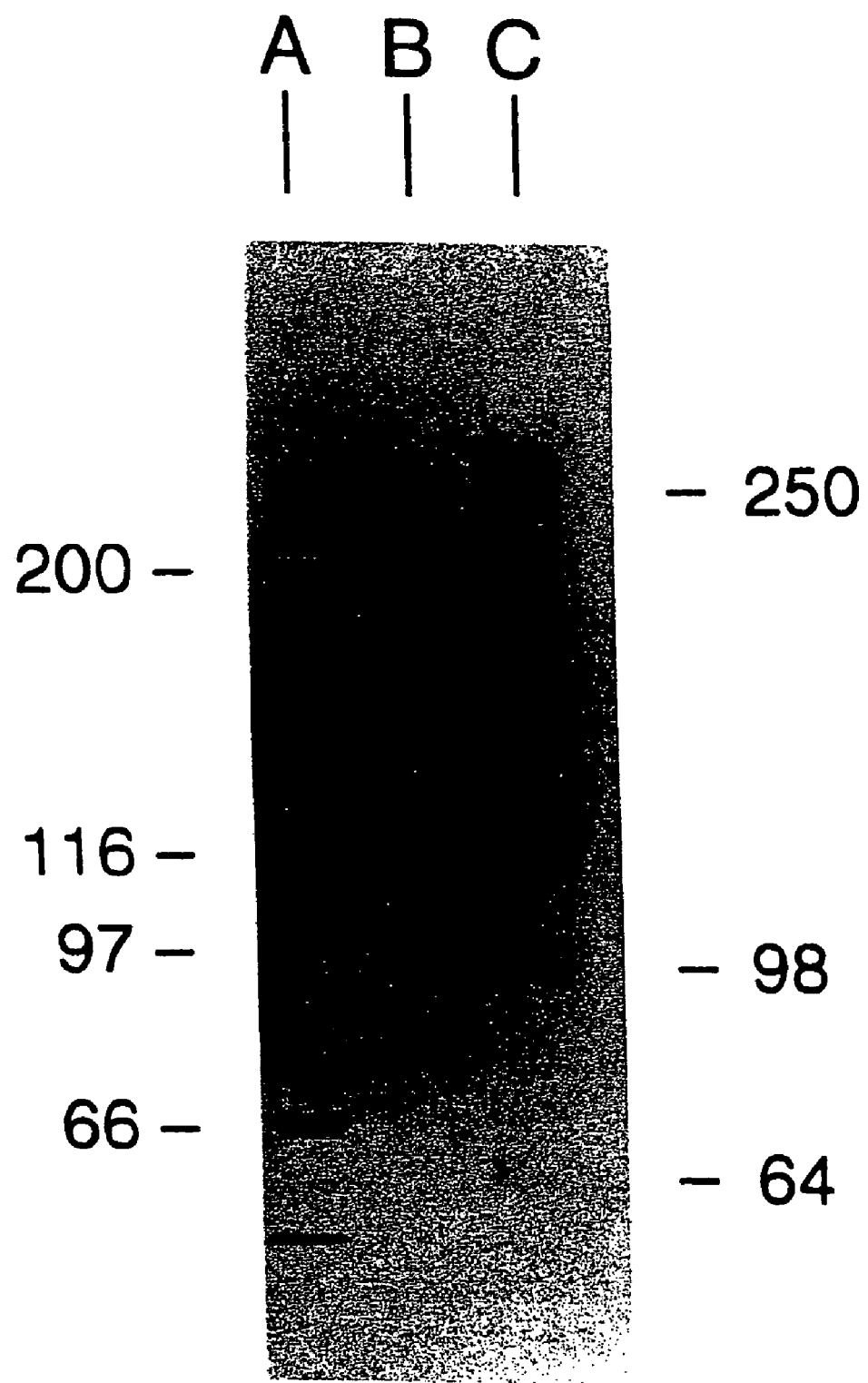
FIG. 4. SDS-PAGE of partially purified recombinant HMW protein from C. trachomatis LGV$L_2$ expressed in E. coli. Counterstained and prestained SDS-PAGE standards were used as molecular weight markers. The positions of the molecular weight markers in the gel are noted on the left and right side of the figure by lines to the molecular weights (kDa) of some of the markers. See Text Example 10 for details.
  Lane A: Mark 12 Wide Range Molecular Weight Markers (Novex); myosin, 200 Kdal; B-galactosidase, 116.3 Kdal; phosphorylase B, 97.4 Kdal; bovine serum albumin, 66.3 Kdal.
  Lane B: C. trachomatis $L_2$ recombinant HMWP.
  Lane C: SeeBlue Prestained Molecular Weight markers (Novex); myosin, 250 Kdal; bovine serum albumin, 98 Kdal; glutamic dehydrogenase, 64 Kdal.

Samples were loaded onto Tris/glycine preparative acrylamide gels (4% stacking gel, 12% resolving gel, 30:0.8 acrylamide:bis solution, 3 mm thickness). A prestained molecular weight standard (SeeBlue, Novex) was run in parallel with the rHMW protein samples to identify size fractions on the gel. The area of the gel containing proteins having molecular masses of ~105-110 Kdal was excised and the proteins electroeluted using an Elu-Trap device and membranes (S&S) as specified by the manufacturer. Electroeluted protein was dialyzed to remove SDS. The protein concentration of the sample was determined using a Micro-BCA system (Pierce) and BSA as a concentration standard. The purity of rHMW protein was determined using conventional SDS-PAGE and commercially available silver staining reagents (Silver Stain Plus, Novex) as shown in FIG. 4.

The apparent molecular weight of the isolated mature rHMW is about 105-115 kDa as determined by SDS-PAGE.

Example 11

Preparation of Antibodies to HMW Protein

Polyvalent antisera directed against the HMW protein were generated by vaccinating rabbits with the purified HMW protein or fragments thereof. Each animal was given a total of three immunizations of about 250 ug HMW protein or fragment thereof per injection (beginning with complete Freund's adjuvant and followed with incomplete Freund's adjuvant) at approximately 21 day intervals. At each immunization, approximately half of the material was administered intramuscullarly (i.m.) and half was injected intranodally. Fourteen days after the third vaccination a fourth booster of about 100 ug HMW protein was given i.m. and the animals exsanguinated 7-10 days later. Anti-HMW protein titers were measured by ELISA using purified HMW protein (1.0 ug/well) or *C. trachomatis* $L_2$ EBs (whole and crude protein extracts) as capture ligands. Immunogen specific IgG ELISA titres of 1/320,000 were observed using purified rHMW truncated protein and 1/2500 using either EBs or RBs.

Serial dilutions of antisera were made in PBS and tested by ELISA in duplicate. Goat HRP-conjugated anti-rabbit antibody diluted 1/1000 was used as the second reporter antibody in these assays. Titers are expressed as the greatest dilution showing positive ELISA reaction, i.e. an $O.D._{450}$ value>2SD above the mean negative control value (prebleed rabbit sera). Hyperimmune antisera was then used to probe Western blots of crude EB or RB extracts as well as 1.0% OGP EB extract preparations to determine whether other *C. trachomatis* serovars and *Chlamydia* species express the HMW protein. *C. trachomatis* serovars B, F, $L_2$, MoPn and *Chlamydia pneumoniae* were tested and found to have a protein of an apparent molecular weight of 105-115 KDa reactive with antisera generated against HMW protein.

Example 12

Surface localization of the HMW protein on different *Chlamydia* strains and derivatives were examined by indirect fluorescence antibody (IFA). IFA was performed using the procedures generally known in the art using hyperimmune anti-HMW protein as the primary antibody. Hak cells infected with whole EBs from one of *C. trachomatis* serovars $L_2$, B, and F, *C. pneumoniae* or *C. psittaci* are achieved by the following method.

McCoy or Hak cells were grown to confluence in D-MEM media on 12 mmm plain coverslips inside 24 well tissue culture plates then centrifugally inoculated with ~5×10⁴ inclusion forming units (IFU) of the *C. trachomatis* strain N11 (serover F). After ~24 hours incubation, the culture media was removed and infected cells fixed inmethanol for 10 min. The fixed monoloayer was then washed with PBS (1×) to remove fixative and overlayer with >300 ul of anti-60 Kdal truncated HMWP rabbit antibody that had been diluted ⁻1/100 in PBS. After 1 hour incubation with the primary antibody, the cells were washed gently with PBS then incubated for ⁻30 min. with a 1/200 dilution of a mouse anti-rabbit IgG antibody conjugated with FITC. The second antibody was diluted using a PBS solution containing 0.0091% Evans Blue as a counter stain to visualize the monolayer. Cells were washed 2× in PBS to remove the secondary antibody, the coverslips removed from the culture plates, and mounted onto microscope slides using a fluorescent mounting medium.

Figure 7A:
FIG. 7A-B. Indirect florescence antibody staining of C. trachomatis N11 (serovar F) inclusion bodies using anti-rHMWP' antibody.
  Panel A: Post-immunization sera from rabbit K196.
    Chlamydia inclusion bodies are stained yellow.
  Panel B: Pre-immunization sera from rabbit K196.
Figure 7B:
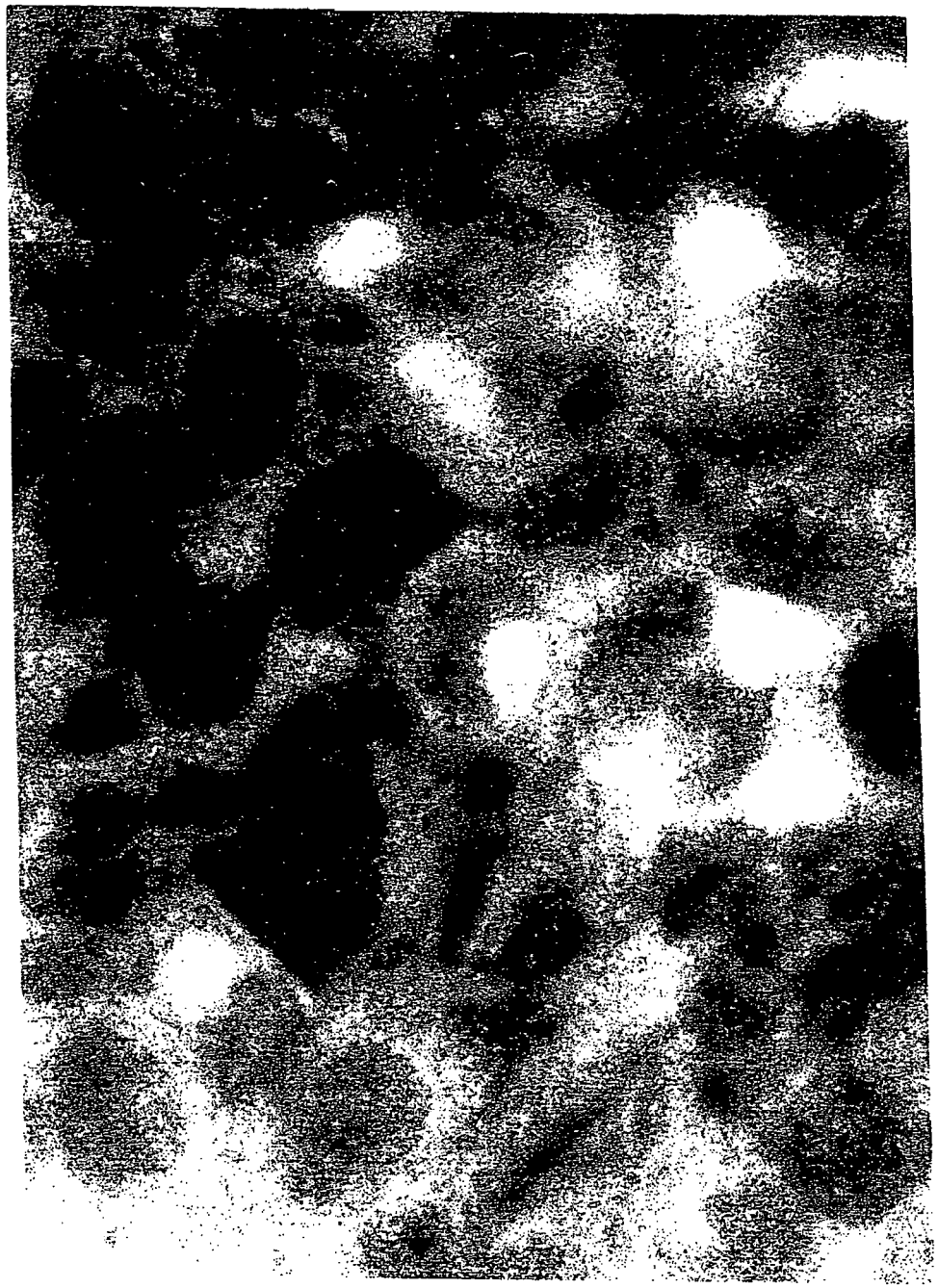

Identical cell samples stained with prebleed rabbit antibody or FITC-conjugated second antibody alone were processed in parallel and served as antibody specificity (negative) controls. Counterstained samples were examined at a 1000-× magnification with a Zeiss Axioskop photomicroscope equipped with plan-neoflur objectives. Results using $C.$ $trachomatis$ N11 (F serovar) are shown in FIG. 7A-B. The results show that enhanced fluorescence of samples stained with HMW protein antibody compared to the controls confirmed the surface location of the HMW protein. Furthermore, fluorescence of samples stained with HMW protein antibodies show binding to surface localized HMW protein from $L_2$, B and MoPn serovars and $C.$ $pneuomoniae$.

9. UTILITY

The in vitro neutralization model has been used to show that protective antiserum inhibited chlamydial infection (neutralization) of various tissue culture cell lines. Animal models are also essential for testing vaccine efficacy with both small animal (non-primate) and primate models necessary for pre-clinical evaluation. The guinea-pig has been used for studying experimental ocular and genital infection by the Guinea-pig inclusion conjunctivitis agent (GPIC), *C. psittaci.*

The mouse offers a consistent and reproducible model of genital tract infection using human genital tract isolates. This mouse model is a generally accepted pre-clinical assay, and was used to evaluate MOMP as a subunit vaccine. Another model is known as the primate model of trachoma infection wherein the induction of secretory IgA was shown to be a prime component of protection. Vaccinogenic ability of new subunit antigen candidates is determined using the above-mentioned generally accepted in vitro neutralization and animal model systems.

Example 13

In Vitro Neutralization Model

As a preliminary exercise to the animal protection studies, hyperimmune anti-HMW antibody was evaluated for its ability to block the infectivity of various *C. trachomatis* serovars (e.g. $L_2$, B, E) in vitro. Although Hela cells were used to propagate *Chlamydia*, these cells also allow antibody-mediated uptake via Fc receptors. Therefore, to evaluate anti-HMW antibody inhibition of infectivity, Hak cells, which do not display Fc receptors, were used in these analyses.

Cells were grown on coverslips in 24-well plates to a sub-confluent monolayer (about 90% confluency=$1\times10^5$ cells/ml) at 37° C. in 5% $CO_2$. Anti-HMW-antibody was diluted to about 100 ug/ml (total protein) in sucrose-phosphate-glutamate (SPG) buffer and then serially diluted in SPG buffer. Frozen aliquots of pretitered *Chlamydia* was diluted in SPG buffer to about $2\times10^4$ IFU/ml. EBs were premixed with the diluted anti-HMW-antibody to about 10-20 IFU/ul and incubated 30 minutes at 37° C. on a rocking platform.

Prepared Hak cells were washed in HBSS and then incubated with the anti-HMW-antibody/*Chlamydia* EB mixture in triplicate for each antibody using 500 IFU/ml. Plates were incubated for 2 hours at 37° C., then the inoculum removed and plates washed 3 times with HBSS. Tissue culture media containing 1 ug/ml of cyclohexamide was added and plates incubated for about 24-36 hours at 37° C. in 5% $CO_2$ to allow inclusion bodies to develop. After incubation, the media was removed and cell monolayers washed 3× in PBS. Plates were fixed in methanol for 20 minutes and re-washed in PBS.

Cells were stained to visualize inclusions by incubating with anti-*Chlamydia* LPS antibody (diluted about 1:500, ViroStat), cells washed 3 times in PBS, followed by incubation with FITC-conjugated goat secondary antibody for 30 minutes at 37° C. Coverslips were washed, air dried, and mounted in glycerol on glass coverslips. Inclusions were counted in five fields through the midline of the coverslip on a Zeiss fluorescence photomicroscope. Results are reported as the percent reduction of inclusion-containing cells with respect to a heterogenous antibody control (rabbit prebleed sera).

Example 14

Mouse Genital Infectivity Model

HMW protein is evaluated as an immunogen and a vaccinogen using the generally accepted mouse *C. trachomatis* genital infectivity model. HMW protein is evaluated as an immunogen and for the ability to protect BALB/c mice against challenge with various *C. trachomatis* serovars ($L_2$, B, E). HMW protein is administered to groups of *Chlamydia*-free animals by three different immunization routes: oral, nasal and subcutaneous. For each route, the immunogenicity of HMW protein is determined for the protein alone and in combination with an appropriate adjuvant(s). After the first immunization, animals are periodically sacrificed and serum IgG and mucosal (cervix/vagina and intestinal) sIgA 1 vels determined using well known methodologies.

Immunization of Mice: Six-to-eight week old (sexually mature), specific-pathogen free, female mice are administered with the HMW protein as described below.

For parenteral administration, the classic route for delivering recombinants subunits and toxoids to humans, HMW protein subunit is given subcutaneously to unanethesized mice. For oral immunization, animals are withdrawn from rations 4 hours before dosing. HMW protein is administered intragastrically to unanesthetized mice. Intragastrically vaccinated mice are returned to solid rations approximately 3-4 hours after immunization. Mice to be vaccinated nasally are sedated lightly, placed on their backs, and administered with HMW protein.

Determination of Serum and Mucosal Antibody Levels:

Beginning immediately after the first immunization and continuing at 7 day intervals thereafter, animals from each vaccination group are anesthetized, the abdominal cavity opened and the animal exsanguinated by cardiac puncture. Immediately thereafter, the lower reproductive tract (cervix and vagina) and small intestine are surgically removed. Mucosal secretions are collected from the intestine and cervix/vagina by gently scrapping prewashed and dissected organs with a sterile scalpel blade. Sera and mucosal secretions are stored in PBS at −70° C. until the end of the experiment and analyzed as a group.

Chlamydial IgG and secretory IgA levels in serum and mucosal secretions are determined by ELISA. Titers to both whole EB lysates and HMW protein are determined. Briefly, intact purified *C. trachomatis* $L_2$ EBs or HMW protein is diluted in 0.05 M sodium carbonate buffer and used to coat Immulon-3 (DynaTech) 96 well microtiter plates. After blocking with 1% BSA/PBS/0.05% Tween-20 and extensive washing (3×; PBS/0.05% Tween-20) serum or mucosal secretion samples, serially diluted in PBS, are added and the plate incubated at 37° C. for 1 hour. All samples are tested in duplicate. Unbound material is removed by washing. Affinity-purified HRP-conjugated to either goat anti-mouse IgA (alpha chain) or goat anti-mouse IgG (Vector Labs), diluted 1/5,000 in PBS, is then added and the plate reincubated at 37° C. for 1 hour. Secondary antibody is removed, the plate washed again and substrate (TMB) added.

The color change is measured in a microplate spectrophotometer at 450 nm after a 30 minute incubation at room temperature and quenching with $H_2SO_4$. Readings>2 SD of the mean negative control value (pooled prebleed sera, pooled mucosal secretions from unvaccinated animals) is defined as positive. Reaction specificity is monitored by preabsorbing the primary antibody with antigen (antibody-blocking) and the secondary antibody with purified mouse IgG/IgA (conjugate-blocking). Antibody titers for each data point (5 animals/point) is presented as the geometric mean±S.D. of the last positive dilution.

C. trachomatis challenge: Two weeks after the third immunization, animals are challenged intravaginally, while under mild anesthesia, with a single dose of 0.1 ml endotoxin-free PBS containing $10^8$ FU of purified, pretitered C. trachomatis EBs. Progesterone is administered (about 2.0 mg per dose, i.m.) one week prior to and the time of challenge to block estrous and ensure infection of mouse cervical epithelial cells with human C. trachomatis strains. The presence and persistence of C. trachomatis in the lower reproductive tract of vaccinated animals is assessed using both a commercial Chlamydia-specific ELISA (Chlamydiazyme, Abbott Diagnostics) and by in vitro cultivation. At 7, 14, and 21 days post-challenge, animals are sacrificed as above and their lower reproductive tracts (cervix/vagina) and small intestine surgically removed as above.

Tissue homogenates are prepared by macerating and homogenizing identical amounts of tissue in 1.0 ml SPG buffer. Clarified samples are serially diluted and tested for Chlamydia-specific antigen by commercial ELISA and used to infect McCoy cells grown to about 90% confluency in 24-well tissue culture plates. Each dilution is assayed in duplicate. After a 24 hour cultivation period, infected monolayers are fixed with methanol and inclusion bodies visualized by indirect fluorescence antibody staining using an anti-Chlamydia LPS antibody. Fluorescent inclusions are counted at a 40× magnification and the resulting titer expressed as the mean number of inclusions per 20 fields. Chlamydia IgG and sIgA levels in the serum and intestine are also determined for these animals as detailed above. Protection is defined as the ability to eliminate or reduce the level of C. trachomatis in the lower genital tract.

To determine whether vaccination with HMW protein protects mice against heterotypic challenge, equivalent groups of mice are immunized with the HMW protein and subsequently challenged with either C. trachomatis serovar B or E.

Other equivalents of the present invention may be readily determined by those skilled in the art and such equivalents are intended to be included in this invention. The foregoing disclosure includes all the information deemed essential to enable those skilled in the art to practice the claimed invention with out undue experimentation. Because the cited patents or publications may provide further useful information, all the cited materials are hereby incorporated by reference herein in their entireties.

What is claimed is:

1. A pharmaceutical composition comprising:
an isolated and substantially purified polyrertide comryising the amino acid sequence at least 95% identical to the amino acid sequence set forth as amino acids 29-533 of SEQ ID NO: 2, and a pharmaceutically acceptable carrier; wherein said composition, when administered to female mice, eliminates or reduces the level of *C. trachomatis* in the lower genital tract following intravaginal challenge.

2. The composition of claim 1, wherein said amino acid sequence comprises the amino acids 29-533 of SEQ ID NO: 2.

3. The composition of claim 2, wherein said amino acid sequence is encoded by a polynucleotide comprising the nucleotides 466 to 1980 of SEQ ID NO: 1.

4. The composition of claim 2, wherein said amino acid sequence is encoded by plasmid pJJ 36-J having ATTC Accession No. PTA-3719.

5. The composition of claim 1, wherein said amino acid sequence comprises the amino acids 29-1012 of SEQ ID NO: 2.

6. The composition of claim 5, wherein said amino acid sequence is encoded by a polynucleotide comprising the nucleotides 466-3417 of SEQ ID NO: 1.

7. The composition of claim 5, wherein said amino acid sequence comprises SEQ ID NO: 2.

8. The composition of claim 6, wherein said amino acid sequence is encoded by a polynucleotide comprising the nucleotide acid sequence SEQ ID NO: 1.

9. The composition of claim 1, wherein said amino acid is encoded by plasmid pAH342 obtainable from *E. coli* BL21 (pAH342) assigned ATCC accession number 98538.

10. The composition of claim 1, further comprising a heterologous polypeptide.

11. The composition of claim 10, wherein said heterologous polypeptide is selected from the group consisting of a pre or pro sequence, an affinity purification peptide, a heterologous immunogenic peptide, and a combination of two or more of said heterologous polypeptides.

12. The composition of claim 1, further comprising an adjuvant.

13. The composition of claim 12, wherein said adjuvant is selected from the group consisting of alum, mLT, QS21, MPS, Freund's complete adjuvant, and a combination of two or more of said adjuvants.

14. The composition of claim 1, further comprising a targeting molecule combined with or conjugated with said polypeptide.

15. The composition of claim 14, wherein the targeting molecule is selected from the group consisting of vitamin B12, bacterial toxins or fragments thereof, monoclonal antibodies, proteins, nucleic acids, carbohydrates, and a combination of two or more of said targeting molecules.

16. The composition of claim 1, which is formulated as a microparticle, a capsule, a liposome preparation, or an emulsion.

17. The composition of claim 1, wherein said polypeptide when administered to a subject induces a cellular immune response or a humoral immune response that recognizes the polypeptide of SEQ ID NO: 2.

18. A pharmaceutical composition comprising:

an isolated and substantially purified polypeptide comprising the amino acid sequence at least 95% identical to the amino acid sequence set forth as amino acids 29-533 of SEQ ID NO: 2, and a pharmaceutically acceptable carrier; wherein said polypeptide when administered to a subject induces a cellular immune response or a humoral immune response that recognizes the polypeptide of SEQ ID NO: 2.

19. The composition of claim 18, wherein said amino acid sequence comprises the amino acids 29-533 of SEQ ID NO: 2.

20. The composition of claim 19, wherein said amino acid sequence is encoded by a polynucleotide comprising the nucleotides 466 to 1980 of SEQ ID NO: 1.

21. The composition of claim 19, wherein said amino acid sequence is encoded by plasmid pJJ 36-J having ATTC Accession No. PTA-3719.

22. The composition of claim 18, wherein said amino acid sequence comprises the amino acids 29-1012 of SEQ ID NO: 2.

23. The composition of claim 22, wherein said amino acid sequence is encoded by a polynucleotide comprising the nucleotides 466-3417 of SEQ ID NO: 1.

24. The composition of claim 22, wherein said amino acid sequence comprises SEQ ID NO: 2.

25. The composition of claim 24, wherein said amino acid sequence is encoded by a polynucleotide comprising the nucleotide sequence SEQ ID NO: 1.

26. The composition of claim 18, wherein said amino acid is encoded by plasmid pAH342 obtainable from *E. coli* BL21 (pAH342) assigned ATCC accession number 98538.

27. The composition of claim 18, further comprising a heterologous polypeptide.

28. The composition of claim 27, wherein said heterologous polypeptide is selected from the group consisting of a pre or pro sequence, an affinity purification peptide, a heterologous immunogenic peptide, and a combination of two or more of said heterologous polypeptides.

29. The composition of claim 18, further comprising an adjuvant.

30. The composition of claim 29, wherein said adjuvant is selected from the group consisting of alum, mLT, QS21, MPS, Freund's complete adjuvant, and a combination of two or more of said adjuvants.

31. The composition of claim 18, further comprising a targeting molecule combined with or conjugated with said polypeptide.

32. The composition of claim 31, wherein the targeting molecule is selected from the group consisting of vitamin B12, bacterial toxins or fragments thereof, monoclonal antibodies, proteins, nucleic acids, carbohydrates, and a combination of two or more of said targeting molecules.

33. The composition of claim 18, which is formulated as a microparticle, a capsule, a liposome preparation, or an emulsion.

34. The composition of claim 18, wherein said composition, when administered to female mice, eliminates or reduces the level of *C. trachomatis* in the lower genital tract following intravaginal challenge.

* * * * *

SEQUENCE LISTING

```
<160> NUMBER OF SEQ ID NOS: 43

<210> SEQ ID NO 1
<211> LENGTH: 4435
<212> TYPE: DNA
<213> ORGANISM: Artificial Sequence
<220> FEATURE:
<223> OTHER INFORMATION: Description of Artificial Sequence: Recombinant
                         Expression Vector
<220> FEATURE:
<221> NAME/KEY: CDS
<222> LOCATION: (382)..(3417)
<223> OTHER INFORMATION:

<400> SEQUENCE: 1
gggcaaaact cttccccccg ggatttatat gggaaagggg aaactttggc ccgtattcaa      60
gcgccacggg ttttggggcg gaatgaattt tttcgttccg gaaaaagtaa ttccccggga     120
acgtagggta tcggtttcat aggctcgcca aatgggatat aggtggaaag gtaaaaaaaa     180
ctgagccaag caaaggatag agaagtcttg taatcatcgc aggttaaagg ggggatgtta     240
ttttagcctg caaatagtgt aattattgga tcctgtaaag agaaaaggac gaatgcgctg     300
aagataagaa catttattga tattaaatta ttaatttttt atgaagcgga gtaattaatt     360
ttatctctca gcttttgtgt g atg caa acg tct ttc cat aag ttc ttt ctt       411
                        Met Gln Thr Ser Phe His Lys Phe Phe Leu
                        1               5                   10
```

-continued

| | | | | | | | | | | | | | | | |
|---|---|---|---|---|---|---|---|---|---|---|---|---|---|---|---|
| tca | atg | att | cta | gct | tat | tct | tgc | tgc | tct | tta | aat | ggg | ggg | gga | tat | 459 |
| Ser | Met | Ile | Leu | Ala | Tyr | Ser | Cys | Cys | Ser | Leu | Asn | Gly | Gly | Gly | Tyr | |
| | | | 15 | | | | 20 | | | | | | 25 | | | |

| gca | gca | gaa | atc | atg | gtt | cct | caa | gga | att | tac | gat | ggg | gag | acg | tta | 507 |
| Ala | Ala | Glu | Ile | Met | Val | Pro | Gln | Gly | Ile | Tyr | Asp | Gly | Glu | Thr | Leu | |
| | 30 | | | | | 35 | | | | | 40 | | | | | |

| act | gta | tca | ttt | ccc | tat | act | gtt | ata | gga | gat | ccg | agt | ggg | act | act | 555 |
| Thr | Val | Ser | Phe | Pro | Tyr | Thr | Val | Ile | Gly | Asp | Pro | Ser | Gly | Thr | Thr | |
| | 45 | | | | | 50 | | | | | 55 | | | | | |

| gtt | ttt | tct | gca | gga | gag | tta | aca | tta | aaa | aat | ctt | gac | aat | tct | att | 603 |
| Val | Phe | Ser | Ala | Gly | Glu | Leu | Thr | Leu | Lys | Asn | Leu | Asp | Asn | Ser | Ile | |
| 60 | | | | | 65 | | | | | 70 | | | | | | |

| gca | gct | ttg | cct | tta | agt | tgt | ttt | ggg | aac | tta | tta | ggg | agt | ttt | act | 651 |
| Ala | Ala | Leu | Pro | Leu | Ser | Cys | Phe | Gly | Asn | Leu | Leu | Gly | Ser | Phe | Thr | |
| 75 | | | | 80 | | | | | 85 | | | | | 90 | | |

| gtt | tta | ggg | aga | gga | cac | tcg | ttg | act | ttc | gag | aac | ata | cgg | act | tct | 699 |
| Val | Leu | Gly | Arg | Gly | His | Ser | Leu | Thr | Phe | Glu | Asn | Ile | Arg | Thr | Ser | |
| | | | | 95 | | | | | 100 | | | | | 105 | | |

| aca | aat | ggg | gca | gct | cta | agt | aat | agc | gct | gct | gat | gga | ctg | ttt | act | 747 |
| Thr | Asn | Gly | Ala | Ala | Leu | Ser | Asn | Ser | Ala | Ala | Asp | Gly | Leu | Phe | Thr | |
| | | 110 | | | | | 115 | | | | | 120 | | | | |

| att | gag | ggt | ttt | aaa | gaa | tta | tcc | ttt | tcc | aat | tgc | aat | tca | tta | ctt | 795 |
| Ile | Glu | Gly | Phe | Lys | Glu | Leu | Ser | Phe | Ser | Asn | Cys | Asn | Ser | Leu | Leu | |
| | | | 125 | | | | | 130 | | | | | 135 | | | |

| gcc | gta | ctg | cct | gct | gca | acg | act | aat | aag | ggt | agc | cag | act | ccg | acg | 843 |
| Ala | Val | Leu | Pro | Ala | Ala | Thr | Thr | Asn | Lys | Gly | Ser | Gln | Thr | Pro | Thr | |
| | 140 | | | | | 145 | | | | | 150 | | | | | |

| aca | aca | tct | aca | ccg | tct | aat | ggt | act | att | tat | tct | aaa | aca | gat | ctt | 891 |
| Thr | Thr | Ser | Thr | Pro | Ser | Asn | Gly | Thr | Ile | Tyr | Ser | Lys | Thr | Asp | Leu | |
| 155 | | | | | 160 | | | | | 165 | | | | | 170 | |

| ttg | tta | ctc | aat | aat | gag | aag | ttc | tca | ttc | tat | agt | aat | tta | gtc | tct | 939 |
| Leu | Leu | Leu | Asn | Asn | Glu | Lys | Phe | Ser | Phe | Tyr | Ser | Asn | Leu | Val | Ser | |
| | | | | 175 | | | | | 180 | | | | | 185 | | |

| gga | gat | ggg | gga | gct | ata | gat | gct | aag | agc | tta | acg | gtt | caa | gga | att | 987 |
| Gly | Asp | Gly | Gly | Ala | Ile | Asp | Ala | Lys | Ser | Leu | Thr | Val | Gln | Gly | Ile | |
| | | | 190 | | | | | 195 | | | | | 200 | | | |

| agc | aag | ctt | tgt | gtc | ttc | caa | gaa | aat | act | gct | caa | gct | gat | ggg | gga | 1035 |
| Ser | Lys | Leu | Cys | Val | Phe | Gln | Glu | Asn | Thr | Ala | Gln | Ala | Asp | Gly | Gly | |
| | 205 | | | | | 210 | | | | | 215 | | | | | |

| gct | tgt | caa | gta | gtc | acc | agt | ttc | tct | gct | atg | gct | aac | gag | gct | cct | 1083 |
| Ala | Cys | Gln | Val | Val | Thr | Ser | Phe | Ser | Ala | Met | Ala | Asn | Glu | Ala | Pro | |
| 220 | | | | | 225 | | | | | 230 | | | | | | |

| att | gcc | ttt | gta | gcg | aat | gtt | gca | gga | gta | aga | ggg | gga | ggg | att | gct | 1131 |
| Ile | Ala | Phe | Val | Ala | Asn | Val | Ala | Gly | Val | Arg | Gly | Gly | Gly | Ile | Ala | |
| 235 | | | | 240 | | | | | 245 | | | | | 250 | | |

| gct | gtt | cag | gat | ggg | cag | cag | gga | gtg | tca | tca | tct | act | tca | aca | gaa | 1179 |
| Ala | Val | Gln | Asp | Gly | Gln | Gln | Gly | Val | Ser | Ser | Ser | Thr | Ser | Thr | Glu | |
| | | | | 255 | | | | | 260 | | | | | 265 | | |

| gat | cca | gta | gta | agt | ttt | tcc | aga | aat | act | gcg | gta | gag | ttt | gat | ggg | 1227 |
| Asp | Pro | Val | Val | Ser | Phe | Ser | Arg | Asn | Thr | Ala | Val | Glu | Phe | Asp | Gly | |
| | | | 270 | | | | | 275 | | | | | 280 | | | |

| aac | gta | gcc | cga | gta | gga | gga | ggg | att | tac | tcc | tac | ggg | aac | gtt | gct | 1275 |
| Asn | Val | Ala | Arg | Val | Gly | Gly | Gly | Ile | Tyr | Ser | Tyr | Gly | Asn | Val | Ala | |
| | | 285 | | | | | 290 | | | | | 295 | | | | |

| ttc | ctg | aat | aat | gga | aaa | acc | ttg | ttt | ctc | aac | aat | gtt | gct | tct | cct | 1323 |
| Phe | Leu | Asn | Asn | Gly | Lys | Thr | Leu | Phe | Leu | Asn | Asn | Val | Ala | Ser | Pro | |
| | | | 300 | | | | | 305 | | | | | 310 | | | |

| gtt | tac | att | gct | gct | aag | caa | cca | aca | agt | gga | cag | gct | tct | aat | acg | 1371 |
| Val | Tyr | Ile | Ala | Ala | Lys | Gln | Pro | Thr | Ser | Gly | Gln | Ala | Ser | Asn | Thr | |
| 315 | | | | | 320 | | | | | 325 | | | | | 330 | |

```
agt aat aat tac gga gat gga gga gct atc ttc tgt aag aat ggt gcg    1419
Ser Asn Asn Tyr Gly Asp Gly Gly Ala Ile Phe Cys Lys Asn Gly Ala
                335                 340                 345 caa gca gga tcc aat aac tct gga tca gtt tcc ttt gat gga gag gga    1467
Gln Ala Gly Ser Asn Asn Ser Gly Ser Val Ser Phe Asp Gly Glu Gly
            350                 355                 360 gta gtt ttc ttt agt agc aat gta gct gct ggg aaa ggg gga gct att    1515
Val Val Phe Phe Ser Ser Asn Val Ala Ala Gly Lys Gly Gly Ala Ile
        365                 370                 375 tat gcc aaa aag ctc tcg gtt gct aac tgt ggc cct gta caa ttt tta    1563
Tyr Ala Lys Lys Leu Ser Val Ala Asn Cys Gly Pro Val Gln Phe Leu
    380                 385                 390 agg aat atc gct aat gat ggt gga gcg att tat tta gga gaa tct gga    1611
Arg Asn Ile Ala Asn Asp Gly Gly Ala Ile Tyr Leu Gly Glu Ser Gly
395                 400                 405                 410 gag ctc agt tta tct gct gat tat gga gat att att ttc gat ggg aat    1659
Glu Leu Ser Leu Ser Ala Asp Tyr Gly Asp Ile Ile Phe Asp Gly Asn
                415                 420                 425 ctt aaa aga aca gcc aaa gag aat gct gcc gat gtt aat ggc gta act    1707
Leu Lys Arg Thr Ala Lys Glu Asn Ala Ala Asp Val Asn Gly Val Thr
            430                 435                 440 gtg tcc tca caa gcc att tcg atg gga tcg gga ggg aaa ata acg aca    1755
Val Ser Ser Gln Ala Ile Ser Met Gly Ser Gly Gly Lys Ile Thr Thr
        445                 450                 455 tta aga gct aaa gca ggg cat cag att ctc ttt aat gat ccc atc gag    1803
Leu Arg Ala Lys Ala Gly His Gln Ile Leu Phe Asn Asp Pro Ile Glu
    460                 465                 470 atg gca aac gga aat aac cag cca gcg cag tct tcc aaa ctt cta aaa    1851
Met Ala Asn Gly Asn Asn Gln Pro Ala Gln Ser Ser Lys Leu Leu Lys
475                 480                 485                 490 att aac gat ggt gaa gga tac aca ggg gat att gtt ttt gct aat gga    1899
Ile Asn Asp Gly Glu Gly Tyr Thr Gly Asp Ile Val Phe Ala Asn Gly
                495                 500                 505 agc agt act ttg tac caa aat gtt acg ata gag caa gga agg att gtt    1947
Ser Ser Thr Leu Tyr Gln Asn Val Thr Ile Glu Gln Gly Arg Ile Val
            510                 515                 520 ctt cgt gaa aag gca aaa tta tca gtg aat tct cta agt cag aca ggt    1995
Leu Arg Glu Lys Ala Lys Leu Ser Val Asn Ser Leu Ser Gln Thr Gly
        525                 530                 535 ggg agt ctg tat atg gaa gct ggg agt aca tgg gat ttt gta act cca    2043
Gly Ser Leu Tyr Met Glu Ala Gly Ser Thr Trp Asp Phe Val Thr Pro
    540                 545                 550 caa cca cca caa cag cct cct gcc gct aat cag ttg atc acg ctt tcc    2091
Gln Pro Pro Gln Gln Pro Pro Ala Ala Asn Gln Leu Ile Thr Leu Ser
555                 560                 565                 570 aat ctg cat ttg tct ctt tct tct ttg tta gca aac aat gca gtt acg    2139
Asn Leu His Leu Ser Leu Ser Ser Leu Leu Ala Asn Asn Ala Val Thr
                575                 580                 585 aat cct cct acc aat cct cca gcg caa gat tct cat cct gca gtc att    2187
Asn Pro Pro Thr Asn Pro Pro Ala Gln Asp Ser His Pro Ala Val Ile
            590                 595                 600 ggt agc aca act gct ggt tct gtt aca att agt ggg cct atc ttt ttt    2235
Gly Ser Thr Thr Ala Gly Ser Val Thr Ile Ser Gly Pro Ile Phe Phe
        605                 610                 615 gag gat ttg gat gat aca gct tat gat agg tat gat tgg cta ggt tct    2283
Glu Asp Leu Asp Asp Thr Ala Tyr Asp Arg Tyr Asp Trp Leu Gly Ser
    620                 625                 630 aat caa aaa atc aat gtc ctg aaa tta cag tta ggg act aag ccc cca    2331
Asn Gln Lys Ile Asn Val Leu Lys Leu Gln Leu Gly Thr Lys Pro Pro
```

| | | | | | | | | | | | | | | | | |
|---|---|---|---|---|---|---|---|---|---|---|---|---|---|---|---|---|
| | | | 635 | | | | 640 | | | | 645 | | | | 650 | |

```
gct aat gcc cca tca gat ttg act cta ggg aat gag atg cct aag tat      2379
Ala Asn Ala Pro Ser Asp Leu Thr Leu Gly Asn Glu Met Pro Lys Tyr
                655                 660                 665 ggc tat caa gga agc tgg aag ctt gcg tgg gat cct aat aca gca aat      2427
Gly Tyr Gln Gly Ser Trp Lys Leu Ala Trp Asp Pro Asn Thr Ala Asn
            670                 675                 680 aat ggt cct tat act ctg aaa gct aca tgg act aaa act ggg tat aat      2475
Asn Gly Pro Tyr Thr Leu Lys Ala Thr Trp Thr Lys Thr Gly Tyr Asn
                685                 690                 695 cct ggg cct gag cga gta gct tct ttg gtt cca aat agt tta tgg gga      2523
Pro Gly Pro Glu Arg Val Ala Ser Leu Val Pro Asn Ser Leu Trp Gly
700                 705                 710 tcc att tta gat ata cga tct gcg cat tca gca att caa gca agt gtg      2571
Ser Ile Leu Asp Ile Arg Ser Ala His Ser Ala Ile Gln Ala Ser Val
715                 720                 725                 730 gat ggg cgc tct tat tgt cga gga tta tgg gtt tct gga gtt tcg aat      2619
Asp Gly Arg Ser Tyr Cys Arg Gly Leu Trp Val Ser Gly Val Ser Asn
                735                 740                 745 ttc ttc tat cat gac cgc gat gct tta ggt cag gga tat cgg tat att      2667
Phe Phe Tyr His Asp Arg Asp Ala Leu Gly Gln Gly Tyr Arg Tyr Ile
            750                 755                 760 agt ggg ggt tat tcc tta gga gca aac tcc tac ttt gga tca tcg atg      2715
Ser Gly Gly Tyr Ser Leu Gly Ala Asn Ser Tyr Phe Gly Ser Ser Met
                765                 770                 775 ttt ggt cta gca ttt acc gaa gta ttt ggt aga tct aaa gat tat gta      2763
Phe Gly Leu Ala Phe Thr Glu Val Phe Gly Arg Ser Lys Asp Tyr Val
780                 785                 790 gtg tgt cgt tcc aat cat cat gct tgc ata gga tcc gtt tat cta tct      2811
Val Cys Arg Ser Asn His His Ala Cys Ile Gly Ser Val Tyr Leu Ser
795                 800                 805                 810 acc caa caa gct tta tgt gga tcc tat ttg ttc gga gat gcg ttt atc      2859
Thr Gln Gln Ala Leu Cys Gly Ser Tyr Leu Phe Gly Asp Ala Phe Ile
                815                 820                 825 cgt gct agc tac ggg ttt ggg aat cag cat atg aaa acc tca tat aca      2907
Arg Ala Ser Tyr Gly Phe Gly Asn Gln His Met Lys Thr Ser Tyr Thr
            830                 835                 840 ttt gca gag gag agc gat gtt cgt tgg gat aat aac tgt ctg gct gga      2955
Phe Ala Glu Glu Ser Asp Val Arg Trp Asp Asn Asn Cys Leu Ala Gly
                845                 850                 855 gag att gga gcg gga tta ccg att gtg att act cca tct aag ctc tat      3003
Glu Ile Gly Ala Gly Leu Pro Ile Val Ile Thr Pro Ser Lys Leu Tyr
860                 865                 870 ttg aat gag ttg cgt cct ttc gtg caa gct gag ttt tct tat gcc gat      3051
Leu Asn Glu Leu Arg Pro Phe Val Gln Ala Glu Phe Ser Tyr Ala Asp
875                 880                 885                 890 cat gaa tct ttt aca gag gaa ggc gat caa gct cgg gca ttc aag agc      3099
His Glu Ser Phe Thr Glu Glu Gly Asp Gln Ala Arg Ala Phe Lys Ser
                895                 900                 905 gga cat ctc cta aat cta tca gtt cct gtt gga gtg aag ttt gat cga      3147
Gly His Leu Leu Asn Leu Ser Val Pro Val Gly Val Lys Phe Asp Arg
            910                 915                 920 tgt tct agt aca cat cct aat aaa tat agc ttt atg gcg gct tat atc      3195
Cys Ser Ser Thr His Pro Asn Lys Tyr Ser Phe Met Ala Ala Tyr Ile
                925                 930                 935 tgt gat gct tat cgc acc atc tct ggt act gag aca acg ctc cta tcc      3243
Cys Asp Ala Tyr Arg Thr Ile Ser Gly Thr Glu Thr Thr Leu Leu Ser
940                 945                 950 cat caa gag aca tgg aca aca gat gcc ttt cat tta gca aga cat gga      3291
```

-continued

| His Gln Glu Thr Trp Thr Thr Asp Ala Phe His Leu Ala Arg His Gly | |
|---|---|
| 955         960             965             970 | |

```
gtt gtg gtt aga gga tct atg tat gct tct cta aca agt aat ata gaa    3339
Val Val Val Arg Gly Ser Met Tyr Ala Ser Leu Thr Ser Asn Ile Glu
            975             980             985 gta tat ggc cat gga aga tat gag tat cga gat gct tct cga  ggc tat   3387
Val Tyr Gly His Gly Arg Tyr Glu Tyr Arg Asp Ala Ser Arg  Gly Tyr
        990             995             1000 ggt ttg agt  gca gga agt aga gtc  cgg ttc taaaaatatt ggttagatag    3437
Gly Leu Ser  Ala Gly Ser Arg Val  Arg Phe
        1005             1010 ttaagtgtta gcgatgcctt tttctttgag atctacatca ttttgttttt tagcttgttt    3497
gtgttcctat tcgtatggat tcgcgagctc tcctcaagtg ttaacgccta atgtaaccac    3557
tccttttaag ggagacgatg tttacttgaa tggagactgc gcttttgtca atgtctatgc    3617
aggagctgaa gaaggttcga ttatctcagc taatggcgac aatttaacga ttaccggaca    3677
aaaccataca ttatcattta cagattctca agggccagtt cttcaaaatt atgccttcat    3737
ttcagcagga gagacactta ctctgagaga tttttcgagt ctgatgttct cgaaaaatgt    3797
ttcttgcgga gaaaagggaa tgatctccgg gaaaaccgtg agtatttccg gagcaggcga    3857
agtgattttc tgggataact ccgtggggta ttctccttta tctactgtgc caacctcatc    3917
atcaactccg cctgctccaa cagttagtga tgctcggaaa gggtctattt tttctgtaga    3977
gactagtttg gagatctcag gcgtcaaaaa agggtcatg ttcgataata atgccgggaa     4037
tttcggaaca gttttcgag gtaagaataa taataatgct ggtggtggag cagtgggtt      4097
ccgctacacc atcaagtacg acttttacag ttaaaaactg taaagggaaa gtttctttca    4157
cagataacgt agcctcttgc ggaggcgag tggtttataa aggcattgtg cttttcaaag     4217
acaatgaagg aggcatattc ttccgaggga acacagcata cgatgattta aggattcttg    4277
ctgctactaa tcaggatcag aatacggaga caggaggcgg tggaggagtt atttgctctc    4337
cagatgattc tgtaaagttt gaaggcaata aaggttctat tgtttttgat tacaactttg    4397
caaaaggcag aggcggaagc atcctaacga aagaattc                             4435
```

<210> SEQ ID NO 2
<211> LENGTH: 1012
<212> TYPE: PRT
<213> ORGANISM: Chlamydia sp.

<400> SEQUENCE: 2

Met Gln Thr Ser Phe His Lys Phe Phe Leu Ser Met Ile Leu Ala Tyr
1               5                   10                  15

Ser Cys Cys Ser Leu Asn Gly Gly Gly Tyr Ala Ala Glu Ile Met Val
            20                  25                  30

Pro Gln Gly Ile Tyr Asp Gly Glu Thr Leu Thr Val Ser Phe Pro Tyr
        35                  40                  45

Thr Val Ile Gly Asp Pro Ser Gly Thr Thr Val Phe Ser Ala Gly Glu
    50                  55                  60

Leu Thr Leu Lys Asn Leu Asp Asn Ser Ile Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
            100                 105                 110

Ser Asn Ser Ala Ala Asp Gly Leu Phe Thr Ile Glu Gly Phe Lys Glu

-continued

```
            115                 120                 125
Leu Ser Phe Ser Asn Cys Asn Ser Leu Leu Ala Val Leu Pro Ala Ala
        130                 135                 140

Thr Thr Asn Lys Gly Ser Gln Thr Pro Thr Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Leu Val Ser Gly Asp Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
        210                 215                 220

Ser Phe Ser Ala Met Ala Asn Glu Ala Pro Ile Ala Phe Val Ala Asn
225                 230                 235                 240

Val Ala Gly Val Arg Gly Gly Gly Ile Ala Ala Val Gln Asp Gly Gln
                245                 250                 255

Gln Gly Val Ser Ser Ser Thr Ser Thr Glu Asp Pro Val Val Ser Phe
            260                 265                 270

Ser Arg Asn Thr Ala Val Glu Phe Asp Gly Asn Val Ala Arg Val Gly
            275                 280                 285

Gly Gly Ile Tyr Ser Tyr Gly Asn Val Ala Phe Leu Asn Asn Gly Lys
        290                 295                 300

Thr Leu Phe Leu Asn Asn Val Ala Ser Pro Val Tyr Ile Ala Ala Lys
305                 310                 315                 320

Gln Pro Thr Ser Gly Gln Ala Ser Asn Thr Ser Asn Asn Tyr Gly Asp
                325                 330                 335

Gly Gly Ala Ile Phe Cys Lys Asn Gly Ala Gln Ala Gly Ser Asn Asn
            340                 345                 350

Ser Gly Ser Val Ser Phe Asp Gly Glu Gly Val Val Phe Phe Ser Ser
        355                 360                 365

Asn Val Ala Ala Gly Lys Gly Gly Ala Ile Tyr Ala Lys Lys Leu Ser
        370                 375                 380

Val Ala Asn Cys Gly Pro Val Gln Phe Leu Arg Asn Ile Ala Asn Asp
385                 390                 395                 400

Gly Gly Ala Ile Tyr Leu Gly Glu Ser Gly Glu Leu Ser Leu Ser Ala
                405                 410                 415

Asp Tyr Gly Asp Ile Ile Phe Asp Gly Asn Leu Lys Arg Thr Ala Lys
            420                 425                 430

Glu Asn Ala Ala Asp Val Asn Gly Val Thr Val Ser Ser Gln Ala Ile
        435                 440                 445

Ser Met Gly Ser Gly Gly Lys Ile Thr Thr Leu Arg Ala Lys Ala Gly
        450                 455                 460

His Gln Ile Leu Phe Asn Asp Pro Ile Glu Met Ala Asn Gly Asn Asn
465                 470                 475                 480

Gln Pro Ala Gln Ser Ser Lys Leu Leu Lys Ile Asn Asp Gly Glu Gly
                485                 490                 495

Tyr Thr Gly Asp Ile Val Phe Ala Asn Gly Ser Ser Thr Leu Tyr Gln
            500                 505                 510

Asn Val Thr Ile Glu Gln Gly Arg Ile Val Leu Arg Glu Lys Ala Lys
        515                 520                 525

Leu Ser Val Asn Ser Leu Ser Gln Thr Gly Gly Ser Leu Tyr Met Glu
        530                 535                 540
```

```
Ala Gly Ser Thr Trp Asp Phe Val Thr Pro Gln Pro Gln Gln Pro
545                 550                 555                 560

Pro Ala Ala Asn Gln Leu Ile Thr Leu Ser Asn Leu His Leu Ser Leu
                565                 570                 575

Ser Ser Leu Leu Ala Asn Asn Ala Val Thr Asn Pro Pro Thr Asn Pro
            580                 585                 590

Pro Ala Gln Asp Ser His Pro Ala Val Ile Gly Ser Thr Thr Ala Gly
            595                 600                 605

Ser Val Thr Ile Ser Gly Pro Ile Phe Phe Glu Asp Leu Asp Asp Thr
        610                 615                 620

Ala Tyr Asp Arg Tyr Asp Trp Leu Gly Ser Asn Gln Lys Ile Asn Val
625                 630                 635                 640

Leu Lys Leu Gln Leu Gly Thr Lys Pro Pro Ala Asn Ala Pro Ser Asp
                645                 650                 655

Leu Thr Leu Gly Asn Glu Met Pro Lys Tyr Gly Tyr Gln Gly Ser Trp
            660                 665                 670

Lys Leu Ala Trp Asp Pro Asn Thr Ala Asn Asn Gly Pro Tyr Thr Leu
            675                 680                 685

Lys Ala Thr Trp Thr Lys Thr Gly Tyr Asn Pro Gly Pro Glu Arg Val
690                 695                 700

Ala Ser Leu Val Pro Asn Ser Leu Trp Gly Ser Ile Leu Asp Ile Arg
705                 710                 715                 720

Ser Ala His Ser Ala Ile Gln Ala Ser Val Asp Gly Arg Ser Tyr Cys
                725                 730                 735

Arg Gly Leu Trp Val Ser Gly Val Ser Asn Phe Phe Tyr His Asp Arg
            740                 745                 750

Asp Ala Leu Gly Gln Gly Tyr Arg Tyr Ile Ser Gly Tyr Ser Leu
            755                 760                 765

Gly Ala Asn Ser Tyr Phe Gly Ser Ser Met Phe Gly Leu Ala Phe Thr
        770                 775                 780

Glu Val Phe Gly Arg Ser Lys Asp Tyr Val Val Cys Arg Ser Asn His
785                 790                 795                 800

His Ala Cys Ile Gly Ser Val Tyr Leu Ser Thr Gln Ala Leu Cys
                805                 810                 815

Gly Ser Tyr Leu Phe Gly Asp Ala Phe Ile Arg Ala Ser Tyr Gly Phe
            820                 825                 830

Gly Asn Gln His Met Lys Thr Ser Tyr Thr Phe Ala Glu Glu Ser Asp
            835                 840                 845

Val Arg Trp Asp Asn Asn Cys Leu Ala Gly Glu Ile Gly Ala Gly Leu
850                 855                 860

Pro Ile Val Ile Thr Pro Ser Lys Leu Tyr Leu Asn Glu Leu Arg Pro
865                 870                 875                 880

Phe Val Gln Ala Glu Phe Ser Tyr Ala Asp His Glu Ser Phe Thr Glu
                885                 890                 895

Glu Gly Asp Gln Ala Arg Ala Phe Lys Ser Gly His Leu Leu Asn Leu
            900                 905                 910

Ser Val Pro Val Gly Val Lys Phe Asp Arg Cys Ser Ser Thr His Pro
        915                 920                 925

Asn Lys Tyr Ser Phe Met Ala Ala Tyr Ile Cys Asp Ala Tyr Arg Thr
        930                 935                 940

Ile Ser Gly Thr Glu Thr Thr Leu Leu Ser His Gln Glu Thr Trp Thr
945                 950                 955                 960
```

-continued

```
Thr Asp Ala Phe His Leu Ala Arg His Gly Val Val Arg Gly Ser
                965                 970                 975

Met Tyr Ala Ser Leu Thr Ser Asn Ile Glu Val Tyr Gly His Gly Arg
            980                 985                 990

Tyr Glu Tyr Arg Asp Ala Ser Arg  Gly Tyr Gly Leu Ser  Ala Gly Ser
        995                 1000                1005

Arg Val  Arg Phe
    1010

<210> SEQ ID NO 3
<211> LENGTH: 20
<212> TYPE: PRT
<213> ORGANISM: Chlamydia sp.
<220> FEATURE:
<221> NAME/KEY: SITE
<222> LOCATION: 19
<223> OTHER INFORMATION: Xaa=unknown amino acid

<400> SEQUENCE: 3

Glu Ile Met Val Pro Gln Gly Ile Tyr Asp Gly Glu Thr Leu Thr Val
1               5                   10                  15

Ser Phe Xaa Tyr
            20

<210> SEQ ID NO 4
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 4
gaaathatgg tnccncaa                                                18

<210> SEQ ID NO 5
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 5
gaaathatgg tnccncag                                                18

<210> SEQ ID NO 6
<211> LENGTH: 18
<212> TYPE: DNA
<213> ORGANISM: Chlamydia sp.
<220> FEATURE:
<221> NAME/KEY: modified_base
<222> LOCATION: 12, 15
<223> OTHER INFORMATION: n = a, t, g, or c

<400> SEQUENCE: 6
gagathatgg tnccncaa                                                18

<210> SEQ ID NO 7
<211> LENGTH: 18
<212> TYPE: DNA
<213> ORGANISM: Chlamydia sp.
<220> FEATURE:
<221> NAME/KEY: modified_base
```

```
<222> LOCATION: 12, 15
<223> OTHER INFORMATION: n = a, t, g, or c

<400> SEQUENCE: 7
gagathatgg tnccncag                                                    18

<210> SEQ ID NO 8
<211> LENGTH: 15
<212> TYPE: DNA
<213> ORGANISM: Chlamydia sp.
<220> FEATURE:
<221> NAME/KEY: modified_base
<222> LOCATION: 1, 7
<223> OTHER INFORMATION: n = a, t, g, or c

<400> SEQUENCE: 8
ngtytcnccr tcata                                                       15

<210> SEQ ID NO 9
<211> LENGTH: 15
<212> TYPE: DNA
<213> ORGANISM: Chlamydia sp.
<220> FEATURE:
<221> NAME/KEY: modified_base
<222> LOCATION: 1, 7
<223> OTHER INFORMATION: n = a, t, g, or c

<400> SEQUENCE: 9
ngtytcnccr tcgta                                                       15

<210> SEQ ID NO 10
<211> LENGTH: 1511
<212> TYPE: DNA
<213> ORGANISM: Chlamydia sp.

<400> SEQUENCE: 10
gaaatcatgg ttcctcaagg aatttacgat ggggagacgt taactgtatc atttccctat        60
actgttatag gagatccgag tgggactact gttttttctg caggagagtt aacattaaaa       120
aatcttgaca attctattgc agctttgcct ttaagttgtt tgggaacttt attagggagt       180
tttactgttt tagggagagg acactcgttg actttcgaga acatacggac ttctacaaat       240 gggggcagctc taagtaatag cgctgctgat ggactgttta ctattgaggg ttttaaagaa      300
ttatcctttt ccaattgcaa ttcattactt gccgtactgc ctgctgcaac gactaataag       360
ggtagccaga ctccgacgac aacatctaca ccgtctaatg gtactattta ttctaaaaca       420
gatcttttgt tactcaataa tgagaagttc tcattctata gtaatttagt ctctggagat       480
gggggagcta tagtgctaa gagcttaacg gttcaaggaa ttagcaagct ttgtgtcttc        540
caagaaaata ctgctcaagc tgatggggga gcttgtcaag tagtcaccag tttctctgct       600
atggctaacg aggctcctat tgcctttgta gcgaatgttg caggagtaag aggggagggg       660
attgctgctg ttcaggatgg gcagcaggga gtgtcatcat ctacttcaac agaagatcca       720
gtagtaagtt tttccagaaa tactgcggta gagtttgatg gaacgtagc ccgagtagga        780 ggagggattt actcctacgg gaacgttgct ttcctgaata atggaaaaac cttgtttctc       840
aacaatgttg cttctcctgt ttacattgct gctaagcaac caacaagtgg acaggcttct       900
aatacgagta ataattacgg agatggagga gctatcttct gtaagaatgg tgcgcaagca       960
ggatccaata actctggatc agtttccttt gatggagagg gagtagtttt ctttagtagc      1020
aatgtagctg ctgggaaagg gggagctatt tatgccaaaa agctctcggt tgctaactgt      1080
```

```
ggccctgtac aattttttaag gaatatcgct aatgatggtg gagcgattta tttaggagaa    1140
tctggagagc tcagtttatc tgctgattat ggagatatta ttttcgatgg gaatcttaaa    1200
agaacagcca aagagaatgc tgccgatgtt aatggcgtaa ctgtgtcctc acaagccatt    1260
tcgatgggat cgggagggaa aataacgaca ttaagagcta aagcagggca tcagattctc    1320
tttaatgatc ccatcgagat ggcaaacgga aataaccagc cagcgcagtc ttccaaactt    1380
ctaaaaatta acgatggtga aggatacaca ggggatattg ttttgctaa tggaagcagt    1440 actttgtacc aaaatgttac gatagagcaa ggaaggattg ttcttcgtga aaaggcaaaa    1500
ttatcagtga a                                                         1511

<210> SEQ ID NO 11
<211> LENGTH: 1444
<212> TYPE: DNA
<213> ORGANISM: Chlamydia sp.

<400> SEQUENCE: 11
ttctctaagt cagacaggtg ggagtctgta tatggaagct gggagtacat gggattttgt      60
aactccacaa ccaccacaac agcctcctgc cgctaatcag ttgatcacgc tttccaatct     120
gcatttgtct cttcttcttc tgttagcaaa caatgcagtt acgaatcctc ctaccaatcc     180
tccagcgcaa gattctcatc ctgcagtcat tggtagcaca actgctggtt ctgttacaat     240
tagtgggcct atcttttttg aggatttgga tgatacagct tatgataggt atgattggct     300
aggttctaat caaaaaatca atgtcctgaa attacagtta gggactaagc ccccagctaa     360
tgccccatca gatttgactc tagggaatga gatgcctaag tatggctatc aaggaagctg     420
gaagcttgcg tgggatccta atacagcaaa taatggtcct tatactctga agctacatg      480 gactaaaact gggtataatc ctgggcctga gcgagtagct tctttggttc caaatagttt     540
atggggatcc atttagata tacgatctgc gcattcagca attcaagcaa gtgtggatgg      600
gcgctcttat tgtcgaggat tatgggtttc tggagtttcg aatttcttct atcatgaccg     660
cgatgcttta ggtcagggat atcggtatat tagtgggggt tattccttag agcaaaactc     720
ctactttgga tcatcgatgt ttggtctagc atttaccgaa gtatttggta gatctaaaga     780
ttatgtagtg tgtcgttcca atcatcatgc ttgcatagga tccgtttatc tatctaccca     840
acaagcttta tgtggatcct atttgttcgg agatgcgttt atccgtgcta gctacgggtt     900
tgggaatcag catatgaaaa cctcatatac atttgcagag gagagcgatg ttcgttggga     960
taataactgt ctggctggag agattggagc gggattaccg attgtgatta ctccatctaa    1020
gctctatttg aatgagttgc gtcctttcgt gcaagctgag ttttcttatg ccgatcatga    1080
atcttttaca gaggaaggcg atcaagctcg ggcattcaag agcggacatc tcctaaatct    1140
atcagttcct gttggagtga agttgatcg atgttctagt acacatccta ataaatatag     1200
ctttatggcg gcttatatct gtgatgctta tcgcaccatc tctggtactg agacaacgct    1260
cctatcccat caagagacat ggacaacaga tgccttcat ttagcaagac atggagttgt     1320
ggttagagga tctatgtatg cttctctaac aagtaatata gaagtatatg ccatggaag     1380 atatgagtat cgagatgctt ctcgaggcta tggtttgagt gcaggaagta gagtccggtt    1440
ctaa                                                                 1444

<210> SEQ ID NO 12
<211> LENGTH: 56
<212> TYPE: DNA
<213> ORGANISM: Chlamydia sp.
```

<400> SEQUENCE: 12
aagggcccaa ttacgcagag ggtaccgaaa ttatggttcc tcaaggaatt tacgat        56

<210> SEQ ID NO 13
<211> LENGTH: 56
<212> TYPE: DNA
<213> ORGANISM: Chlamydia sp.

<400> SEQUENCE: 13
aagggcccaa ttacgcagag ggtaccctaa gaagaaggca tgccgtgcta gcggag        56

<210> SEQ ID NO 14
<211> LENGTH: 57
<212> TYPE: DNA
<213> ORGANISM: Chlamydia sp.

<400> SEQUENCE: 14
aagggcccaa ttacgcagag ggtaccggag agctcgcgaa tccatacgaa taggaac       57

<210> SEQ ID NO 15
<211> LENGTH: 1013
<212> TYPE: PRT
<213> ORGANISM: Chlamydia sp.

<400> SEQUENCE: 15

```
Met Gln Thr Ser Phe His Lys Phe Phe Leu Ser Met Ile Leu Ala Tyr
1               5                   10                  15

Ser Cys Cys Ser Leu Asn Gly Gly Gly Tyr Ala Ala Glu Ile Met Val
            20                  25                  30

Pro Gln Gly Ile Tyr Asp Gly Glu Thr Leu Thr Val Ser Phe Pro Tyr
        35                  40                  45

Thr Val Ile Gly Asp Pro Ser Gly Thr Thr Val Phe Ser Ala Gly Glu
    50                  55                  60

Leu Thr Leu Lys Asn Leu Asp Asn Ser Ile Ala Ala Leu Pro Leu Ser
65                  70                  75                  80

Cys Phe Gly Asn Leu Leu Gly Ser Phe Thr Val Leu Gly Arg Gly His
                85                  90                  95

Ser Leu Thr Phe Glu Asn Ile Arg Thr Ser Thr Asn Gly Ala Ala Leu
            100                 105                 110

Ser Asp Ser Ala Asn Ser Gly Leu Phe Thr Ile Glu Gly Phe Lys Glu
        115                 120                 125

Leu Ser Phe Ser Asn Cys Asn Pro Leu Leu Ala Val Leu Pro Ala Ala
    130                 135                 140

Thr Thr Asn Asn Gly Ser Gln Thr Pro Ser Thr Thr Ser Thr Pro Ser
145                 150                 155                 160

Asn Gly Thr Ile Tyr Ser Lys Thr Asp Leu Leu Leu Asn Asn Glu
                165                 170                 175

Lys Phe Ser Phe Tyr Ser Asn Ser Val Ser Gly Asp Gly Ala Ile
            180                 185                 190

Asp Ala Lys Ser Leu Thr Val Gln Gly Ile Ser Lys Leu Cys Val Phe
        195                 200                 205

Gln Glu Asn Thr Ala Gln Ala Asp Gly Gly Ala Cys Gln Val Val Thr
    210                 215                 220

Ser Phe Ser Ala Met Ala Asn Glu Ala Pro Ile Ala Phe Val Ala Asn
225                 230                 235                 240

Val Ala Gly Val Arg Gly Gly Gly Ile Ala Ala Val Gln Asp Gly Gln
```

```
                    245                 250                 255
Gln Gly Val Ser Ser Thr Ser Thr Glu Asp Pro Val Val Ser Phe
                260                 265                 270

Ser Arg Asn Thr Ala Val Glu Phe Asp Gly Asn Val Ala Arg Val Gly
            275                 280                 285

Gly Gly Ile Tyr Ser Tyr Gly Asn Val Ala Phe Leu Asn Asn Gly Lys
        290                 295                 300

Thr Leu Phe Leu Asn Asn Val Ala Ser Pro Val Tyr Ile Ala Ala Glu
305                 310                 315                 320

Gln Pro Thr Asn Gly Gln Ala Ser Asn Thr Ser Asp Asn Tyr Gly Asp
                325                 330                 335

Gly Gly Ala Ile Phe Cys Lys Asn Gly Ala Gln Ala Ala Gly Ser Asn
            340                 345                 350

Asn Ser Gly Ser Val Ser Phe Asp Gly Glu Gly Val Val Phe Phe Ser
        355                 360                 365

Ser Asn Val Ala Ala Gly Lys Gly Gly Ala Ile Tyr Ala Lys Lys Leu
    370                 375                 380

Ser Val Ala Asn Cys Gly Pro Val Gln Leu Leu Gly Asn Ile Ala Asn
385                 390                 395                 400

Asp Gly Gly Ala Ile Tyr Leu Gly Glu Ser Gly Glu Leu Ser Leu Ser
                405                 410                 415

Ala Asp Tyr Gly Asp Met Ile Phe Asp Gly Asn Leu Lys Arg Thr Ala
            420                 425                 430

Lys Glu Asn Ala Ala Asp Val Asn Gly Val Thr Val Ser Ser Gln Ala
        435                 440                 445

Ile Ser Met Gly Ser Gly Gly Lys Ile Thr Thr Leu Arg Ala Lys Ala
    450                 455                 460

Gly His Gln Ile Leu Phe Asn Asp Pro Ile Glu Met Ala Asn Gly Asn
465                 470                 475                 480

Asn Gln Pro Ala Gln Ser Ser Glu Pro Leu Lys Ile Asn Asp Gly Glu
                485                 490                 495

Gly Tyr Thr Gly Asp Ile Val Phe Ala Asn Gly Asn Ser Thr Leu Tyr
            500                 505                 510

Gln Asn Val Thr Ile Glu Gln Gly Arg Ile Val Leu Arg Glu Lys Ala
        515                 520                 525

Lys Leu Ser Val Asn Ser Leu Ser Gln Thr Gly Gly Ser Leu Tyr Met
    530                 535                 540

Glu Ala Gly Ser Thr Leu Asp Phe Val Thr Pro Gln Pro Gln Gln
545                 550                 555                 560

Pro Pro Ala Ala Asn Gln Ser Ile Thr Leu Ser Asn Leu His Leu Ser
                565                 570                 575

Leu Ser Ser Leu Leu Ala Asn Asn Ala Val Thr Asn Pro Pro Thr Asn
            580                 585                 590

Pro Pro Ala Gln Asp Ser His Pro Ala Val Ile Gly Ser Thr Thr Ala
        595                 600                 605

Gly Ser Val Thr Ile Ser Gly Pro Ile Phe Phe Glu Asp Leu Asp
    610                 615                 620

Thr Ala Tyr Asp Arg Tyr Asp Trp Leu Gly Ser Asn Gln Lys Ile Asp
625                 630                 635                 640

Val Leu Lys Leu Gln Leu Gly Thr Gln Pro Ala Asn Ala Pro Ser
                645                 650                 655

Asp Leu Thr Leu Gly Asn Glu Met Pro Lys Tyr Gly Tyr Gln Gly Ser
            660                 665                 670
```

Trp Lys Leu Ala Trp Asp Pro Asn Thr Ala Asn Asn Gly Pro Tyr Thr
            675                 680                 685

Leu Lys Ala Thr Trp Thr Lys Thr Gly Tyr Asn Pro Gly Pro Glu Arg
        690                 695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
                725                 730                 735

Cys Arg Gly Leu Trp Val Ser Gly Val Ser Asn Phe Phe Tyr His Asp
            740                 745                 750

Arg Asp Ala Leu Gly Gln Gly Tyr Arg Tyr Ile Ser Gly Gly Tyr Ser
        755                 760                 765

Leu Gly Ala Asn Ser Tyr Phe Gly Ser Ser Met Phe Gly Leu Ala Phe
    770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
                805                 810                 815

Cys Gly Ser Tyr Val Phe Gly Asp Ala Phe Ile Arg Ala Ser Tyr Gly
            820                 825                 830

Phe Gly Asn Gln His Met Lys Thr Ser Tyr Thr Phe Ala Glu Glu Ser
        835                 840                 845

Asp Val Cys Trp Asp Asn Asn Cys Leu Val Gly Glu Ile Gly Val Gly
    850                 855                 860

Leu Pro Ile Val Ile Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
                885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
        915                 920                 925

Pro Asn Lys Tyr Ser Phe Met Gly Ala Tyr Ile Cys Asp Ala Tyr Arg
    930                 935                 940

Thr Ile Ser Gly Thr Gln Thr Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
        995                 1000                1005

Ser Lys  Val Arg Phe
    1010

<210> SEQ ID NO 16
<211> LENGTH: 1013
<212> TYPE: PRT
<213> ORGANISM: Chlamydia sp.

<400> SEQUENCE: 16

Met Gln Thr Ser Phe His Lys Phe Phe Leu Ser Met Ile Leu Ala Tyr
1               5                   10                  15

Ser Cys Cys Ser Leu Thr Gly Gly Gly Tyr Ala Ala Glu Ile Met Val

-continued

```
                     20                  25                  30
Pro Gln Gly Ile Tyr Asp Gly Glu Thr Leu Thr Val Ser Phe Pro Tyr
             35                  40                  45
Thr Val Ile Gly Asp Pro Ser Gly Thr Val Phe Ser Ala Gly Glu
 50                  55                  60
Leu Thr Leu Lys Asn Leu Asp Asn Ser Ile Ala Ala Leu Pro Leu Ser
 65                  70                  75                  80
Cys Phe Gly Asn Leu Leu Gly Ser Phe Thr Val Leu Gly Arg Gly His
                 85                  90                  95
Ser Leu Thr Phe Glu Asn Ile Arg Thr Ser Thr Asn Gly Ala Ala Leu
                100                 105                 110
Ser Asp Ser Ala Asn Ser Gly Leu Phe Thr Ile Glu Gly Phe Lys Glu
                115                 120                 125
Leu Ser Phe Ser Asn Cys Asn Ser Leu Leu Ala Val Leu Pro Ala Ala
                130                 135                 140
Thr Thr Asn Asn Gly Ser Gln Thr Pro Thr Thr Thr Ser Thr Pro Ser
145                 150                 155                 160
Asn Gly Thr Ile Tyr Ser Lys Thr Asp Leu Leu Leu Asn Asn Glu
                    165                 170                 175
Lys Phe Ser Phe Tyr Ser Asn Leu Val Ser Gly Asp Gly Thr Ile
                180                 185                 190
Asp Ala Lys Ser Leu Thr Val Gln Gly Ile Ser Lys Leu Cys Val Phe
                195                 200                 205
Gln Glu Asn Thr Ala Gln Ala Asp Gly Gly Ala Cys Gln Val Val Thr
210                 215                 220
Ser Phe Ser Ala Met Ala Asn Glu Ala Pro Ile Ala Phe Ile Ala Asn
225                 230                 235                 240
Val Ala Gly Val Arg Gly Gly Ile Ala Ala Val Gln Asp Gly Gln
                    245                 250                 255
Gln Gly Val Ser Ser Thr Ser Thr Glu Asp Pro Val Val Ser Phe
                260                 265                 270
Ser Arg Asn Thr Ala Val Glu Phe Asp Gly Asn Val Ala Arg Val Gly
                275                 280                 285
Gly Gly Ile Tyr Ser Tyr Gly Asn Val Ala Phe Leu Asn Asn Gly Lys
290                 295                 300
Thr Leu Phe Leu Asn Asn Val Ala Ser Pro Val Tyr Ile Ala Ala Glu
305                 310                 315                 320
Gln Pro Thr Asn Gly Gln Ala Ser Asn Thr Ser Asp Asn Tyr Gly Asp
                325                 330                 335
Gly Gly Ala Ile Phe Cys Lys Asn Gly Ala Gln Ala Ala Gly Ser Asn
                340                 345                 350
Asn Ser Gly Ser Val Ser Phe Asp Gly Glu Gly Val Val Phe Phe Ser
                355                 360                 365
Ser Asn Val Ala Ala Gly Lys Gly Gly Ala Ile Tyr Ala Lys Lys Leu
    370                 375                 380
Ser Val Ala Asn Cys Gly Pro Val Gln Phe Leu Gly Asn Ile Ala Asn
385                 390                 395                 400
Asp Gly Gly Ala Ile Tyr Leu Gly Glu Ser Gly Glu Leu Ser Leu Ser
                    405                 410                 415
Ala Asp Tyr Gly Asp Ile Ile Phe Asp Gly Asn Leu Lys Arg Thr Ala
                420                 425                 430
Lys Glu Asn Ala Ala Asp Val Asn Gly Val Thr Val Ser Ser Gln Ala
                435                 440                 445
```

```
Ile Ser Met Gly Ser Gly Gly Lys Ile Thr Thr Leu Arg Ala Lys Ala
450                 455                 460

Gly His Gln Ile Leu Phe Asn Asp Pro Ile Glu Met Ala Asn Gly Asn
465                 470                 475                 480

Asn Gln Pro Ala Gln Ser Ser Glu Pro Leu Lys Ile Asn Asp Gly Glu
                485                 490                 495

Gly Tyr Thr Gly Asp Ile Val Phe Ala Asn Gly Asn Ser Thr Leu Tyr
                500                 505                 510

Gln Asn Val Thr Ile Glu Gln Gly Arg Ile Val Leu Arg Glu Lys Ala
                515                 520                 525

Lys Leu Ser Val Asn Ser Leu Ser Gln Thr Gly Gly Ser Leu Tyr Met
530                 535                 540

Glu Ala Gly Ser Thr Leu Asp Phe Val Thr Pro Gln Pro Gln Gln
545                 550                 555                 560

Pro Pro Ala Ala Asn Gln Leu Ile Thr Leu Ser Asn Leu His Leu Ser
                565                 570                 575

Leu Ser Ser Leu Leu Ala Asn Asn Ala Val Thr Asn Pro Pro Thr Asn
                580                 585                 590

Pro Pro Ala Gln Asp Ser His Pro Ala Val Ile Gly Ser Thr Thr Ala
                595                 600                 605

Gly Pro Val Thr Ile Ser Gly Pro Phe Phe Glu Asp Leu Asp Asp
610                 615                 620

Thr Ala Tyr Asp Arg Tyr Asp Trp Leu Gly Ser Asn Gln Lys Ile Asp
625                 630                 635                 640

Val Leu Lys Leu Gln Leu Gly Thr Gln Pro Ser Ala Asn Ala Pro Ser
                645                 650                 655

Asp Leu Thr Leu Gly Asn Glu Met Pro Lys Tyr Gly Tyr Gln Gly Ser
                660                 665                 670

Trp Lys Leu Ala Trp Asp Pro Asn Thr Ala Asn Asn Gly Pro Tyr Thr
                675                 680                 685

Leu Lys Ala Thr Trp Thr Lys Thr Gly Tyr Asn Pro Gly Pro Glu Arg
                690                 695                 700

Val Ala Ser Leu Val Pro Asn Ser Leu Trp Gly Ser Ile Leu Asp Ile
705                 710                 715                 720

Arg Ser Ala His Ser Ala Ile Gln Ala Ser Val Asp Gly Arg Ser Tyr
                725                 730                 735

Cys Arg Gly Leu Trp Val Ser Gly Val Ser Asn Phe Ser Tyr His Asp
                740                 745                 750

Arg Asp Ala Leu Gly Gln Gly Tyr Arg Tyr Ile Ser Gly Gly Tyr Ser
                755                 760                 765

Leu Gly Ala Asn Ser Tyr Phe Gly Ser Ser Met Phe Gly Leu Ala Phe
770                 775                 780

Thr Glu Val Phe Gly Arg Ser Lys Asp Tyr Val Val Cys Arg Ser Asn
785                 790                 795                 800

His His Ala Cys Ile Gly Ser Val Tyr Leu Ser Thr Lys Gln Ala Leu
                805                 810                 815

Cys Gly Ser Tyr Leu Phe Gly Asp Ala Phe Ile Arg Ala Ser Tyr Gly
                820                 825                 830

Phe Gly Asn Gln His Met Lys Thr Ser Tyr Thr Phe Ala Glu Glu Ser
                835                 840                 845

Asp Val Arg Trp Asp Asn Asn Cys Leu Val Gly Glu Ile Gly Val Gly
850                 855                 860
```

```
Leu Pro Ile Val Thr Thr Pro Ser Lys Leu Tyr Leu Asn Glu Leu Arg
865                 870                 875                 880

Pro Phe Val Gln Ala Glu Phe Ser Tyr Ala Asp His Glu Ser Phe Thr
            885                 890                 895

Glu Glu Gly Asp Gln Ala Arg Ala Phe Arg Ser Gly His Leu Met Asn
            900                 905                 910

Leu Ser Val Pro Val Gly Val Lys Phe Asp Arg Cys Ser Ser Thr His
            915                 920                 925

Pro Asn Lys Tyr Ser Phe Met Gly Ala Tyr Ile Cys Asp Ala Tyr Arg
930                 935                 940

Thr Ile Ser Gly Thr Gln Thr Leu Leu Ser His Gln Glu Thr Trp
945                 950                 955                 960

Thr Thr Asp Ala Phe His Leu Ala Arg His Gly Val Ile Val Arg Gly
                965                 970                 975

Ser Met Tyr Ala Ser Leu Thr Ser Asn Ile Glu Val Tyr Gly His Gly
            980                 985                 990

Arg Tyr Glu Tyr Arg Asp Thr Ser  Arg Gly Tyr Gly Leu  Ser Ala Gly
            995                 1000                1005

Ser Lys  Val Arg Phe
    1010

<210> SEQ ID NO 17
<211> LENGTH: 505
<212> TYPE: PRT
<213> ORGANISM: Chlamydia sp.

<400> SEQUENCE: 17

Glu Ile Met Val Pro Gln Gly Ile Tyr Asp Gly Glu Thr Leu Thr Val
1               5                   10                  15

Ser Phe Pro Tyr Thr Val Ile Gly Asp Pro Ser Gly Thr Thr Val Phe
                20                  25                  30

Ser Ala Gly Glu Leu Thr Leu Lys Asn Leu Asp Asn Ser Ile Ala Ala
            35                  40                  45

Leu Pro Leu Ser Cys Phe Gly Asn Leu Leu Gly Ser Phe Thr Val Leu
50                  55                  60

Gly Arg Gly His Ser Leu Thr Phe Glu Asn Ile Arg Thr Ser Thr Asn
65                  70                  75                  80

Gly Ala Ala Leu Ser Asn Ser Ala Ala Asp Gly Leu Phe Thr Ile Glu
                85                  90                  95

Gly Phe Lys Glu Leu Ser Phe Ser Asn Cys Asn Ser Leu Leu Ala Val
                100                 105                 110

Leu Pro Ala Ala Thr Thr Asn Lys Gly Ser Gln Thr Pro Thr Thr Thr
            115                 120                 125

Ser Thr Pro Ser Asn Gly Thr Ile Tyr Ser Lys Thr Asp Leu Leu Leu
130                 135                 140

Leu Asn Asn Glu Lys Phe Ser Phe Tyr Ser Asn Leu Val Ser Gly Asp
145                 150                 155                 160

Gly Gly Ala Ile Asp Ala Lys Ser Leu Thr Val Gln Gly Ile Ser Lys
                165                 170                 175

Leu Cys Val Phe Gln Glu Asn Thr Ala Gln Ala Asp Gly Gly Ala Cys
            180                 185                 190

Gln Val Val Thr Ser Phe Ser Ala Met Ala Asn Glu Ala Pro Ile Ala
            195                 200                 205

Phe Val Ala Asn Val Ala Gly Val Arg Gly Gly Gly Ile Ala Ala Val
210                 215                 220
```

Gln Asp Gly Gln Gln Gly Val Ser Ser Thr Ser Thr Glu Asp Pro
225                 230                 235                 240

Val Val Ser Phe Ser Arg Asn Thr Ala Val Glu Phe Asp Gly Asn Val
        245                 250                 255

Ala Arg Val Gly Gly Ile Tyr Ser Tyr Gly Asn Val Ala Phe Leu
        260                 265                 270

Asn Asn Gly Lys Thr Leu Phe Leu Asn Asn Val Ala Ser Pro Val Tyr
            275                 280                 285

Ile Ala Ala Lys Gln Pro Thr Ser Gly Gln Ala Ser Asn Thr Ser Asn
290                 295                 300

Asn Tyr Gly Asp Gly Gly Ala Ile Phe Cys Lys Asn Gly Ala Gln Ala
305                 310                 315                 320

Gly Ser Asn Asn Ser Gly Ser Val Ser Phe Asp Gly Glu Gly Val Val
            325                 330                 335

Phe Phe Ser Ser Asn Val Ala Ala Gly Lys Gly Gly Ala Ile Tyr Ala
        340                 345                 350

Lys Lys Leu Ser Val Ala Asn Cys Gly Pro Val Gln Phe Leu Arg Asn
        355                 360                 365

Ile Ala Asn Asp Gly Gly Ala Ile Tyr Leu Gly Glu Ser Gly Glu Leu
370                 375                 380

Ser Leu Ser Ala Asp Tyr Gly Asp Ile Ile Phe Asp Gly Asn Leu Lys
385                 390                 395                 400

Arg Thr Ala Lys Glu Asn Ala Ala Asp Val Asn Gly Val Thr Val Ser
        405                 410                 415

Ser Gln Ala Ile Ser Met Gly Ser Gly Gly Lys Ile Thr Thr Leu Arg
        420                 425                 430

Ala Lys Ala Gly His Gln Ile Leu Phe Asn Asp Pro Ile Glu Met Ala
        435                 440                 445

Asn Gly Asn Asn Gln Pro Ala Gln Ser Ser Lys Leu Leu Lys Ile Asn
450                 455                 460

Asp Gly Glu Gly Tyr Thr Gly Asp Ile Val Phe Ala Asn Gly Ser Ser
465                 470                 475                 480

Thr Leu Tyr Gln Asn Val Thr Ile Glu Gln Gly Arg Ile Val Leu Arg
            485                 490                 495

Glu Lys Ala Lys Leu Ser Val Asn Ser
            500                 505

<210> SEQ ID NO 18
<211> LENGTH: 57
<212> TYPE: DNA
<213> ORGANISM: Chlamydia sp.

<400> SEQUENCE: 18
aagggcccaa ttacgcagag ctcgagagaa attatggttc ctcaaggaat ttacgat        57

<210> SEQ ID NO 19
<211> LENGTH: 20
<212> TYPE: DNA
<213> ORGANISM: Chlamydia sp.

<400> SEQUENCE: 19
cgctctagaa ctagtggatc        20

<210> SEQ ID NO 20
<211> LENGTH: 22
<212> TYPE: DNA

<213> ORGANISM: Chlamydia sp.

<400> SEQUENCE: 20
atggttcctc aaggaattta cg　　　　　　　　　　　　　　　　　　　　　　22

<210> SEQ ID NO 21
<211> LENGTH: 19
<212> TYPE: DNA
<213> ORGANISM: Chlamydia sp.

<400> SEQUENCE: 21
ggtcccccat cagcgggag　　　　　　　　　　　　　　　　　　　　　　　19

<210> SEQ ID NO 22
<211> LENGTH: 1515
<212> TYPE: DNA
<213> ORGANISM: Chlamydia sp.

<400> SEQUENCE: 22

```
gaaatcatgg ttcctcaagg aatttacgat ggggagacgt taactgtatc atttccctat       60
actgttatag agatccgag tgggactact gttttttctg caggagagtt aacattaaaa       120
aatcttgaca attctattgc agctttgcct ttaagttgtt ttgggaactt attagggagt      180
tttactgttt tagggagagg acactcgttg acttcgaga acatacggac ttctacaaat      240
ggggcagctc taagtaatag cgctgctgat ggactgttta ctattgaggg ttttaaagaa      300
ttatcctttt ccaattgcaa ttcattactt gccgtactgc ctgctgcaac gactaataag      360
ggtagccaga ctccgacgac aacatctaca ccgtctaatg gtactattta ttctaaaaca      420
gatcttttgt tactcaataa tgagaagttc tcattctata gtaatttagt ctctggagat      480
gggggagcta tagatgctaa gagcttaacg gttcaaggaa ttagcaagct ttgtgtcttc      540
caagaaaata ctgctcaagc tgatggggga gcttgtcaag tagtcaccag tttctctgct      600
atggctaacg aggctcctat tgcctttgta gcgaatgttg caggagtaag aggggagggg      660
attgctgctg ttcaggatgg gcagcaggga gtgtcatcat ctacttcaac agaagatcca      720
gtagtaagtt tttccagaaa tactgcggta gagtttgatg ggaacgtagc ccgagtagga      780
ggagggattt actcctacgg gaacgttgct ttcctgaata atggaaaaac cttgtttctc      840
aacaatgttg cttctcctgt ttacattgct gctaagcaac aacaagtgg acaggcttct      900
aatacgagta ataattacgg agatggagga gctatcttct gtaagaatgg tgcgcaagca      960
ggatccaata actctggatc agtttccttt gatggagagg gagtagtttt ctttagtagc     1020
aatgtagctg ctgggaaagg gggagctatt tatgccaaaa agctctcggt tgctaactgt     1080
ggccctgtac aattttttaag gaatatcgct aatgatggtg gagcgattta tttaggagaa     1140
tctggagagc tcagtttatc tgctgattat ggagatatta ttttcgatgg gaatcttaaa     1200
agaacagcca aagagaatgc tgccgatgtt aatgcgtaa ctgtgtcctc acaagccatt     1260
tcgatgggat cgggagggaa aataacgaca ttaagagcta aagcagggca tcagattctc     1320
tttaatgatc ccatcgagat ggcaaacgga aataaccagc cagcgcagtc ttccaaactt     1380
ctaaaaatta acgatggtga aggatacaca ggggatattg tttttgctaa tggaagcagt     1440
actttgtacc aaaatgttac gatagagcaa ggaaggattg tcttcgtgaa aaaggcaaaa     1500
ttatcagtga attct                                                      1515
```

<210> SEQ ID NO 23
<211> LENGTH: 3354

```
<212> TYPE: DNA
<213> ORGANISM: Artificial Sequence
<220> FEATURE:
<223> OTHER INFORMATION: Description of Artificial Sequence: Recombinant
                        Expression Vector

<400> SEQUENCE: 23
atgcaaacgt ctttccataa gttctttctt tcaatgattc tagcttattc ttgctgctct      60
ttaaatgggg gggggtatgc agaaatcatg gttcctcaag gaatttacga tggggagacg     120
ttaactgtat catttcccta tactgttata ggagatccga gtgggactac tgttttttct     180
gcaggagagt taacgttaaa aaatcttgac aattctattg cagctttgcc tttaagttgt     240
tttgggaact tattagggag ttttactgtt tagggagag acactcgtt gactttcgag       300
aacatacgga cttctacaaa tggagctgca ctaagtgaca cgctaatag cgggttattt      360
actattgagg gttttaaaga attatctttt tccaattgca acccattact tgccgtactg     420
cctgctgcaa cgactaataa tggtagccag actccgtcga caacatctac accgtctaat     480
ggtactattt attctaaaac agatcttttg ttactcaata tgagaagtt ctcattctat      540
agtaattcag tctctggaga tgggggagct atagatgcta agagcttaac ggttcaagga     600
attagcaagc tttgtgtctt ccaagaaaat actgctcaag ctgatggggg agcttgtcaa     660
gtagtcacca gttctctgc tatggctaac gaggctccta ttgcctttgt agcgaatgtt      720
gcaggagtaa gaggggagg gattgctgct gttcaggatg gcagcaggg agtgtcatca       780
tctacttcaa cagaagatcc agtagtaagt ttttccagaa atactgcggt agagtttgat     840
gggaacgtag cccgagtagg aggagggatt tactcctacg ggaacgttgc tttcctgaat     900
aatggaaaaa ccttgtttct caacaatgtt gcttctcctg tttacattgc tgctgagcaa     960
ccaacaaatg gacaggcttc taatacgagt gataattacg gagatggagg agctatcttc    1020
tgtaagaatg gtgcgcaagc agcaggatcc aataactctg gatcagtttc ctttgatgga    1080
gagggagtag ttttctttag tagcaatgta gctgctggga aggggagc tatttatgcc      1140
aaaaagctct cggttgctaa ctgtggcct gtacaactct tagggaatat cgctaatgat     1200
ggtggagcga tttatttagg agaatctgga gagctcagtt tatctgctga ttatggagat    1260
atgattttcg atgggaatct taaaagaaca gccaaagaga tgctgccga tgttaatggc     1320
gtaactgtgt cctcacaagc catttcgatg ggatcgggag ggaaaataac gacattaaga    1380
gctaaagcag ggcatcagat tctctttaat gatcccatcg agatggcaaa cggaaataac    1440
cagccagcgc agtcttccga acctctaaaa attaacgatg gtgaaggata cacagggat    1500
attgttttg ctaatggaaa cagtactttg taccaaaatg ttacgataga gcaaggaagg    1560
attgttcttc gtgaaaaggc aaaattatca gtgaattctc taagtcagac aggtgggagt    1620
ctgtatatgg aagctgggag tacattggat tttgtaactc cacaaccacc acaacagcct    1680
cctgccgcta atcagtcgat cacgctttcc aatctgcatt tgtctctttc ttcttttgtta   1740
gcaaacaatg cagttacgaa tcctcctacc aatcctccag cgcaagattc tcatcctgca    1800
gtcattggta gcacaactgc tggttctgtt acaattagtg ggcctatctt ttttgaggat    1860
ttggatgata cagcttatga taggtatgat tggctaggtt ctaatcaaaa aatcgatgtc    1920
ctgaaattac agttagggac tcagccccca gctaatgccc catcagattt gactctaggg    1980
aatgagatgc taagtatgg ctatcaagga agctggaagc ttgcgtggga tcctaataca     2040
gcaaataatg gtccttatac tctgaaagct acatggacta aaactgggta taatcctggg    2100
cctgagcgag tagcttcttt ggttccaaat agtttatggg gatccatttt agatatacga    2160
```

```
tctgcgcatt cagcaattca agcaagtgtg gatgggcgct cttattgtcg aggattatgg   2220
gtttctggag tttcgaattt cttctatcat gaccgcgatg ctttaggtca gggatatcgg   2280
tatattagtg ggggttattc cttaggagca aactcctact ttggatcatc gatgtttggt   2340
ctagcattta ctgaagtatt tggtagatct aaagattatg tagtgtgtcg ttccaatcat   2400
catgcttgca taggatccgt ttatctatct accaaacagg ctttatgtgg atcttatgtg   2460
tttggagatg cgtttattcg tgctagctac gggtttggga atcagcatat gaaaacctca   2520
tatacatttg cagaggagag cgatgtttgt tgggataata actgtctggt tggagagatt   2580
ggagtgggat taccgattgt gattactcca tctaagctct atttgaatga gttgcgtcct   2640
ttcgtgcaag ctgagttttc ttatgccgat catgaatctt ttacagagga aggcgatcaa   2700
gctcgggcat tcaggagtgg acatctcatg aatctatcag ttcctgttgg agtaaaattt   2760
gatcgatgtt ctagtacaca ccctaataaa tatagcttta tggggcttta tatctgtgat   2820
gcttatcgca ccatctctgg gactcagaca acactcctat cccatcaaga gacatggaca   2880
acagatgcct tcatttggc aagacatgga gtcatagtta gagggtctat gtatgcttct   2940
ctaacaagca atatagaagt atatggccat ggaagatatg agtatcgaga tacttctcga   3000
ggttatggtt tgagtgcagg aagtaaagtc cggttctaaa aatattggtt agatagttaa   3060
gtgttagcga tgcctttttc tttgagatct acatcatttt gttttttagc ttgtttgtgt   3120
tcctattcgt atggattcgc gagctctcct caagtgttaa cacctaatgt aaccactcct   3180 tttaagggg acgatgttta cttgaatgga gactgcgctt ttgtcaatgt ctatgcaggg   3240
gcagagaacg gctcaattat ctcagctaat ggcgacaatt taacgattac cggacaaaac   3300
catacattat catttacaca ttctcaaggg ccagttcttc aaaattagcc ttca          3354

<210> SEQ ID NO 24
<211> LENGTH: 3324
<212> TYPE: DNA
<213> ORGANISM: Artificial Sequence
<220> FEATURE:
<223> OTHER INFORMATION: Description of Artificial Sequence: Recombinant
      Expression Vector

<400> SEQUENCE: 24
atgcaaacgt ctttccataa gttctttctt tcaatgattc tagcttattc ttgctgctct     60
ttaagtgggg gggggtatgc agcagaaatc atgattcctc aaggaattta cgatggggag    120
acgttaactg tatcatttcc ctatactgtt ataggagatc cgagtgggac tactgttttt    180
tctgcaggag agttaacgtt aaaaaatctt gacaattcta ttgcagcttt gcctttaagt    240
tgttttggga acttattagg gagttttact gttttaggga gaggacactc gttgactttc    300
gagaacatac ggacttctac aaatggagct gcactaagtg acagcgctaa tagcgggtta    360
tttactattg agggttttaa agaattatct ttttccaatt gcaactcatt acttgccgta    420
ctgcctgctg caacgactaa taatggtagc cagactccga cgacaacatc tacaccgtct    480
aatggtacta tttattctaa aacgatcttt tgttactca ataatgagaa gttctcattc    540
tatagtaatt tagtctctgg agatggggga actatagatg ctaagagctt aacggttcaa    600
ggaattagca agctttgtgt cttccaagaa aatactgctc aagctgatgg gggagcttgt    660
caagtagtca ccagtttctc tgctatggct aacgaggctc ctattgcctt tatagcgaat    720
gttgcaggag taagagggg agggattgct gctgttcagg atgggcagca gggagtgtca    780
tcatctactt caacagaaga tccagtagta agttttccca gaaatactgc ggtagagttt    840
```

```
gatgggaacg tagcccgagt aggaggaggg atttactcct acgggaacgt tgctttcctg    900
aataatggaa aaaccttgtt tctcaacaat gttgcttctc ctgtttacat tgctgctgag    960
caaccaacaa atgacaggc ttctaatacg agtgataatt acgagatgg aggagctatc    1020
ttctgtaaga atggtgcgca agcagcagga tccaataact ctggatcagt ttcctttgat    1080
ggagagggag tagttttctt tagtagcaat gtagctgctg ggaaaggggg agctatttat    1140
gccaaaaagc tctcggttgc taactgtggc cctgtacaat tcttagggaa tatcgctaat    1200
gatggtggag cgatttattt aggagaatct ggagagctca gtttatctgc tgattatgga    1260
gatattattt tcgatgggaa tcttaaaaga acagccaaag agaatgctgc cgatgttaat    1320
ggcgtaactg tgtcctcaca agccatttcg atgggatcgg gagggaaaat aacgacatta    1380
agagctaaag cagggcatca gattctcttt aatgatccca tcgagatggc aaacggaaat    1440
aaccagccag cgcagtcttc cgaacctcta aaaattaacg atggtgaagg atacacaggg    1500
gatattgttt ttgctaatgg aaacagtact ttgtaccaaa atgttacgat agagcaagga    1560
aggattgttc ttcgtgaaaa ggcaaaatta tcagtgaatt ctctaagtca gacaggtggg    1620
agtctgtata tggaagctgg gagtacattg gattttgtaa ctccacaacc accacaacag    1680
cctcctgccg ctaatcagtt gatcacgctt tccaatctgc atttgtctct ttcttctttg    1740
ttagcaaaca atgcagttac gaatcctcct accaatcctc cagcgcaaga ttctcatcct    1800
gcagtcattg gtagcacaac tgctggtcct gtcacaatta gtgggccttt cttttttgag    1860
gatttggatg atacagctta tgataggtat gattggctag gttctaatca aaaaatcgat    1920
gtcctgaaat tacagttagg gactcagccc tcagctaatg ccccatcaga tttgactcta    1980
gggaatgaga tgcctaagta tggctatcaa ggaagctgga agcttgcgtg ggatcctaat    2040
acagcaaata atggtcctta tactctgaaa gctacatgga ctaaaactgg gtataatcct    2100
gggcctgagc gagtagcttc tttggttcca aatagtttat ggggatccat tttagatata    2160
cgatctgcgc attcagcaat tcaagcaagt gtggatgggc gctcttattg tcgaggatta    2220
tgggtttctg gagtttcgaa tttctcctat catgaccgcg atgctttagg tcagggtat    2280
cggtatatta gtgggggtta ttccttagga gcaaactcct actttggatc atcgatgttt    2340
ggtctagcat ttaccgaagt atttggtaga tctaaagatt atgtagtgtg tcgttccaat    2400
catcatgctt gcataggatc cgtttatcta tctaccaaac aagctttatg tggatcctat    2460
ttgttcggag atgcgtttat ccgtgctagc tacgggtttg gaaccagca tatgaaaaacc    2520
tcatacacat ttgcagagga gagcgatgtt cgttgggata taactgtct ggttggagag    2580
attggagtgg gattaccgat tgtgactact ccatctaagc tctatttgaa tgagttgcgt    2640
cctttcgtgc aagctgagtt ttcttatgcc gatcatgaat cttttacaga ggaaggcgat    2700
caagctcggg cattcaggag tggtcatctc atgaatctat cagttcctgt tggagtaaaa    2760
tttgatcgat gttctagtac acaccctaat aaatatagct ttatgggggc ttatatctgt    2820
gatgcttatc gcaccatctc tgggactcag acaacactcc tatcccatca agagacatgg    2880
acaacagatg cctttcattt ggcaagacat ggagtcatag ttagagggtc tatgtatgct    2940
tctctaacaa gcaatataga agtatatggc catggaagat atgagtatcg agatacttct    3000
cgaggttatg gtttgagtgc aggaagtaaa gtccggttct aaaaatattg gttagatagt    3060
taagtgttag cgatgccttt ttctttgaga tctacatcat tttgtttttt agcttgtttg    3120
tgttcctatt cgtatggatt cgcgagctct cctcaagtgt taacacctaa tgtaaccact    3180
```

```
cctttttaagg gggacgatgt ttacttgaat ggagactgcg ctttagtcaa tgtctatgca    3240
ggggcagaga acggctcaat tatctcagct aatggcgaca atttaacgat taccggacaa    3300
aaccatgcat tatcatttac agat                                           3324
```

<210> SEQ ID NO 25
<211> LENGTH: 65
<212> TYPE: PRT
<213> ORGANISM: Chlamydia sp.

<400> SEQUENCE: 25

```
Pro Tyr Thr Val Ile Gly Asp Pro Ser Gly Thr Thr Val Phe Ser Ala
1               5                   10                  15

Gly Glu Leu Thr Leu Lys Asn Leu Asp Asn Ser Ile Ala Ala Pro Leu
            20                  25                  30

Ser Cys Phe Gly Asn Leu Leu Gly Ser Phe Thr Val Leu Gly Arg Gly
        35                  40                  45

His Ser Leu Thr Phe Glu Asn Ile Arg Thr Ser Thr Asn Gly Ala Ala
    50                  55                  60

Leu
65
```

<210> SEQ ID NO 26
<211> LENGTH: 24
<212> TYPE: PRT
<213> ORGANISM: Chlamydia sp.

<400> SEQUENCE: 26

```
Ala Ala Asn Gln Leu Ile Thr Leu Ser Asn Leu His Leu Ser Leu Ser
1               5                   10                  15

Ser Leu Leu Ala Asn Asn Ala Val
            20
```

<210> SEQ ID NO 27
<211> LENGTH: 8
<212> TYPE: PRT
<213> ORGANISM: Chlamydia sp.

<400> SEQUENCE: 27

```
Gly Tyr Thr Gly Asp Ile Val Phe
1               5
```

<210> SEQ ID NO 28
<211> LENGTH: 7
<212> TYPE: PRT
<213> ORGANISM: Chlamydia sp.

<400> SEQUENCE: 28

```
Tyr Gly Asp Ile Ile Phe Asp
1               5
```

<210> SEQ ID NO 29
<211> LENGTH: 63
<212> TYPE: PRT
<213> ORGANISM: Chlamydia sp.

<400> SEQUENCE: 29

```
Gly Tyr Ala Ala Glu Ile Met Val Pro Gln Gly Ile Tyr Asp Gly Glu
1               5                   10                  15

Thr Leu Thr Val Ser Phe Pro Tyr Thr Val Ile Gly Asp Pro Ser Gly
            20                  25                  30
```

```
Thr Thr Val Phe Ser Ala Gly Glu Leu Thr Leu Lys Asn Leu Asp Asn
         35                  40                  45

Ser Ile Ala Ala Leu Pro Leu Ser Cys Phe Gly Asn Leu Leu Gly
 50                  55                  60

<210> SEQ ID NO 30
<211> LENGTH: 22
<212> TYPE: PRT
<213> ORGANISM: Chlamydia sp.

<400> SEQUENCE: 30

Met Ala Asn Gly Asn Asn Gln Pro Ala Gln Ser Ser Lys Leu Leu Lys
  1               5                  10                  15

Ile Asn Asp Gly Glu Gly
             20

<210> SEQ ID NO 31
<211> LENGTH: 14
<212> TYPE: PRT
<213> ORGANISM: Chlamydia sp.

<400> SEQUENCE: 31

Ala Asn Gly Ser Ser Thr Leu Tyr Gln Asn Val Thr Ile Glu
  1               5                  10

<210> SEQ ID NO 32
<211> LENGTH: 10
<212> TYPE: PRT
<213> ORGANISM: Chlamydia sp.

<400> SEQUENCE: 32

Lys Leu Ser Val Asn Ser Leu Ser Gln Thr
  1               5                  10

<210> SEQ ID NO 33
<211> LENGTH: 45
<212> TYPE: PRT
<213> ORGANISM: Chlamydia sp.

<400> SEQUENCE: 33

Val Ile Gly Ser Thr Thr Ala Gly Ser Val Thr Ile Ser Gly Pro Ile
  1               5                  10                  15

Phe Phe Glu Asp Leu Asp Asp Thr Ala Tyr Asp Arg Tyr Asp Trp Leu
             20                  25                  30

Gly Ser Asn Gln Lys Ile Asn Val Leu Lys Leu Gln Leu
         35                  40                  45

<210> SEQ ID NO 34
<211> LENGTH: 64
<212> TYPE: PRT
<213> ORGANISM: Chlamydia sp.

<400> SEQUENCE: 34

Val Ile Gly Ser Thr Thr Ala Gly Ser Val Thr Ile Ser Gly Pro Ile
  1               5                  10                  15

Phe Phe Glu Asp Leu Asp Asp Thr Ala Tyr Asp Arg Tyr Asp Trp Leu
             20                  25                  30

Gly Ser Asn Gln Lys Ile Asn Val Leu Lys Leu Gln Leu Gly Thr Lys
         35                  40                  45

Pro Pro Ala Asn Ala Pro Ser Asp Leu Thr Leu Gly Asn Glu Met Pro
 50                  55                  60
```

<210> SEQ ID NO 35
<211> LENGTH: 10
<212> TYPE: PRT
<213> ORGANISM: Chlamydia sp.

<400> SEQUENCE: 35

```
Asp Pro Asn Thr Ala Asn Asn Gly Pro Tyr
1               5                   10
```

<210> SEQ ID NO 36
<211> LENGTH: 458
<212> TYPE: PRT
<213> ORGANISM: Chlamydia sp.

<400> SEQUENCE: 36

```
Gly Gly Ala Cys Gln Val Val Thr Ser Phe Ser Ala Met Ala Asn Glu
1               5                   10                  15

Ala Pro Ile Ala Phe Val Ala Asn Val Ala Gly Val Arg Gly Gly Gly
            20                  25                  30

Ile Ala Ala Val Gln Asp Gly Gln Gln Gly Val Ser Ser Ser Thr Ser
        35                  40                  45

Thr Glu Asp Pro Val Val Ser Phe Ser Arg Asn Thr Ala Val Glu Phe
    50                  55                  60

Asp Gly Asn Val Ala Arg Val Gly Gly Ile Tyr Ser Tyr Gly Asn
65                  70                  75                  80

Val Ala Phe Leu Asn Asn Gly Lys Thr Leu Phe Leu Asn Asn Val Ala
                85                  90                  95

Ser Pro Val Tyr Ile Ala Ala Lys Gln Pro Thr Ser Gly Gln Ala Ser
            100                 105                 110

Asn Thr Ser Asn Asn Tyr Gly Asp Gly Gly Ala Ile Phe Cys Lys Asn
        115                 120                 125

Gly Ala Gln Ala Gly Ser Asn Asn Ser Gly Ser Val Ser Phe Asp Gly
    130                 135                 140

Glu Gly Val Val Phe Ser Ser Asn Val Ala Ala Gly Lys Gly Gly
145                 150                 155                 160

Ala Ile Tyr Ala Lys Lys Leu Ser Val Ala Asn Cys Gly Pro Val Gln
                165                 170                 175

Phe Leu Arg Asn Ile Ala Asn Asp Gly Ala Ile Tyr Leu Gly Glu
            180                 185                 190

Ser Gly Glu Leu Ser Leu Ser Ala Asp Tyr Gly Asp Ile Ile Phe Asp
        195                 200                 205

Gly Asn Leu Lys Arg Thr Ala Lys Glu Asn Ala Ala Asp Val Asn Gly
    210                 215                 220

Val Thr Val Ser Ser Gln Ala Ile Ser Met Gly Ser Gly Gly Lys Ile
225                 230                 235                 240

Thr Thr Leu Arg Ala Lys Ala Gly His Gln Ile Leu Phe Asn Asp Pro
                245                 250                 255

Ile Glu Met Ala Asn Gly Asn Asn Gln Pro Ala Gln Ser Ser Lys Leu
            260                 265                 270

Leu Lys Ile Asn Asp Gly Glu Gly Tyr Thr Gly Asp Ile Val Phe Ala
        275                 280                 285

Asn Gly Ser Ser Thr Leu Tyr Gln Asn Val Thr Ile Glu Gln Gly Arg
    290                 295                 300

Ile Val Leu Arg Glu Lys Ala Lys Leu Ser Val Asn Ser Leu Ser Gln
305                 310                 315                 320
```

```
Thr Gly Gly Ser Leu Tyr Met Glu Ala Gly Ser Thr Trp Asp Phe Val
            325                 330                 335

Thr Pro Gln Pro Gln Gln Pro Pro Ala Ala Asn Gln Leu Ile Thr
            340                 345                 350

Leu Ser Asn Leu His Leu Ser Leu Ser Ser Leu Leu Ala Asn Asn Ala
            355                 360                 365

Val Thr Asn Pro Pro Thr Asn Pro Pro Ala Gln Asp Ser His Pro Ala
370                 375                 380

Val Ile Gly Ser Thr Thr Ala Gly Ser Val Thr Ile Ser Gly Pro Ile
385                 390                 395                 400

Phe Phe Glu Asp Leu Asp Asp Thr Ala Tyr Asp Arg Tyr Asp Trp Leu
                405                 410                 415

Gly Ser Asn Gln Lys Ile Asn Val Leu Lys Leu Gln Leu Gly Thr Lys
            420                 425                 430

Pro Pro Ala Asn Ala Pro Ser Asp Leu Thr Leu Gly Asn Glu Met Pro
            435                 440                 445

Lys Tyr Gly Tyr Gln Gly Ser Trp Lys Leu
            450                 455

<210> SEQ ID NO 37
<211> LENGTH: 325
<212> TYPE: PRT
<213> ORGANISM: Chlamydia sp.

<400> SEQUENCE: 37

Leu Lys Ala Thr Trp Thr Lys Thr Gly Tyr Asn Pro Gly Pro Glu Arg
1               5                   10                  15

Val Ala Ser Leu Val Pro Asn Ser Leu Trp Gly Ser Ile Leu Asp Ile
            20                  25                  30

Arg Ser Ala His Ser Ala Ile Gln Ala Ser Val Asp Gly Arg Ser Tyr
            35                  40                  45

Cys Arg Gly Leu Trp Val Ser Gly Val Ser Asn Phe Phe Tyr His Asp
    50                  55                  60

Arg Asp Ala Leu Gly Gln Gly Tyr Arg Tyr Ile Ser Gly Gly Tyr Ser
65                  70                  75                  80

Leu Gly Ala Asn Ser Tyr Phe Gly Ser Ser Met Phe Gly Leu Ala Phe
                85                  90                  95

Thr Glu Val Phe Gly Arg Ser Lys Asp Tyr Val Val Cys Arg Ser Asn
            100                 105                 110

His His Ala Cys Ile Gly Ser Val Tyr Leu Ser Thr Gln Gln Ala Leu
            115                 120                 125

Cys Gly Ser Tyr Leu Phe Gly Asp Ala Phe Ile Arg Ala Ser Tyr Gly
    130                 135                 140

Phe Gly Asn Gln His Met Lys Thr Ser Tyr Thr Phe Ala Glu Glu Ser
145                 150                 155                 160

Asp Val Arg Trp Asp Asn Asn Cys Leu Ala Gly Glu Ile Gly Ala Gly
                165                 170                 175

Leu Pro Ile Val Ile Thr Pro Ser Lys Leu Tyr Leu Asn Glu Leu Arg
            180                 185                 190

Pro Phe Val Gln Ala Glu Phe Ser Tyr Ala Asp His Glu Ser Phe Thr
            195                 200                 205

Glu Glu Gly Asp Gln Ala Arg Ala Phe Lys Ser Gly His Leu Leu Asn
    210                 215                 220

Leu Ser Val Pro Val Gly Val Lys Phe Asp Arg Cys Ser Ser Thr His
225                 230                 235                 240
```

```
Pro Asn Lys Tyr Ser Phe Met Ala Ala Tyr Ile Cys Asp Ala Tyr Arg
                245                 250                 255

Thr Ile Ser Gly Thr Glu Thr Thr Leu Leu Ser His Gln Glu Thr Trp
            260                 265                 270

Thr Thr Asp Ala Phe His Leu Ala Arg His Gly Val Val Arg Gly
        275                 280                 285

Ser Met Tyr Ala Ser Leu Thr Ser Asn Ile Glu Val Tyr Gly His Gly
    290                 295                 300

Arg Tyr Glu Tyr Arg Asp Ala Ser Arg Gly Tyr Gly Leu Ser Ala Gly
305                 310                 315                 320

Ser Arg Val Arg Phe
                325

<210> SEQ ID NO 38

<400> SEQUENCE: 38

000                                                                    3

<210> SEQ ID NO 39
<211> LENGTH:
<212> TYPE:
<213> ORGANISM:

<400> SEQUENCE: 39

000

<210> SEQ ID NO 40
<211> LENGTH:
<212> TYPE:
<213> ORGANISM:

<400> SEQUENCE: 40

000

<210> SEQ ID NO 41
<211> LENGTH:
<212> TYPE:
<213> ORGANISM:

<400> SEQUENCE: 41

000

<210> SEQ ID NO 42
<211> LENGTH: 6
<212> TYPE: PRT
<213> ORGANISM: Chlamydia sp.

<400> SEQUENCE: 42

Glu Ile Met Val Pro Gln
1               5

<210> SEQ ID NO 43
<211> LENGTH: 984
<212> TYPE: PRT
<213> ORGANISM: Chlamydia sp.

<400> SEQUENCE: 43

Glu Ile Met Val Pro Gln Gly Ile Tyr Asp Gly Glu Thr Leu Thr Val
1               5                   10                  15

Ser Phe Pro Tyr Thr Val Ile Gly Asp Pro Ser Gly Thr Thr Val Phe
```

-continued

```
                    20                  25                  30
Ser Ala Gly Glu Leu Thr Leu Lys Asn Leu Asp Asn Ser Ile Ala Ala
             35                  40                  45
Leu Pro Leu Ser Cys Phe Gly Asn Leu Leu Gly Ser Phe Thr Val Leu
         50                  55                  60
Gly Arg Gly His Ser Leu Thr Phe Glu Asn Ile Arg Thr Ser Thr Asn
 65                  70                  75                  80
Gly Ala Ala Leu Ser Asn Ser Ala Ala Asp Gly Leu Phe Thr Ile Glu
                 85                  90                  95
Gly Phe Lys Glu Leu Ser Phe Ser Asn Cys Asn Ser Leu Leu Ala Val
            100                 105                 110
Leu Pro Ala Ala Thr Thr Asn Lys Gly Ser Gln Thr Pro Thr Thr Thr
            115                 120                 125
Ser Thr Pro Ser Asn Gly Thr Ile Tyr Ser Lys Thr Asp Leu Leu Leu
            130                 135                 140
Leu Asn Asn Glu Lys Phe Ser Phe Tyr Ser Asn Leu Val Ser Gly Asp
145                 150                 155                 160
Gly Gly Ala Ile Asp Ala Lys Ser Leu Thr Val Gln Gly Ile Ser Lys
                165                 170                 175
Leu Cys Val Phe Gln Glu Asn Thr Ala Gln Ala Asp Gly Ala Cys
            180                 185                 190
Gln Val Val Thr Ser Phe Ser Ala Met Ala Asn Glu Ala Pro Ile Ala
            195                 200                 205
Phe Val Ala Asn Val Ala Gly Val Arg Gly Gly Ile Ala Ala Val
            210                 215                 220
Gln Asp Gly Gln Gln Gly Val Ser Ser Thr Ser Thr Glu Asp Pro
225                 230                 235                 240
Val Val Ser Phe Ser Arg Asn Thr Ala Val Glu Phe Asp Gly Asn Val
                245                 250                 255
Ala Arg Val Gly Gly Ile Tyr Ser Tyr Gly Asn Val Ala Phe Leu
                260                 265                 270
Asn Asn Gly Lys Thr Leu Phe Leu Asn Asn Val Ala Ser Pro Val Tyr
            275                 280                 285
Ile Ala Ala Lys Gln Pro Thr Ser Gly Gln Ala Ser Asn Thr Ser Asn
290                 295                 300
Asn Tyr Gly Asp Gly Gly Ala Ile Phe Cys Lys Asn Gly Ala Gln Ala
305                 310                 315                 320
Gly Ser Asn Asn Ser Gly Ser Val Ser Phe Asp Gly Glu Gly Val Val
                325                 330                 335
Phe Phe Ser Ser Asn Val Ala Gly Lys Gly Gly Ala Ile Tyr Ala
            340                 345                 350
Lys Lys Leu Ser Val Ala Asn Cys Gly Pro Val Gln Phe Leu Arg Asn
            355                 360                 365
Ile Ala Asn Asp Gly Gly Ala Ile Tyr Leu Gly Glu Ser Gly Glu Leu
            370                 375                 380
Ser Leu Ser Ala Asp Tyr Gly Asp Ile Ile Phe Asp Gly Asn Leu Lys
385                 390                 395                 400
Arg Thr Ala Lys Glu Asn Ala Ala Asp Val Asn Gly Val Thr Val Ser
                405                 410                 415
Ser Gln Ala Ile Ser Met Gly Ser Gly Lys Ile Thr Thr Leu Arg
            420                 425                 430
Ala Lys Ala Gly His Gln Ile Leu Phe Asn Asp Pro Ile Glu Met Ala
            435                 440                 445
```

```
Asn Gly Asn Asn Gln Pro Ala Gln Ser Ser Lys Leu Leu Lys Ile Asn
    450                 455                 460
Asp Gly Glu Gly Tyr Thr Gly Asp Ile Val Phe Ala Asn Gly Ser Ser
465                 470                 475                 480
Thr Leu Tyr Gln Asn Val Thr Ile Glu Gln Gly Arg Ile Val Leu Arg
                485                 490                 495
Glu Lys Ala Lys Leu Ser Val Asn Ser Leu Ser Gln Thr Gly Gly Ser
            500                 505                 510
Leu Tyr Met Glu Ala Gly Ser Thr Trp Asp Phe Val Thr Pro Gln Pro
        515                 520                 525
Pro Gln Gln Pro Pro Ala Ala Asn Gln Leu Ile Thr Leu Ser Asn Leu
    530                 535                 540
His Leu Ser Leu Ser Ser Leu Leu Ala Asn Asn Ala Val Thr Asn Pro
545                 550                 555                 560
Pro Thr Asn Pro Pro Ala Gln Asp Ser His Pro Ala Val Ile Gly Ser
                565                 570                 575
Thr Thr Ala Gly Ser Val Thr Ile Ser Gly Pro Ile Phe Phe Glu Asp
            580                 585                 590
Leu Asp Asp Thr Ala Tyr Asp Arg Tyr Asp Trp Leu Gly Ser Asn Gln
        595                 600                 605
Lys Ile Asn Val Leu Lys Leu Gln Leu Gly Thr Lys Pro Pro Ala Asn
    610                 615                 620
Ala Pro Ser Asp Leu Thr Leu Gly Asn Glu Met Pro Lys Tyr Gly Tyr
625                 630                 635                 640
Gln Gly Ser Trp Lys Leu Ala Trp Asp Pro Asn Thr Ala Asn Asn Gly
                645                 650                 655
Pro Tyr Thr Leu Lys Ala Thr Trp Thr Lys Thr Gly Tyr Asn Pro Gly
            660                 665                 670
Pro Glu Arg Val Ala Ser Leu Val Pro Asn Ser Leu Trp Gly Ser Ile
        675                 680                 685
Leu Asp Ile Arg Ser Ala His Ser Ala Ile Gln Ala Ser Val Asp Gly
    690                 695                 700
Arg Ser Tyr Cys Arg Gly Leu Trp Val Ser Gly Val Ser Asn Phe Phe
705                 710                 715                 720
Tyr His Asp Arg Asp Ala Leu Gly Gln Gly Tyr Arg Tyr Ile Ser Gly
                725                 730                 735
Gly Tyr Ser Leu Gly Ala Asn Ser Tyr Phe Gly Ser Ser Met Phe Gly
            740                 745                 750
Leu Ala Phe Thr Glu Val Phe Gly Arg Ser Lys Asp Tyr Val Val Cys
        755                 760                 765
Arg Ser Asn His His Ala Cys Ile Gly Ser Val Tyr Leu Ser Thr Gln
    770                 775                 780
Gln Ala Leu Cys Gly Ser Tyr Leu Phe Gly Asp Ala Phe Ile Arg Ala
785                 790                 795                 800
Ser Tyr Gly Phe Gly Asn Gln His Met Lys Thr Ser Tyr Thr Phe Ala
                805                 810                 815
Glu Glu Ser Asp Val Arg Trp Asp Asn Asn Cys Leu Ala Gly Glu Ile
            820                 825                 830
Gly Ala Gly Leu Pro Ile Val Ile Thr Pro Ser Lys Leu Tyr Leu Asn
        835                 840                 845
Glu Leu Arg Pro Phe Val Gln Ala Glu Phe Ser Tyr Ala Asp His Glu
    850                 855                 860
```

-continued

```
Ser Phe Thr Glu Glu Gly Asp Gln Ala Arg Ala Phe Lys Ser Gly His
865                 870                 875                 880

Leu Leu Asn Leu Ser Val Pro Val Gly Val Lys Phe Asp Arg Cys Ser
            885                 890                 895

Ser Thr His Pro Asn Lys Tyr Ser Phe Met Ala Ala Tyr Ile Cys Asp
                900             905                 910

Ala Tyr Arg Thr Ile Ser Gly Thr Glu Thr Thr Leu Leu Ser His Gln
        915                 920                 925

Glu Thr Trp Thr Thr Asp Ala Phe His Leu Ala Arg His Gly Val Val
    930                 935                 940

Val Arg Gly Ser Met Tyr Ala Ser Leu Thr Ser Asn Ile Glu Val Tyr
945             950                 955                 960

Gly His Gly Arg Tyr Glu Tyr Arg Asp Ala Ser Arg Gly Tyr Gly Leu
            965                 970                 975

Ser Ala Gly Ser Arg Val Arg Phe
            980
```